(12) United States Patent
Ozeran

(10) Patent No.: US 11,373,739 B2
(45) Date of Patent: Jun. 28, 2022

(54) SYSTEMS AND METHODS FOR INTERROGATING CLINICAL DOCUMENTS FOR CHARACTERISTIC DATA

(71) Applicant: Tempus Labs, Chicago, IL (US)

(72) Inventor: Jonathan Ozeran, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 16/852,216

(22) Filed: Apr. 17, 2020

(65) Prior Publication Data

US 2020/0335188 A1    Oct. 22, 2020

Related U.S. Application Data

(60) Provisional application No. 62/835,489, filed on Apr. 17, 2019.

(51) Int. Cl.
*G16H 10/60* (2018.01)
*G06Q 50/22* (2018.01)
(Continued)

(52) U.S. Cl.
CPC .......... *G16H 10/60* (2018.01); *G06F 40/186* (2020.01); *G06Q 50/22* (2013.01); *G16H 50/20* (2018.01)

(58) Field of Classification Search
CPC ........ G06F 1/00–2221/2153; G16H 10/00–80; G06Q 10/00–2250/905
See application file for complete search history.

(56) References Cited

U.S. PATENT DOCUMENTS 7,716,072 B1 * 5/2010 Green, Jr. ............. G06F 19/328
                                                             705/3
8,050,938 B1 * 11/2011 Green, Jr. ............. G06Q 50/24
                                                             705/2
(Continued)

FOREIGN PATENT DOCUMENTS

JP       2005-510326 A  *  4/2005  ............. G06Q 10/10

OTHER PUBLICATIONS

Reiner, "Customization of Medical Report Data," Journal of Digital Imaging, vol. 23, No. 4 Aug. 2010: pp. 363-373. (Year: 2010).*
(Continued)

*Primary Examiner* — Elaine Gort
*Assistant Examiner* — Jonathon A. Szumny
(74) *Attorney, Agent, or Firm* — Quarles & Brady LLP

(57) ABSTRACT

A computer program product includes multiple microservices for interrogating clinical records according to one or more projects associated with patient datasets obtained from electronic copies of source documents from the clinical records. A first microservice generates a user interface including a first portion displaying source documents and, concurrently, a second portion displaying structured patient data fields organized into categories for entering structured patient data derived from the source documents displayed in the first portion. Categories and their organization are defined by a template and include cancer diagnosis, staging, tumor size, genetic results, and date of recurrence. A second microservice validates abstracted patient data according to validation rules applied to the categories, validation rules being assigned to the projects and performed on the categories as they are populated. A third microservice provides abstraction review performed by an assigned abstractor or an abstraction manager and spans one or more of the projects.

31 Claims, 73 Drawing Sheets

(51) Int. Cl.
*G06F 40/186* (2020.01)
*G16H 50/20* (2018.01)

(56) References Cited

U.S. PATENT DOCUMENTS

| | | | | |
|---|---|---|---|---|
| 8,612,261 | B1* | 12/2013 | Swanson | G06F 19/3418 |
| | | | | 705/3 |
| 8,892,594 | B1* | 11/2014 | Khafizov | G06K 9/4604 |
| | | | | 707/769 |
| 9,262,731 | B1* | 2/2016 | Koushik | G06Q 10/10 |
| 10,614,196 | B2* | 4/2020 | Maitra | G16H 10/60 |
| 2005/0228815 | A1* | 10/2005 | Carus | G16H 10/60 |
| 2007/0250462 | A1* | 10/2007 | Wilson | G16H 50/20 |
| | | | | 706/13 |
| 2008/0091780 | A1* | 4/2008 | Balan | H04L 67/04 |
| | | | | 709/204 |
| 2009/0094059 | A1* | 4/2009 | Coleman | G06Q 50/22 |
| | | | | 705/3 |
| 2011/0040555 | A1* | 2/2011 | Wegner | G06F 40/20 |
| | | | | 704/9 |
| 2011/0202370 | A1* | 8/2011 | Green, III | G06Q 50/24 |
| | | | | 705/3 |
| 2011/0301982 | A1* | 12/2011 | Green, Jr. | G16H 50/20 |
| | | | | 705/3 |
| 2013/0091126 | A1* | 4/2013 | Krishnaswami | G16B 20/00 |
| | | | | 707/722 |
| 2013/0151286 | A1* | 6/2013 | Kablotsky | G06F 19/321 |
| | | | | 705/3 |
| 2013/0268290 | A1 | 10/2013 | Jackson | |
| 2013/0311201 | A1* | 11/2013 | Chatfield | G16H 50/20 |
| | | | | 705/3 |
| 2014/0372965 | A1* | 12/2014 | Alibakhsh | G06Q 10/06 |
| | | | | 717/101 |
| 2015/0169827 | A1 | 6/2015 | Laborde | |
| 2015/0320365 | A1* | 11/2015 | Schulze | A61B 5/748 |
| | | | | 600/408 |
| 2015/0324547 | A1* | 11/2015 | Graham | G06F 19/3456 |
| | | | | 705/2 |
| 2016/0110523 | A1* | 4/2016 | Francois | G16H 10/20 |
| | | | | 705/2 |
| 2016/0283657 | A1* | 9/2016 | Bhotika | G16H 50/20 |
| 2016/0300019 | A1* | 10/2016 | Baluta | G06F 16/285 |
| 2016/0378922 | A1* | 12/2016 | Shiu | G06F 19/328 |
| | | | | 705/2 |
| 2017/0109341 | A1* | 4/2017 | Issa | G06F 9/451 |
| 2017/0154156 | A1* | 6/2017 | Sevenster | G16H 40/63 |
| 2017/0235883 | A1* | 8/2017 | Harmon | G16H 40/20 |
| | | | | 705/3 |
| 2018/0085582 | A1* | 3/2018 | Calle | A61N 1/37217 |
| 2018/0114595 | A1* | 4/2018 | Stern | H04L 67/1004 |
| 2018/0350458 | A1* | 12/2018 | Soble | G16H 30/40 |
| 2018/0365612 | A1* | 12/2018 | Spofford | G06Q 10/20 |
| 2019/0006032 | A1* | 1/2019 | Groth | G06F 19/00 |
| 2019/0088356 | A1 | 3/2019 | Oliver | |
| 2020/0051675 | A1* | 2/2020 | Nelson | G16H 15/00 |
| 2020/0293528 | A1* | 9/2020 | Jonassen | G06F 16/24522 |

OTHER PUBLICATIONS

ELASTIC. Elasticsearch Reference. Accessed online at https://www.elastic.co/guide/en/elasticsearch/reference/current/index.html on Apr. 8, 2019.
ELASTIC. Query DSL webpage. Accessed online at https://www.elastic.co/guide/en/elasticsearch/reference/current/query-dsl.html on Jan. 16, 2019.
International Searching Authority. International Search Report and Written Opinion for application PCT/US2020/028832. dated Jul. 8, 2020.
Nissen, F., et al. "How to validate a diagnosis recorded in electronic health records." Breathe 15.1 (2019): 64-68.
Preuveneers, D. et al. "Access control with delegated authorization policy evaluation for data-driven microservice workflows." Future Internet 9.4 (2017): 58.
Yang, Y., et al. "Microshare: privacy-preserved medical resource sharing through microservice architecture." International Journal of Biological Sciences 14.8 (2018): 907.
U.S. Appl. No. 16/657,804, filed Oct. 18, 2019.
U.S. Appl. No. 62/787,249. filed Dec. 31, 2018.

* cited by examiner

FIG. 2

PATIENTS | PROJECTS | TEMPLATES | VALUESETS | MAGNET | QA MANAGER

Jane Doe | d6a970c6-3303-40fb-a404-84d514a66252 | DEFAULT | Uncategorized (5) | Unread (4) | 100 | All Changes Saved | Pause Session Demographics
Diagnosis
Treatments and outcomes
Genetic Testing and Labs Genetic Testing and Labs
⌄ Genetic Testing 1
Date of Testing Result
[MM ▾] [DD ▾] [YYYY ▾]
Testing Provider
[_____]
Date of Specimen Collection
[03 ▾] [03 ▾] [2017 ▾]
Test Method
[FISH (Fluorescence in situ hybridization) ▾]
⌄ Genetic Results 1
Gene    Result
[____▾] [____▾]

☆ Pathology Report | ☆ Progress Note | ☆ Lab Report | ☆ Lab Report | ☆ Progress Note
3/28/2013 | 3/12/2013 | 3/12/2013 | 3/12/2013 | 3/11/2013

Collection Date:

FINAL DIAGNOSIS:
PART 1: OMENTUM, OMENTECTOMY -
  BENIGN OMENTAL ADIPOSE TISSUE.
PART 2: UTERUS, CERVIX AND BILATERAL ADNEXA (172 grams), HYSTERECTOMY AND
  BILATERAL SALPINGO-OOPHORECTOMY -
  A. MALIGNANT MIXED MULLERIAN TUMOR (CARCINOSARCOMA) (see comment).
  B. THE TUMOR INVADES 18% OF THE MYOMETRIAL THICKNESS (0.2 cm INVASION
     OF 1.1 cm THICK MYOMETRIUM).
  C. THE TUMOR INVOLVES A PRE-EXISTING SUBMUCOSAL LEIOMYOMA.
  D. THE TUMOR MEASURES 7.2 CM IN LARGEST DIMENSION AND IS PRESENT AS A
     POLYPOID MASS IN THE ENDOMETRIAL CAVITY.
  E. CERVIX IS NEGATIVE FOR TUMOR.
  F. NO DEFINITE LYMPHOVASCULAR SPACE INVASION IS IDENTIFIED (see comment).
  G. THE BACKGROUND ENDOMETRIUM IS INACTIVE.
  H. THE MYOMETRIUM SHOWS LEIOMYOMAS.
  I. ALL ADNEXAE ARE NEGATIVE FOR TUMOR.
  J. THE LEFT PARATUBAL TISSUE SHOWS A LIPOMA.
PART 3: ABDOMINAL PERITONEUM, RIGHT, BIOPSY -
  FIBROADIPOSE TISSUE, NO TUMOR PRESENT.
PART 4: LYMPH NODES, RIGHT PELVIC, DISSECTION -
  FIVE LYMPH NODES, NO TUMOR PRESENT (0/5).

PATIENTS | PROJECTS | TEMPLATES | VALUESETS | MAGNET | QA MANAGER

Jane Doe | d6a970c5-3303-40fb-a404-84d514a66252 | DEFAULT

Demographics
Diagnosis
Treatments and outcomes
Genetic Testing and Labs

Molecular Variant

⊞ Add Gene Results

∨ Other Results
Tumor Mutational Burden (TMB)

Sequencing and TMB or MSI or GENES are required
Microsatellite Instability (MSI)

Sequencing and TMB or MSI or GENES are required

∨ Genetic Testing 2
Date of Testing Result
MM ▾  DD ▾  YYYY ▾

Testing Provider
Guardant ▾

Submit for review

Uncategorized (5) | Unread (4)

☆ Pathology Report 3/28/2013 | ☆ Progress Note 3/12/2013 | ☆ Lab Report 3/12/2013 | ☆ Lab Report 3/12/2013 | ☆ Progress Note 3/11/2013

Collection Date:

FINAL DIAGNOSIS:

PART 1: OMENTUM, OMENTECTOMY -
    BENIGN OMENTAL ADIPOSE TISSUE.

PART 2: UTERUS, CERVIX AND BILATERAL ADNEXA (172 grams), HYSTERECTOMY AND BILATERAL SALPINGO-OOPHORECTOMY -
  A. MALIGNANT MIXED MULLERIAN TUMOR (CARCINOSARCOMA) (see comment).
  B. THE TUMOR INVADES 18% OF THE MYOMETRIAL THICKNESS (0.2 cm INVASION OF 1.1 cm THICK MYOMETRIUM).
  C. THE TUMOR INVOLVES A PRE-EXISTING SUBMUCOSAL LEIOMYOMA.
  D. THE TUMOR MEASURES 7.2 CM IN LARGEST DIMENSION AND IS PRESENT AS A POLYPOID MASS IN THE ENDOMETRIAL CAVITY.
  E. CERVIX IS NEGATIVE FOR TUMOR.
  F. NO DEFINITE LYMPHOVASCULAR SPACE INVASION IS IDENTIFIED (see comment).
  G. THE BACKGROUND ENDOMETRIUM IS INACTIVE.
  H. THE MYOMETRIUM SHOWS LEIOMYOMAS.
  I. ALL ADNEXAE ARE NEGATIVE FOR TUMOR.
  J. THE LEFT PARATUBAL TISSUE SHOWS A LIPOMA.

PART 3: ABDOMINAL PERITONEUM, RIGHT, BIOPSY -
    FIBROADIPOSE TISSUE, NO TUMOR PRESENT.

PART 4: LYMPH NODES, RIGHT PELVIC, DISSECTION -
    FIVE LYMPH NODES, NO TUMOR PRESENT (0/5).

FIG. 7

| PATIENTS PROJECTS TEMPLATES VALUESETS MAGNET QA MANAGER VALIDATIONS MANAGER | | | | | |
|---|---|---|---|---|---|
| | | | | Create New | |
| NAME | DESCRIPTION | CREATED AT | CREATED BY | LEVEL | EDIT▾ |
| Lytic count must be a number if operator is. | Value must be a num | 12/18/18 05:56:50 | 35894307-7c21-4025-abff-89aecb5bb3b3 | ERROR | Edit |
| Menopause status | Patient is not female | 03/21/19 09:05:05 | ea31e4ba-f842-45ba-965c-87584a496cda | WARNING | Edit |
| Diagnosis cannot be duplicate | Duplicate tissue of origin | 12/18/18 05:56:50 | 35894307-7c21-4025-abff-89aecb5bb3b3 | WARNING | Edit |
| Lab tests test result is name | Must be a number | 12/18/18 05:56:50 | 35894307-7c21-4025-abff-89aecb5bb3b3 | ERROR | Edit |
| Date Validations | Invalid date | 12/18/18 05:56:50 | 35894307-7c21-4025-abff-89aecb5bb3b3 | ERROR | Edit |
| Gene raw result | Must be number | 02/28/19 04:55:39 | 7b9efc70-df76-4696-bb80-4939b4bdd607 | ERROR | Edit |
| Tumor characterizations tumor size | Tumor image size and units are required | 12/18/18 05:56:50 | 35894307-7c21-4025-abff-89aecb5bb3b3 | ERROR | Edit |
| Tumor characterization before earliest date of diagnosis | Data must be after diagnosis or earliest identification | 12/18/18 05:56:50 | 35894307-7c21-4025-abff-89aecb5bb3b3 | ERROR | Edit |
| Lab test lower limit is less than upper limit | Lower limits must be less than upper limit | 12/18/18 05:56:50 | 35894307-7c21-4025-abff-89aecb5bb3b3 | ERROR | Edit |
| Immunophenotyping result text is a number | Should be a Number | 12/18/18 05:56:50 | 35894307-7c21-4025-abff-89aecb5bb3b3 | ERROR | Edit |
| Lab tests test result and test text can't exits together | Excess field | 12/18/18 05:56:50 | 35894307-7c21-4025-abff-89aecb5bb3b3 | ERROR | Edit |

PATIENTS PROJECTS TEMPLATES VALUESETS MAGNET QA MANAGER VALIDATIONS MANAGER

Edit validation

Name
[Tumor characterizations tumor size]

Effective As Of
[03/23/2019] 🗓

Level
[ERROR ▼]

Description
[Tumor image size and units are required]

Add Block

| Logical | ∨ |
| boolean | ∨ |
| comparison | ∨ |
| group | ∨ |
| fields | ∨ |
| accessors | ∨ |
| value | ∨ | exists
isValidDate
nexists
nisValidDate
in
nin
regexp
nregexp

→

[Save Validation]

[Save Validation]

PATIENTS PROJECTS TEMPLATES VALUESETS MAGNET QA MANAGER VALIDATIONS MANAGER

Edit validation

Name

Tumor characterizations tumor size

Effective As Of

03/23/2019

Description

Tumor image size and units are required

Level

ERROR ▼

For | all ▼ | in

- demographics: Demographics
- diagnosis: Diagnosis
- treatmentsAndOutcomes: Treatments and outcomes
- geneticTestingAndLabs: Genetic Testing and Labs Add Block

1410

ADVANCED EDITION

Save Validation

Save Validation

PATIENTS PROJECTS TEMPLATES VALUESETS MAGNET QA MANAGER VALIDATIONS MANAGER

Edit validation

Save Validation

Name

| Tumor characterizations tumor size | | Effective As Of |
|---|---|---|
| | | 03/23/2019 |

Description

| Tumor image size and units are required |

Level

| ERROR ▼ |

For | all ▼ | in | diagnosis.primaryDiagnosis.site.display | : | | ✕

| diagnosis.primaryDiagnosi... | Type . to get suggestions... | | exists ▼ | ✕

→

ADVANCED EDITION 1510

Save Validation

PATIENTS PROJECTS TEMPLATES VALUESETS MAGNET QA MANAGER VALIDATIONS MANAGER

Edit validation

Name
[Tumor characterizations tumor size]

Level
[ERROR ▼]

Effective As Of
[03/23/2019] 📅

Description
[Tumor image size and units are required]

[Save Validation]

For [all ▼] in [.diagnosis.primaryDiagnosis] [.diagnosis.primaryDiagnosis.site.display] :

[eq ▼] [+Select a source or provide value]
— 1610

ADVANCED EDITION
1 ▸ {
2 ▸   "$$all": {
3 ▸   "$$eq": [

PATENTS PROJECTS TEMPLATES VALUESETS MAGNET QA MANAGER

Jane Doe | d6a97cc6-33c3-40fb-a404-84d514a66252

DEFAULT

Demographics
Diagnosis
Treatments and outcomes
Genetic Testing and Labs

Diagnosis
  ∨ Diagnosis
    ∨ Primary Diagnosis — 1810
      Tissue of Origin
      [Ovary ▾]
      Date of diagnosis
      [MM ▾] [DD ▾] [YYYY ▾]
      Date of recurrence 1
      [MM ▾] [DD ▾] [YYYY ▾]
      ○ Date unknown
      Date of biochemical recurrence 1
      [MM ▾] [DD ▾] [YYYY ▾]
      ○ Date unknown
      Date of CRPC 1
      [MM ▾] [DD ▾] [YYYY ▾]

Uncategorized (5) Unread (4)   ⊖ — 100 + ⊚ ⟲ ⟳ ⊙ —⚪— ⊚ All Changes Saved ‖Pause Session

| ☆ Pathology Report | ☆ Progress Note | ☆ Lab Report | ☆ Lab Report | ☆ Progress Note |
| 3/28/2013 | 3/12/2013 | 3/12/2013 | 3/12/2013 | 3/11/2013 |

Collection Date:

FINAL DIAGNOSIS:

PART 1: OMENTUM, OMENTECTOMY -
  BENIGN OMENTAL ADIPOSE TISSUE.

PART 2: UTERUS, CERVIX AND BILATERAL ADNEXA (172 grams), HYSTERECTOMY AND BILATERAL SALPINGO-OOPHORECTOMY -
  A. MALIGNANT MIXED MULLERIAN TUMOR (CARCINOSARCOMA) (see comment).
  B. THE TUMOR INVADES 18% OF THE MYOMETRIAL THICKNESS (0.2 cm INVASION OF 1.1 cm THICK MYOMETRIUM).
  C. THE TUMOR INVOLVES A PRE-EXISTING SUBMUCOSAL LEIOMYOMA.
  D. THE TUMOR MEASURES 7.2 CM IN LARGEST DIMENSION AND IS PRESENT AS A POLYPOID MASS IN THE ENDOMETRIAL CAVITY.
  E. CERVIX IS NEGATIVE FOR TUMOR.
  F. NO DEFINITE LYMPHOVASCULAR SPACE INVASION IS IDENTIFIED (see comment).
  G. THE BACKGROUND ENDOMETRIUM IS INACTIVE.
  H. THE MYOMETRIUM SHOWS LEIOMYOMAS.
  I. ALL ADNEXAE ARE NEGATIVE FOR TUMOR.
  J. THE LEFT PARATUBAL TISSUE SHOWS A LIPOMA.

PART 3: ABDOMINAL PERITONEUM, RIGHT, BIOPSY -
  FIBROADIPOSE TISSUE, NO TUMOR PRESENT.

PART 4: LYMPH NODES, RIGHT PELVIC, DISSECTION -
  FIVE LYMPH NODES, NO TUMOR PRESENT (0/5).

[Submit for review]

PATIENTS | PROJECTS | TEMPLATES | VALUESETS | MAGNET | QA MANAGER | VALIDATIONS MANAGER

QA | MANAGE COHORTS | MANAGE QUERIES

Go To Jobs

SEARCH

+Summary Search  +Patient Blob Search  +Validation Search  +Activities Search

Validation ▼ | In (at least one) ▼ | Result ▼ | — <

☐ Surgical Procedures Outcome date is required (1dd76c)
☐ Performance measure and date (05d56f)
☐ Sequencing provider is required (8d3b5f)
☐ Metastases Tumor size (233dec)
☐ Amount and units are required (af9cdf)
☐ AJCC Lung Additional Tumor Characterizaions (07f1a8)
☐ Chromosome analysis abnormality exists (f24a7a)
☐ Heme Characterizations soft tissue plasmacytoma size and units (a623d3)

2210

S | QA | IRR | IRR | COHORTS | ACTIVITY | VALIDATION
| | REVIEWER | SCORE | | |

0 PATIENTS ▷

PATIENTS  PROJECTS  TEMPLATES  VALUESETS  MAGNET  QA MANAGER  VALIDATIONS MANAGER

QA   MANAGE COHORTS   MANAGE QUERIES

SEARCH

+Summary Search   +Patient Blob Search   +Validation Search   +Activities Search

[Sequencing genes at least one required (77a64e) ▼]   [In (at least one) ▼]   [Failed ▼]

[Search]   ← 2310

Go To Jobs

193 PATIENTS

| | PATIENT NAME | ID | PROJECT | ABSTRA-CTORS | QA REVIEWER | IRR | IRR SCORE | COHORTS | ACTIVITY | VALIDATION |
|---|---|---|---|---|---|---|---|---|---|---|
| ☐ | Michael John | 0165946d-7702... | Ovarian Stage II | | | | | | Case Created 08/05/18 02:34:17 | FAILED > |
| ☐ | Thomas Campton | 0344c6a7-1d78... | Cancer Center Missouri | | | | | | Attachment Updated 08/01/18 05:59:22 | FAILED > |
| ☐ | Brian Thompson | 041ae2a0-4b17... | Pancreatic Stage IV | | | | | | Attachment Updated 08/01/18 10:24:35 | FAILED > |
| ☐ | Mary Ali | 0631b801-b2eb... | Lung Stage III | | | | | | Case Created 08/01/18 08:29:07 | FAILED > |
| ☐ | Carson Smith | 06803b07-fc19... | Island Medical Center | | | | | | Case Created 07/31/18 10:28:34 | FAILED > |
| ☐ | Allison Roth | 0770cef8-f059... | Pinegroves Cancer Research Facility | | | | | | Case Created 07/31/18 10:41:54 | FAILED > |
| ☐ | Nicole Nathons | 07b1a8ef-dd32... | Ovarian Postmenopausal | | | | | | Case Created 09/06/18 03:50:55 | FAILED > |
| ☐ | Richard Kelly | 08e10cfe-1a67... | Breast Remission | | | | | | | |

Templates_and_Valuesets

"I" EMPUS

PATIENTS  PROJECTS  TEMPLATES  VALUESETS  MAGNET  QA MANAGER  VALIDATIONS MANAGER

Template Creation — 2630

☐ Show Archived

2650 — NEW TEMPLATE

Pancreas Male
Created 3/13/2018
Projects
Pancreas Stage IV
Pancreas Stage I/II
view all (7)
○ Published  ⊕
3/12/2019

Pinegroves Cancer Research Facility
Created 3/20/2018
Projects
Lung Cancer Stage IV
○ Published  ⊕
3/12/2019

Lung Female
Created 3/21/2018
Projects
○ Published  ⊕
3/21/2019

Island Medical Center
Created 3/21/2018
Projects

Cancer Center Missouri
Created 3/22/2018
Projects

Richardson Hospital
Created 3/21/2018
Projects
○ Published  ⊕
3/12/2019

Six Rivers Cancer Center
Created 3/22/2018
Projects

JZS Cancer Center
Created 3/22/2018
Projects 2640
2620
2610

"T" EMPUS

PATIENTS  PROJECTS  TEMPLATES  VALUESETS  MAGNET  QA MANAGER

Jane Doe | 80b55e10-2d84-4a90-a877-3c4a86f164bf | 🔍 − 100 + ⟳ ⊘ ─●─ ⊚ All changes Saved. ■ Pause Session

Demographics
Diagnosis
Treatments and outcomes
Genetic Testing and Labs

Demographics
∨ Demographics
  Gender   ○ female   ○ male
  Race [▼]
  Date of birth [MM▼] [DD▼] [YYYY▼]   ← 2720
                  ↑2710  ↑2710
  Date of death [MM▼] [DD▼] [YYYY▼]
  ○ Deceased
  Cancer at Death [▼]
  Date of last follow-up
  [MM▼] [DD▼] [YYYY▼]
  [Submit for review]

| DEFAULT | Uncategorized (6) | Unread (5) |

| Progress Note 3/12/2013 | Progress Note 3/12/2013 | Lab Report 3/12/2013 | Lab Report 3/12/2013 | Progress Note 3/11/2013 | Genetic Testing 2/07/2013 |

○  TSS ID:
   TSS ID:         OC ID           Date of Procurement

Gross Description:
   Lump with the tumor of 1.2 x 1.3cm in size.
   Fatty tissue lymph nodes demonstrate lipomatosis.

Microscopic Description:
   Infiltraing duct carcinoma; G3.
   Ten dissected lymph nodes demonstrate focal fibrosis, reactive hyperplasia of the follicles.

Diagnosis details:
   Tumor Features: Unknown, Tumor Extent: T1 tumor size 2 cm or less, Venous Invasion: Absent,
   Margins: Absent, Treatment Effect:

Comments:
   Formatted Path Report ;

*"t" EMPUS*

| PATIENTS | PROJECTS | TEMPLATES | VALUESETS | MAGNET | QA MANAGER |

Jane Doe | 80b55e10-2d84-4a90-a87f-3c4a86f164bf

DEFAULT | Uncategorized (6) Unread (5)

Demographics
Diagnosis
Treatments and outcomes
Genetic Testing and Labs

Treatments and outcomes
∨ Treatments and outcomes
  □ Add Therapy Groups
∨ Surgical Procedure 1
  Surgical Procedure ▼

Date
MM ▼ DD ▼ YYYY ▼

Discharge Date
MM ▼ DD ▼ YYYY ▼

Resection Margin
▼

□ Add Surgical Procedure
□ Add Clinical Trials

[Submit for review]

| Progress Note 3/12/2013 | Progress Note 3/12/2013 | Lab Report 3/12/2013 | Lab Report 3/12/2013 | Progress Note 3/11/2013 | Genetic Testing 2/07/2013 |

Progress Note 3/12/2013

TSS ID:
TSS ID:    OC ID:           Date of Procurement

Gross Description:
Lump with the tumor of 1.2 x 1.3cm in size.
Fatty tissue lymph nodes demonstrate lipomatosis.

Microscopic Description:
Infiltrating duct carcinoma; G3.
Ten dissected lymph nodes demonstrate focal fibrosis, reactive hyperplasia of the follicles.

Diagnosis details:
Tumor Features: Unknown, Tumor Extent: T1 tumor size 2 cm or less, Venous Invasion: Absent,
Margins: Absent, Treatment Effect:

Comments:
Formatted Path Report ;

Saving    ▪▪ Pause Session 2900
2910

"F" EMPUS

PATIENTS  PROJECTS  TEMPLATES  VALUESETS  MAGNET  QA MANAGER  VALIDATIONS MANAGER

Six Rivers Cancer Center

| COMPONENTS | | | Cancel | Save & Close 3310 | Save & Publish 3320 |
|---|---|---|---|---|---|
| Demographics | 17 | ☑ FIELDS | | | |
| Diagnosis | 2 | ☐ Addressess | REPEATABLE | N/A | SOLID ▼ |
| Treatment And Outcomes | 6 | ☐ Address Use | SELECT ▼ | Address - Use | 4 values |
| Genetic Testing And Labs | 3 | ☐ Address Type | SELECT ▼ | Address - Type | 3 values |
| | | ☐ Address | TEXT + | N/A | |
| | | ☐ Address City State Zip Row | ROW | N/A | |
| | | ☐ City | TEXT | N/A | |
| | | ☐ State | DROPDOWN ▼ | State | 50 values |
| | | ☐ Zip | TEXT | N/A | |

"t" EMPUS

PATIENTS  PROJECTS  TEMPLATES  VALUESETS  MAGNET QA MANAGER  VALIDATIONS MANAGER

Add Template Name

Cancel    Save & Close    Save & Publish

| COMPONENTS | | FIELDS | | | |
|---|---|---|---|---|---|
| Demographics | 14 | ☑ Gender | SELECT | patient sex - default ▼ | 2 values |
| Heme Diagnosis | 2 | ☑ Race | DROPDOWN | patient race - default ▼ | 13 values |
| Treatment And Outcomes | 6 | ☑ Date of birth | DATE | NA | |
| Genetic Testing And Labs | 6 | ☑ Smoking statuses | DROPDOWN & DATE + | smoking status - default ▼ | 3 values |
| | | ☑ Date of hospice admission | DATE + | NA | |
| | | ☑ Date of hospital admission | DATE + | NA | |
| | | ☑ Comorbidities | DROPDOWN & DATE + | comorbidities - default ▼ | 3092 values |
| | | ☑ Personal History of Cancer | REPEATABLE | NA | |

HEME ▼

PATIENTS PROJECTS TEMPLATES VALUESETS MAGNET QA MANAGER VALIDATIONS MANAGER

Address - Use
ID: 845
Version: 1.0.0
url: https://ires.staging.tempus.com/valuesets/address_use System NCI T ▼ ☐

| | | | | | |
|---|---|---|---|---|---|
| Home | CODE DEFINITION | C18002 | ☐ | Work | CODE DEFINITION C17556 ☐ |
| Temp | CODE DEFINITION | C53288 | ☐ | Old | CODE DEFINITION C65010 ☐ |

Add rows
1 + Remove Rows with Empty Columns

[+System]  [+ValueSet]  [Save]

Magnet Creation 4900

| 4910 | 4920 | 4930 | 4940 Create New Query / 4950 List All Batches |

- Female - Breast
  Created 07/30/2018
  Batch:

- Stage II-IV Ovarian
  Created 08/27/2018
  Batch:

- Stage IV Pancreatic
  Created 02/27/2019
  Batch:

- QA Automation Magnet
  Created 10/08/2018
  Branch: TTRS-Breast-20170524-4

- Stage I Lung
  Created 07/17/2018
  Batch: EESC-Lung-20181108-1

- Stage I Breast
  Created 07/23/2018
  Batch: DRTX-Breast-20180830-17

- Stage I-III Colorectal
  Created 07/17/2018
  Batch:

- Stage IV Prostate
  Created 07/23/2018
  Batch:

JZS Cancer Center Query

5200 → 5210

Queries ⬆ ⬇ [RUN!] [Inspect] [Save]

Batch Id — 5220

Results ℹ 💾 Save
Showing 89 of 159650 in the batch

| ☐ Patient | Avg Order |
|---|---|
| ☐ 749bba16-7c5e-493e-a0f2-69cec4bff466 | 0 |
| ☐ 0173fa70-5096-455a-937f-7a808e0dbf7f  5250 | 1 |
| ☐ 0e938120-2969-4bc7-a570-3ab512aeff36 | 2 |
| ☐ 4734beec-3d4b-4a7a-ace6-8a960bcfdbe0 | 3 |
| ☐ 5616ba4f-1787-48e0-9d94-336cf63ff27c | 4 |
| ☐ 58ba7cf5-3e7c-45b8-9609-d30be46335e0 | 5 |
| ☐ 6a367d10-01e7-4142-b0b2-00f7db2bf129 | 6 |

Drug Name

Click on patient to get results — 5230

Queries

Phrase    Stop
○ "Herceptin"    0 − +

+

0173fa70-5096-455a-937f-7a808e0dbf7f

Project: JZS Cancer Center
OPEN CASE

5240

[Save]

FIG. 52

JZS Cancer Center Query 5300

Queries 🔼 ⬇ [RUN!]

Batch Id ─ 5320

Drug Name

Queries
- Phrase: "Herceptin"
- Slop: 0 +

+

Results [💾 Save] ─ 5330

Showing 89 of 159650 in the batch ─ 5310

| ☑ Patient | Avg Order | Inspect ─ 5340 [Save] |
|---|---|---|
| ☑ 749bba16-7c5e-493e-a0f2-69cec4bff466 | 0 | Based on genetic markers, Herceptin treatment is considered<br>Document: eb43ff2b-b0a5-468a-9998-b32762fe8111<br>Page: 1 |
| ☑ 0173fa70-5096-455a-937f-7a808e0db7f | 1 | Patient is responding favorably to Herceptin, continue with current treatment<br>Document: fab95315-51a2-49d9-d1e-638b91f99<br>Page: 1 |
| ☑ 0e938120-2969-4bc7-a570-3ab512aeff36 | 2 | |
| ☑ 47346eec-6d4b-4a7a-ace6-8a960bcfdbe0 | 3 | Clinical trying using Herceptin has proven to be effective for patients with similar genetic profiles<br>Document: f06584ad-9f0c-49d2-939c-5b1d027f2331<br>Page: 1 |
| ☑ 56160a44-1787-48e0-9d94-336cf63ff27c | 4 | |
| ☑ 58ba7cf5-3e7c-45b8-9609-d30be46335e0 | 5 | Patient has failed adjuvant therapy, recommend switching to salvage Herceptin |
| ☑ 6a367d10-01e7-4142-b0b2-00f7db2bf129 | 6 | |

| Phrase | Slop | |
|---|---|---|
| 183 | 0 | - |
| Phrase | Slop | |
| c56 | 0 | - |
| Phrase | Slop | |
| c57 | 0 | + |

Stage II - IV

| | | |
|---|---|---|
| ☐ | 7a808e0dbff | |
| ☐ | 5616a44f-1787-48e0-9d94-336cf63ff27c | 30 |
| ☐ | c5032ba0-ddd3-4ce0-9b38-d93d1c15989 | 31 |
| ☐ | e39cdcfc-d73e-4e42-aa4f-e4bba5602190 | 32 |
| ☐ | 1f0fb1b7-82a4-490f-9cb0-2135ab72b394 | 36 |
| ☐ | 85e14da0-c3b2-405c-af46-1c50f27cd454 | 39 |
| ☐ | 689e2b51-fc20-42b-8384-91aeb0a3e4b6 | 43 |
| ☐ | c10322ee-4k99-43f0-92c6-fb644fded317 | 63 |
| ☐ | 6d33ad89-d4c2-413b-b221-e625a342ba46 | 69 |
| ☐ | 0f960bd9-4afc-4611-90a2-ec1e57399fdb | 73 |

Queries

| Phrase | Slop | |
|---|---|---|
| stage Sii | 0 | - |
| Phrase | Slop | |
| stage Siia | 0 | - |

| condition_occurrence_id | person_id | condition_concept_id | condition_start | condition_end | condition_type_concept_id | visit_occurrence_id | condition_source_value | condition_source_concept_id |
|---|---|---|---|---|---|---|---|---|
| 123456789 | ABC123DEF456 | 35208182 | 7/25/17 | 7/25/17 | 44786627 | 46804872 | C32.9 | 7992289 |

FIG. 60

| drug_concept_id | person_id | drug_exposure_start | drug_exposure_end | drug_source_value | drug_source_concept_id | route_source_value | dose_unit_source_value |
|---|---|---|---|---|---|---|---|
| 45329886 | ABC123DEF456 | 7/28/17 | 7/28/17 | PACLITAXEL 6 MG/ML CONCENTRATE, IV | 72370 | intravenous | ml |

SYSTEMS AND METHODS FOR INTERROGATING CLINICAL DOCUMENTS FOR CHARACTERISTIC DATA

CROSS-REFERENCE TO RELATED APPLICATIONS

This application claims the benefit of priority to U.S. Provisional Patent Application No. 62/835,489, titled "Systems and Methods for Interrogating Raw Clinical Documents for Characteristic Data," filed Apr. 17, 2019.

This application also incorporates by reference in its entirety U.S. Provisional Patent Application No. 62/787,249, titled "Automated Quality Assurance Testing of Structured Clinical Data," filed Dec. 31, 2018.

BACKGROUND OF THE DISCLOSURE

The present invention relates to systems and methods for obtaining and employing data related to patient characteristics, such as physical, clinical, or genomic characteristics, as well as diagnosis, treatments, and treatment efficacy to provide a suite of tools to healthcare providers, researchers, and other interested parties enabling those entities to develop new insights utilizing disease states, treatments, results, genomic information and other clinical information to improve overall patient healthcare.

Definitions

Hereafter, unless indicated otherwise, the following terms and phrases will be used in this disclosure as described.

The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, clinical trial designers, data abstractors, oncologists, neurologists, psychiatrists, data scientists, and many other persons with specialized skill sets.

The term "physician" will be used to refer generally to any health care provider including but not limited to a primary care physician, a medical specialist, an oncologist, a neurologist, a nurse, and a medical assistant, among others.

The term "researcher" will be used to refer generally to any person that performs research including but not limited to a radiologist, a data scientist, or other health care provider. One person may be both a physician and a researcher while others may simply operate in one of those capacities.

The phrase "system specialist" will be used generally to refer to any provider employee that operates within the disclosed systems to collect, develop, analyze or otherwise process system data, tissue samples or other information types (such as medical images) to generate any intermediate system work product or final work product where intermediate work product includes any data set, conclusions, tissue or other samples, or other information for consumption by one or more other system specialists and where final work product includes data, conclusions or other information that is placed in a final or conclusory report for a system client or that operates within the system to perform research, to adapt the system to changing needs, data types or client requirements. For instance, the phrase "abstractor specialist" will be used to refer to a person that consumes data available in clinical records provided by a physician (such as primary care physician or psychiatrist) to generate normalized and structured data for use by other system specialists. The phrase "programming specialist" will be used to refer to a person that generates or modifies application program code to accommodate new data types and or clinical insights, etc.

The phrase "system user" will be used generally to refer to any person that uses the disclosed system to access or manipulate system data for any purpose, and therefore will generally include physicians and researchers that work for the provider or that partner with the provider to perform services for patients or for other partner research institutions as well as system specialists that work for the provider.

The term "consume" will be used to refer to any type of consideration, use, modification, or other activity related to any type of system data, saliva samples, etc., whether or not that consumption is exhaustive (such as used only once, as in the case of a saliva sample that cannot be reproduced) or inexhaustible so that the data, sample, etc., persists for consumption by multiple entities (such as used multiple times as in the case of a simple data value). The term "consumer" will be used to refer to any system entity that consumes any system data, samples, or other information in any way including each of specialists, physicians, researchers, clients that consume any system work product, and software application programs or operational code that automatically consume data, samples, information or other system work product independent of any initiating human activity.

The term "structured" clinical data refers to clinical data that has been ingested into a structured format governed by a data schema. As one simple example, structured clinical data may be patient name, diagnosis date, and a list of medications, arranged in a JSON format. It should be understood that there are many, more complicated types of structured clinical data, which may take different formats.

The phrase "data schema" means a particular set of data attributes and relationships therein that comprise a set of structured data to be used for various purposes (e.g. internal analysis, integration with purpose-built applications, etc.).

The phrase "data element" means a particular clinical and/or phenotypic data attribute. For instance, a comorbidity (e.g. acute myocardial infarction), adverse event (e.g. conjunctivitis), performance score (e.g. ECOG score of 3), etc.

The phrase "data value" means the value of the data in a data element. For instance, in a "Diagnosis Date" data element, the data value may be "Oct. 10, 2016".

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Background

Medical treatment prescriptions or plans are typically based on an understanding of how treatments affect illness (such as treatment results) including how well specific treatments eradicate illness, duration of specific treatments, duration of healing processes associated with specific treatments and typical treatment-specific side effects. Ideally, treatments result in complete elimination of an illness in a short period with minimal or no adverse side effects. In some cases, cost is also a consideration when selecting specific medical treatments for specific ailments.

Knowledge about treatment results is often based on analysis of empirical data developed over decades or even longer time periods, during which physicians and/or researchers have recorded treatment results for many different patients and reviewed those results to identify generally successful ailment specific treatments. Researchers and physicians give medicine to patients or treat an ailment in some other fashion, observe results and, if the results are good, use the treatments again for similar ailments. If treatment results are bad, a physician forgoes prescribing the associated treatment for a next encountered similar ailment and instead tries some other treatment. Treatment results are sometimes published in medical journals and/or periodicals so that many physicians can benefit from a treating physician's insights and treatment results.

In many cases treatment results for specific diseases vary for different patients. In particular, different patients often respond differently to identical or similar treatments. Recognizing that different patients experience different results given effectively the same treatments in some cases, researchers and physicians often develop additional guidelines around how to optimize ailment treatments based on specific patient disease state. For instance, while a first treatment may be best for a younger, relatively healthy woman, a second treatment associated with fewer adverse side effects may be optimal for an older, relatively frail man with the same diagnosis. In many cases, patient conditions related to the disease state may be gleaned from clinical medical records, via a medical examination and/or via a patient interview, and may be used to develop a personalized treatment plan for a specific ailment. The idea here is to collect data on as many factors as possible that have any cause-effect relationship with treatment results and use those factors to design optimal personalized treatment plans.

Genetic testing has been explored as another disease state factor (such as another patient condition) that can affect treatment efficacy. It is believed that there are likely many DNA and treatment result cause-and-effect relationships that have yet to be discovered. One problem with genetic testing is that the testing is expensive and can be cost prohibitive in many cases—oftentimes, insurance companies refuse to cover the cost.

Another problem with genetic testing for treatment planning is that, if genetic testing is performed, often there is no clear linkage between resulting genetic factors and treatment efficacy. In other words, in most cases, how genetic test results can be used to prescribe better treatment plans for patients is not fully known, so the extra expense associated with genetic testing in specific cases cannot be justified. Thus, while promising, genetic testing as part of treatment planning has been minimal or sporadic at best.

In most cases, patient treatments and results are not published for general consumption and therefore are simply not accessible to be combined with other treatment and results data to provide a more fulsome overall data set. In this regard, many physicians see treatment results that are within an expected range of efficacy and may conclude that those results cannot add to the overall treatment knowledge base; those results often are not published. The problem here is that the expected range of efficacy can be large (such as 20% of patients experience a significant reduction in symptoms, 40% of patients experience a moderate reduction in symptoms, 20% experience a mild reduction in symptoms, and 20% do not respond to a treatment plan) so that all treatment results are within an expected efficacy range and treatment result nuances are simply lost.

Additionally, there is no easy way to build on and supplement many existing illness-treatment-results databases. As such, as more data is generated, the new data and associated results cannot be added to existing databases as evidence of treatment efficacy or to challenge efficacy. Thus, for example, if a researcher publishes a study in a medical journal, there is no easy way for other physicians or researchers to supplement the data captured in the study. Without data supplementation over time, treatment and results corollaries cannot be tested and confirmed or challenged.

The knowledge base around treatments is always growing with different clinical trials in different stages around the world so that if a physician's knowledge is current today, his knowledge will be dated within months. Thousands of articles relevant to diseases are published each year and many are verbose and/or intellectually thick so that the articles are difficult to read and internalize, especially by extremely busy physicians that have limited time to absorb new materials and information. Distilling publications down to those that are pertinent to a specific physician's practice takes time and is an inexact endeavor in many cases.

In most cases there is no clear incentive for physicians to memorialize a complete set of treatment and results data and, in fact, the time required to memorialize such data can operate as an impediment to collecting that data in a useful and complete form. To this end, prescribing and treating physicians know what they know and painstakingly capturing a complete set of disease state, treatment and results data without getting something in return (such as a new insight, a better prescriptive treatment tool, etc.) may be perceived as burdensome to the physician.

In addition to problems associated with collecting and memorializing treatment and results data sets, there are problems with digesting or consuming recorded data to generate useful conclusions. For instance, recorded disease state, treatment and results data is often incomplete. In most cases physicians are not researchers and they do not follow clearly defined research techniques that enforce tracking of all aspects of disease states, treatments and results. As a result, data that is recorded is often missing key information such as, for instance, specific patient conditions that may be of current or future interest, reasons why a specific treatment was selected and other treatments were rejected, specific results, etc. In many cases where cause and effect relationships exist between disease state factors and treatment results, if a physician fails to identify and record a causal factor, the results cannot be tied to existing cause and effect data sets and therefore simply cannot be consumed and added to the overall disease knowledge data set in a meaningful way.

Another impediment to digesting collected data is that physicians often capture disease state, treatment and results data in forms that make it difficult if not impossible to process the collected information so that the data can be normalized and used with other data from similar patient treatments to identify more nuanced insights and to draw more robust conclusions. For instance, many physicians prefer to use pen and paper to track patient care and/or use personal shorthand or abbreviations for different disease state descriptions, patient conditions, treatments, results and even conclusions. Using software to glean accurate information from hand written notes is difficult at best and the task is exacerbated when hand written records include personal abbreviations and shorthand representations of information that software simply cannot identify with the physician's intended meaning.

In precision medicine, physicians and other clinicians provide medical care designed to optimize efficiency or therapeutic benefit for patients on the basis of their particular characteristics. Each patient is different, and their different needs and conditions can present a challenge to health systems that must grapple with providing the right resources to their clinicians, at the right time, for the right patients. Health systems have a significant need for systems and methods that allow for precision-level analysis of patient health needs, in order to provide the right resources, at the right time, to the right patients.

Rich and meaningful data can be found in source clinical documents and records, such as diagnosis, progress notes, pathology reports, radiology reports, lab test results, follow-up notes, images, and flow sheets. These types of records are referred to as "raw clinical data". However, many electronic health records do not include robust structured data fields that permit storage of clinical data in a structured format. Where electronic medical record systems capture clinical data in a structured format, they do so with a primary focus on data fields required for billing operations or compliance with regulatory requirements. The remainder of a patient's record remains isolated, unstructured and inaccessible within text-based or other raw documents, which may even be stored in adjacent systems outside of the formal electronic health record. Additionally, physicians and other clinicians would be overburdened by having to manually record hundreds of data elements across hundreds of discrete data fields.

As a result, most raw clinical data is not structured in the medical record. Hospital systems, therefore, are unable to mine and/or uncover many different types of clinical data in an automated, efficient process. This gap in data accessibility can limit a hospital system's ability to plan for precision medicine care, which in turn limits a clinician's ability to provide such care.

Several software applications have been developed to provide automated structuring, e.g., through natural language processing or other efforts to identify concepts or other medical ontological terms within the data. Like manual structuring, however, many of such efforts remain limited by errors or incomplete information.

Efforts to structure clinical data also may be limited by conflicting information within a single patient's record or among multiple records within an institution. For example, where health systems have structured their data, they may have done so in different formats. Different health systems may have one data structure for oncology data, a different data structure for genomic sequencing data, and yet another different data structure for radiology data. Additionally, different health systems may have different data structures for the same type of clinical data. For instance, one health system may use one EMR for its oncology data, while a second health system uses a different EMR for its oncology data. The data schema in each EMR will usually be different. Sometimes, a health system may even store the same type of data in different formats throughout its organization. Determination of data quality across various data sources is both a common occurrence and challenge within the healthcare industry.

To be useful, disease state, treatment and results data and conclusions based thereon have to be rendered accessible to physicians, researchers and other interested parties. In the case of disease treatments where disease states, treatments, results and conclusions are extremely complicated and nuanced, physician and researcher interfaces have to present massive amounts of information and show many data corollaries and relationships. When massive amounts of information are presented via an interface, interfaces often become extremely complex and intimidating, which can result in misunderstanding and underutilization. What is needed are well designed interfaces that make complex data sets simple to understand and digest. For instance, in the case of disease states, treatments and results, it would be useful to provide interfaces that enable physicians to consider de-identified patient data for many patients where the data is specifically arranged to trigger important treatment and results insights. It would also be useful if interfaces had interactive aspects so that the physicians could use filters to access different treatment and results data sets, again, to trigger different insights, to explore anomalies in data sets, and to better think out treatment plans for their own specific patients.

Disease research is progressing all the time at many hospitals and research institutions where clinical trials are always being performed to test new medications and treatment plans. A patient without other effective treatment options can opt to participate in a clinical trial if the patient's disease state meets trial requirements and if the trial is not yet fully enrolled (such as there is often a limit to the number of patients that can participate in a trial).

At any time there are several thousand clinical trials progressing around the world, and identifying trial options for specific patients can be a daunting endeavor. Matching a patient disease state to a subset of ongoing trials is complicated and time consuming. Paring down matching trials to a best match given location, patient and physician requirements and other factors exacerbates the task of considering trial participation. In addition, considering whether or not to recommend a clinical trial to a specific patient given the possibility of trial treatment efficacy where the treatments are by their very nature experimental, especially in light of specific patient conditions, is a daunting activity that most physicians do not take lightly. It would be advantageous to have a tool that could help physicians identify clinical trial options for specific patients with specific disease states and to access information associated with trial options.

One other problem with current disease treatment planning processes is that it is difficult to integrate new pertinent treatment factors, treatment efficacy data and insights into existing planning databases. In this regard, known treatment planning databases have been developed with a predefined set of factors and insights and changing those databases often requires a substantial effort on the part of a software engineer to accommodate and integrate the new factors or insights in a meaningful way where those factors and insights are correctly correlated with other known factors and insights. In some cases the required substantial effort simply means that the new factor or insight will not be captured in the database or used to affect planning while in other cases the effort means that the new factor or insight is only added to the system at some delayed time required to apply the effort.

One other problem with existing disease treatment efficacy databases and systems is that they are simply incapable of optimally supporting different types of system users. To this end, data access, views and interfaces needed for optimal use are often dependent upon what a system user is using the system for. For instance, physicians often want treatment options, results and efficacy data distilled down to simple recommendations while a researcher often requires much more detailed data access to develop new hypothesis related to disease state, treatment and efficacy relationships. In known systems, data access, views and interfaces are often developed with one consuming client in mind such as, for instance, general practitioners, radiologists, a treatment researcher, etc., and are therefore optimized for that specific system user type which means that the system is not optimized for other user types.

Pharmacogenomics is the study of the role of the human genome in drug response. Aptly named by combining pharmacology and genomics, pharmacogenomics analyzes how the genetic makeup of an individual affects their response to drugs. It deals with the influence of genetic variation on drug response in patients by correlating gene expression pharmacokinetics (drug absorption, distribution, metabolism, and elimination) and pharmacodynamics (effects mediated through a drug's biological targets). Although both terms relate to drug response based on genetic influences, pharmacogenetics focuses on single drug-gene interactions, while pharmacogenomics encompasses a more genome-wide association approach, incorporating genomics and epigenetics while dealing with the effects of multiple genes on drug response. One aim of pharmacogenomics is to develop rational means to optimize drug therapy, with respect to the patients' genotype, to ensure maximum efficiency with minimal adverse effects. Pharmacogenomics and pharmacogenetics may be used interchangeably throughout the disclosure.

The human genome consists of twenty-three pairs of chromosomes, each containing between 46 million and 250 million base pairs (for a total of approximately 3 billion base pairs), each base pair having complementary nucleotides (the pairing that is commonly described with a double helix). For each chromosome, the location of a base pair may be referred to by its locus, or index number for the base pair in that chromosome. Typically, each person receives one copy of a chromosome from their mother and the other copy from their father.

Conventional approaches to bring pharmacogenomics into precision medicine for the treatment, diagnosis, and analysis of diseases include the use of single nucleotide polymorphism (SNP) genotyping and detection methods (such as through the use of a SNP chip). SNPs are one of the most common types of genetic variation. A SNP is a genetic variant that only spans a single base pair at a specific locus. When individuals do not have the same nucleotide at a particular locus, a SNP may be defined for that locus. SNPs are the most common type of genetic variation among people. Each SNP represents a difference of a single DNA building block. For example, a SNP may describe the replacement of the nucleotide cytosine (C) with the nucleotide thymine (T) at a locus.

Furthermore, different nucleotides may exist at the same locus within an individual. A person may have one nucleotide in a first copy of a particular chromosome and a distinct nucleotide in the second copy of that chromosome, at the same locus. For instance, loci in a person's first copy of a chromosome may have this nucleotide sequence— AAGCCTA, and the second copy may have this nucleotide sequence at the same loci—AAGCTTA. In other words, either C or T may be present at the $5^{th}$ nucleotide position in that sequence. A person's genotype at that locus can be described as a list of the nucleotides present at each copy of the chromosome, at that locus. SNPs with two nucleotide options typically have three possible genotypes (a pair of matching nucleotides of the first type, one of each type of nucleotide, and a pair of matching nucleotides of the second type—AA, AB, and BB). In the example above, the three genotypes would be CC, CT, and TT. In a further example, at locus 68,737,131 the rs16260 variant is defined for gene CDH1 (in chromosome 16) where (C;C) is the normal genotype where C is expected at that locus, and (A;A) and (A;C) are variations of the normal genotype.

While SNPs occur normally throughout a person's DNA, they occur almost once in every 1,000 nucleotides on average, which means there are roughly 4 to 5 million SNPs in a person's genome. There have been more than 100 million SNPs detected in populations around the world. Most commonly, these variations are found in the DNA between genes (regions of DNA known as "introns"), where they can act as biological markers, helping scientists locate genes that are associated with disease.

SNPs are not the only genetic variant possible in the human genome. Any deviation in a person's genome sequences when compared to normal, reference genome sequences may be referred to as a variant. In some cases, a person's physical health can be affected by a single variant, but in other cases it is only affected by a combination of certain variants located on the same chromosome. When variants in a gene are located on the same chromosome that means the variants are in the same allele of the gene. An allele may be defined as a continuous sequence of a region of a DNA molecule that has been observed in an individual organism, especially when the sequence of that region has been shown to have variations among individuals. When certain genetic tests, like NGS, detect more than one variant in a gene, it is possible to know whether those variants are in the same allele. Some genetic tests do not have this capability.

Certain groups of variants that exist together in the same chromosome may form a specific allele that is known to alter a person's health. Occasionally, a single allele may not affect a person's health, unless that person also has a specific combination of alleles. Sometimes an allele or allele combination is reported or published in a database or other record with its health implications (for instance, that having the allele or allele combination causes a person to be an ultrafast metabolizer; intermediate metabolizer; or poor metabolizer; etc.). Exemplary records include those from the American College of Medical Genetics and Genomics (ACMG), the Association for Molecular Pathology (AMP), or the Clinical Pharmacogenetics Implementation Consortium (CPIC). These published alleles may each have a designated identifier, and one category of identifiers is the * (star) allele system. For example, for each gene, each star allele may be numbered *1, *2, *3, etc., where *1 is generally the reference or normal allele. As an example, the CYP2D6 gene has over 100 reported variant alleles.

Developed before NGS, microarray assays have been a common genetic test for detecting variants. Microarray assays use biochips with DNA probes bound to the biochip surface (usually in a grid pattern). Some of these biochips are called SNP chips. A solution with DNA molecules from one or more biological samples is introduced to the biochip surface. Each DNA molecule from a sample has a fluorescent dye or another type of dye attached. Often the color of the dye is specific to the sample, and this allows the assay to distinguish between two samples if multiple samples are introduced to the biochip surface at the same time.

If the solution contains a DNA sequence that is complementary to one of the probes affixed to the biochip, the DNA sequence will bind to the probe. After all unbound DNA molecules are washed away, any sample DNA bound to the probe will fluoresce or create another visually detectable signal. The location and sequence of each probe is known, so the location of the visually detectable signal indicates what bound, complementary DNA sequence was present in the samples and the color of the dye indicates from which sample the DNA sequence originated. The probe sequences on the biochip each only contain one sequence, and the probes bind specifically to one complementary sequence in the DNA, meaning that most probes can only detect one type of mutation or genetic variant. This also means that a microarray will not detect a sequence that is not targeted by the probes on the biochip. It cannot be used to find new variants. This is one reason that next generation sequencing is more useful than microarrays.

The fact that a probe only detects one specific DNA sequence means that the microarray cannot determine whether two detected variants are in the same allele unless the loci of the variants are close enough that a single probe can span both loci. In other words, the number of nucleotides between the two variants plus the number of nucleotides within each variant must be smaller than the number of nucleotides in the probe otherwise the microarray cannot detect whether two variants are in the same DNA strand, which means they are in the same allele.

Also, each probe will bind to its complementary sequence within a unique temperature range and range of concentrations of components in the DNA solution introduced to each biochip. Because it is difficult to simultaneously achieve optimal binding conditions for all probes on a microarray (such as the microarrays used in SNP Chips), any DNA from a sample has the potential to hybridize to probes that are not perfectly complementary to the sample DNA sequence and cause inaccurate test results.

Furthermore, disadvantages of microarrays include the limited number of probes present to target biomarkers due to the surface area of the biochip, the misclassification of variants that do not bind to probes as a normal genotype, and the overall misclassification of the genotype of the patient. Due to the limited processing efficiency of SNP chips, conventional microarray approaches are inefficient in detecting biomarkers and their many included variations.

Taqman assays have limitations similar to those of microarrays. If a taqman assay probe is an exact match for a complementary sequence in a DNA molecule from a sample, the DNA molecule gets extended, similar to NGS. However, instead of reporting what the sequence of each nucleotide type is in the DNA extension, the assay only reports whether extension occurred or not. This leads to the same limitations as SNP chips. Other genetic tests, such as dot blots and southern blots, have similar limitations.

Thus, what is needed is a system that is capable of efficiently capturing all treatment relevant data including disease state factors, treatment decisions, treatment efficacy and exploratory factors (such as factors that may have a causal relationship to treatment efficacy) and structuring that data to optimally drive different system activities including memorialization of data and treatment decisions, database analytics and user applications and interfaces. In addition, the system should be highly and rapidly adaptable so that it can be modified to absorb new data types and new treatment and research insights as well as to enable development of new user applications and interfaces optimized to specific user activities.

BRIEF SUMMARY OF THE DISCLOSURE

The present disclosure includes systems and methods for interrogating raw clinical documents for characteristic data.

In a first aspect, a computer program product includes a plurality of microservices for interrogating one or more clinical records according to one or more projects associated with patient datasets, the patient datasets obtained from one or more electronic copies of source documents from the one or more clinical records. The computer program product includes a first microservice for generating a user interface including a first portion displaying one or more of the source documents and, concurrently, a second portion displaying structured patient data fields for entering structured patient data derived from the one or more source documents displayed in the first portion, the structured patient data fields organized into one or more categories, a choice of the one or more categories and their organization defined by a template, wherein the one or more categories include at least cancer diagnosis, staging, tumor size, genetic results, and date of recurrence. A second microservice is provided for validation of abstracted patient data according to one or more validation rules applied to at least one of the categories, validation rules being assigned to the one or more projects, validations being performed on the one or more categories as they are populated. A third microservice is provided for abstraction review performed by an assigned abstractor or an abstraction manager, the abstraction review spanning one or more of the projects.

In a second aspect, a computer program product includes a plurality of microservices for interrogating one or more clinical records according to one or more projects associated with patient datasets, the patient datasets obtained from one or more electronic copies of source documents from the one or more clinical records. The computer program product includes a first microservice for generating a user interface including a first portion displaying one or more of the source documents and, concurrently, a second portion displaying structured patient data fields for entering structured patient data derived from the one or more source documents displayed in the first portion, the structured patient data fields organized into one or more categories, a choice of the one or more categories and their organization defined by a template. A second microservice is provided for validation of abstracted patient data according to one or more validation rules applied to at least one of the categories, validation rules being assigned to the one or more projects, validations being performed on the one or more categories as they are populated. A third microservice is provided for abstraction review performed by an assigned abstractor or an abstraction manager, the abstraction review spanning one or more of the projects.

In either of the first or second aspects, the one or more templates may be determined as a result of an abstractor selection, a selection of the one or more projects, a selection of the one or more documents displayed in the first portion of the user interface, or a machine learning analysis applied to the one or more documents.

In either of the first or second aspects, each template may define one or more subcategories of a category and one or more fields to be abstracted from a source document. A subcategory of the one or more subcategories may include one or more additional subcategories and/or one or more fields. Additionally or alternatively, a category of the one or more categories may include one or more fields. A field may include one or more sets of data values having a data type or one or more data type indicators. Validation of a field may include comparing an abstraction entry to a list of data values selected from the sets of data values or to one of the data type indicators. A data value in at least one field may be obtained from a drop-down menu or obtained via keyed input from a user. Structured patient data also may be entered into the second portion of the user interface as a result of optical character recognition being performed on at least portions of the source documents.

In either of the first or second aspects, the one or more categories of patient data may include at least one of next generation sequencing information, genetic sequencing information, laboratory result information, demographic information, diagnosis information, treatments information, and outcomes information.

In either of the first or second aspects, the one or more validation rules may include applying validations only after an effective date. The one or more validation rules may include one or more logical connectors, one or more subcategories of patient information, and one or more requirements for a field of the one or more subcategories of patient information. The one or more validation rules additionally or alternatively may include a first error descriptor indicating a warning and a second error descriptor indicating an error. A user may be permitted to ignore a warning, but the user interface may prevent submission of a field when a validation rule indicates an error. A number of warnings or errors a user encounters may be recorded as a performance metric for the user.

In either of the first or second aspects, the user interface may provide a summary of errors and warnings upon submission for user review and may submit abstraction results based upon confirmation of submission. Submitting abstraction results may include storing data in a structured format.

In either of the first or second aspects, the user interface may be configured to permit a user to review one or more patients that fail one or more selected validation rule sets.

In either of the first or second aspects, the template may be associated with at least one valueset, each valueset associable to at least one additional template.

In either of the first or second aspects, abstraction review may include assigning overlapping abstraction to more than one abstraction user. Additionally or alternatively, abstraction review may provide all records failing a validation rule to a user. The user may assign an abstraction task to another user to resolve a record failing a validation rule.

In either of the first or second aspects, the second microservice is configured to populate the one or more categories in response to inputs received from an assigned abstractor or an artificial intelligence engine.

In either of the first or second aspects, at least one of the microservices may be targeted to a specific disease state. For example, the categories, sub-categories, or fields are related to at least one of oncology, cardiology, depression, mental health, or other neurological disorders. diabetic disorders, infectious diseases, epilepsy, dermatology, autoimmune diseases, or neurological disorders. Alternatively, each of the microservices may be disease-agnostic.

In either of the first or second aspects, the product may be integrated into an electronic medical records platform. The source documents may include one or more of treatment data including treatment information or resulting data, genetic data, brain scan data, or clinical records including biographical information, patient history, family history, or comorbid conditions. The source documents may include scanned forms and/or handwritten comments.

In either of the first or second aspects, the third microservice may be configured to identify discrepancies between abstraction results from a plurality of abstractors, where a discrepancy score may be a summation of all of the identified discrepancies. The discrepancy score may be compared to a threshold. Source documents corresponding to a discrepancy score below the threshold may be accepted, while source documents corresponding to a discrepancy score above the threshold may be reviewed by an additional abstractor authorized to resolve disputes. The plurality of abstractors may be selected randomly or based on a percentage of each user's expected production. Discrepancies may be weighted based on a type of data that is abstracted and a quantification of the discrepancy.

In either of the first or second aspects, the computer program product may include a fourth microservices configured to ingest new record types in raw data form to a database. The fourth microservice also may be configured to generate an alert indicating that a new record is available for consumption by one or more of the other microservices.

In either of the first or second aspects, the categories may include one or more of demographics, diagnosis, treatments, outcomes, genetic testing, or labs. Subcategories may include one or more of genetic testing or genetic results. Subcategories also may include one or more of a date of testing result, testing provider, date of specimen collection, test method, gene, or result.

In either of the first or second aspects, the computer program product may be dynamically configured. For example, the first microservice may permit a user to add or remove a category or a sub-category from the user interface or to change a template. Similarly, a template may be associated with a validation rule, and the third microservice may be configured to permit a user to add a validation rule.

In either of the first or second aspects, a single template may be used across multiple projects. A single template also may be used for source documents originating from a plurality of different sources. The plurality of different sources may be different institutions, such as different hospitals.

In either of the first or second aspects, a data field may be categorized in a first category for a first project and a second category for a second, different project.

In either of the first or second aspects, the user interface may be configured to present abstraction fields side-by-side with the one or more electronic copies of source documents from which the abstraction fields are obtained. The user interface may provide patient information for one or more patients and/or predictions of patient progression or patient treatment outcomes to a user. The user interface also may provide predictions of patient treatment progression or patient treatment outcome to a physician.

Some embodiments of the present disclosure provide a method for validating abstracted patient data. The method can include receiving original patient data. The method can further include displaying, via a user interface, the original patient data and a data entry form. Additionally, the method can include receiving a first data entry in a first data entry field corresponding to the data entry form, the first data entry based on the original patient data. The method can include identifying, based on the first data entry, an expected second data entry corresponding to a second data entry field. The method can further include displaying, via the user interface, a warning indicator corresponding to the expected second data entry.

Some embodiments of the present disclosure provide a method for generating abstracted patient data. The method can include receiving original patient data corresponding to a patient. The method can further include identifying an assigned project for the patient, and identifying a data template corresponding to the assigned project. Additionally, the method can include generating a data entry form based on the data template, the data entry form having a plurality of data entry fields. The method can include displaying, via a user interface, the original patient data and the data entry form. The method can further include populating the plurality of data entry fields based on the original patient data.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE DRAWINGS

FIG. 2 is another image of an example graphical user interface (GUI), according to aspects of the present disclosure;

FIG. 3 is another image of an example graphical user interface (GUI), according to aspects of the present disclosure;

FIG. 4 is another image of an example graphical user interface (GUI), according to aspects of the present disclosure;

FIG. 5 is another image of an example graphical user interface (GUI), according to aspects of the present disclosure;

FIG. 6 is another image of an example graphical user interface (GUI), according to aspects of the present disclosure;

FIG. 7 is another image of an example graphical user interface (GUI), according to aspects of the present disclosure;

FIG. 8 is another image of an example graphical user interface (GUI), according to aspects of the present disclosure;

FIG. 9 is another image of an example graphical user interface (GUI), according to aspects of the present disclosure;

FIG. 12 is another image of an example graphical user interface (GUI), according to aspects of the present disclosure;

FIG. 14 is another image of an example graphical user interface (GUI), according to aspects of the present disclosure;

FIG. 15 is another image of an example graphical user interface (GUI), according to aspects of the present disclosure;

FIG. 16 is another image of an example graphical user interface (GUI), according to aspects of the present disclosure;

FIG. 17 is another image of an example graphical user interface (GUI), according to aspects of the present disclosure;

FIG. 18 is another image of an example graphical user interface (GUI), according to aspects of the present disclosure;

FIG. 19 is another image of an example graphical user interface (GUI), according to aspects of the present disclosure;

FIG. 20 is another image of an example graphical user interface (GUI), according to aspects of the present disclosure;

FIG. 22 is another image of an example graphical user interface (GUI), according to aspects of the present disclosure;

FIG. 23 is another image of an example graphical user interface (GUI), according to aspects of the present disclosure;

FIG. 24 is another image of an example graphical user interface (GUI), according to aspects of the present disclosure;

FIG. 25 is another image of an example graphical user interface (GUI), according to aspects of the present disclosure;

FIG. 26 is another image of an example graphical user interface (GUI), according to aspects of the present disclosure;

FIG. 27 is another image of an example graphical user interface (GUI), according to aspects of the present disclosure;

FIG. 28 is another image of an example graphical user interface (GUI), according to aspects of the present disclosure;

FIG. 29 is another image of an example graphical user interface (GUI), according to aspects of the present disclosure;

FIG. 30 is another image of an example graphical user interface (GUI), according to aspects of the present disclosure;

Figure 31:
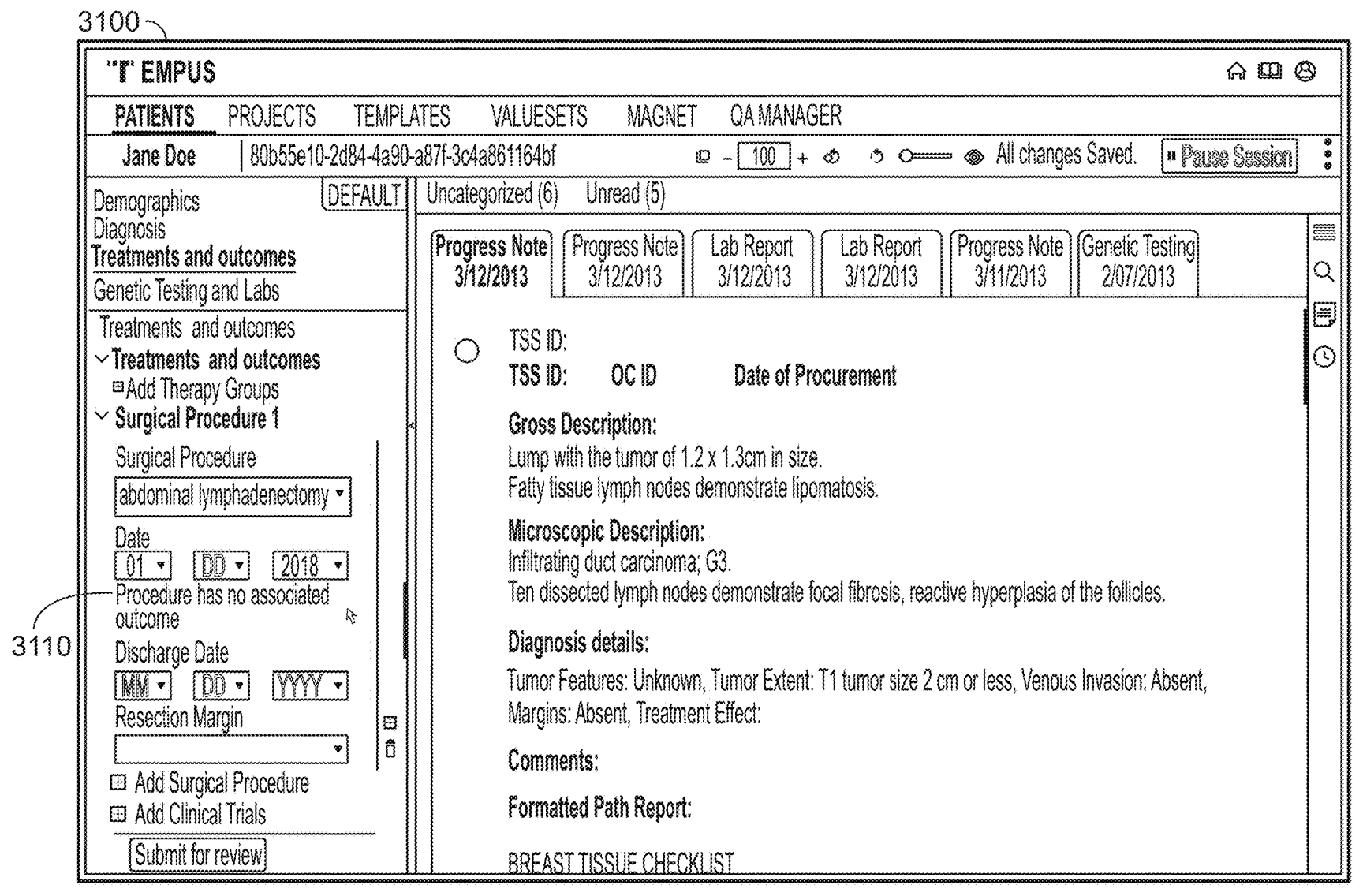

FIG. 31 is another image of an example graphical user interface (GUI), according to aspects of the present disclosure;

Figure 32:
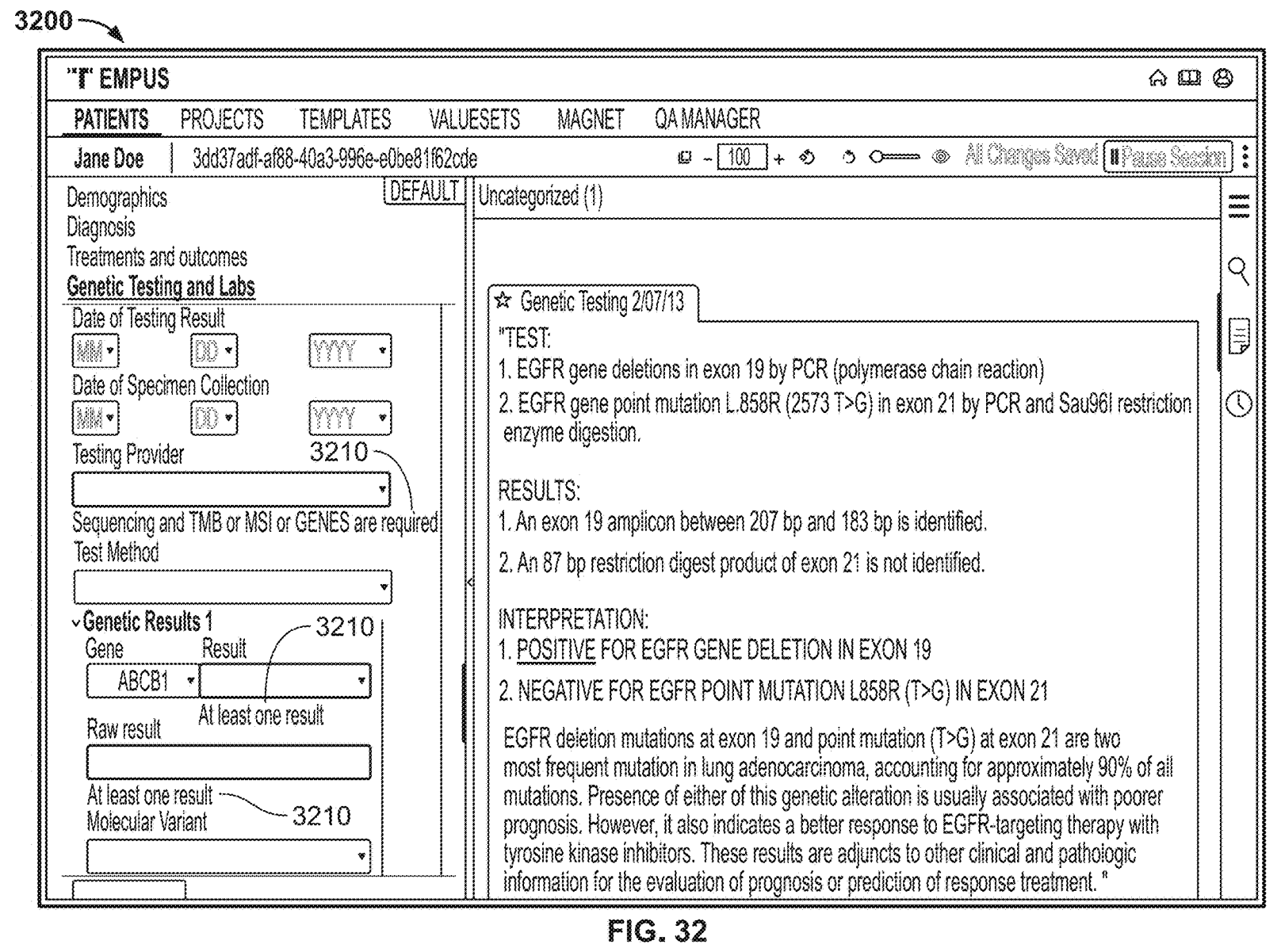

FIG. 32 is another image of an example graphical user interface (GUI), according to aspects of the present disclosure;

FIG. 33 is another image of an example graphical user interface (GUI), according to aspects of the present disclosure;

FIG. 34 is another image of an example graphical user interface (GUI), according to aspects of the present disclosure;

FIG. 35 is another image of an example graphical user interface (GUI), according to aspects of the present disclosure;

FIG. 36 is another image of an example graphical user interface (GUI), according to aspects of the present disclosure;

FIG. 37 is another image of an example graphical user interface (GUI), according to aspects of the present disclosure;

FIG. 38 is another image of an example graphical user interface (GUI), according to aspects of the present disclosure;

FIG. 39 is another image of an example graphical user interface (GUI), according to aspects of the present disclosure;

FIG. 40 is another image of an example graphical user interface (GUI), according to aspects of the present disclosure;

FIG. 41 is another image of an example graphical user interface (GUI), according to aspects of the present disclosure;

FIG. 42 is another image of an example graphical user interface (GUI), according to aspects of the present disclosure;

FIG. 43 is another image of an example graphical user interface (GUI), according to aspects of the present disclosure;

FIG. 45 is another image of an example graphical user interface (GUI), according to aspects of the present disclosure;

FIG. 48 is another image of an example graphical user interface (GUI), according to aspects of the present disclosure;

FIG. 49 is another image of an example graphical user interface (GUI), according to aspects of the present disclosure;

Figure 51:
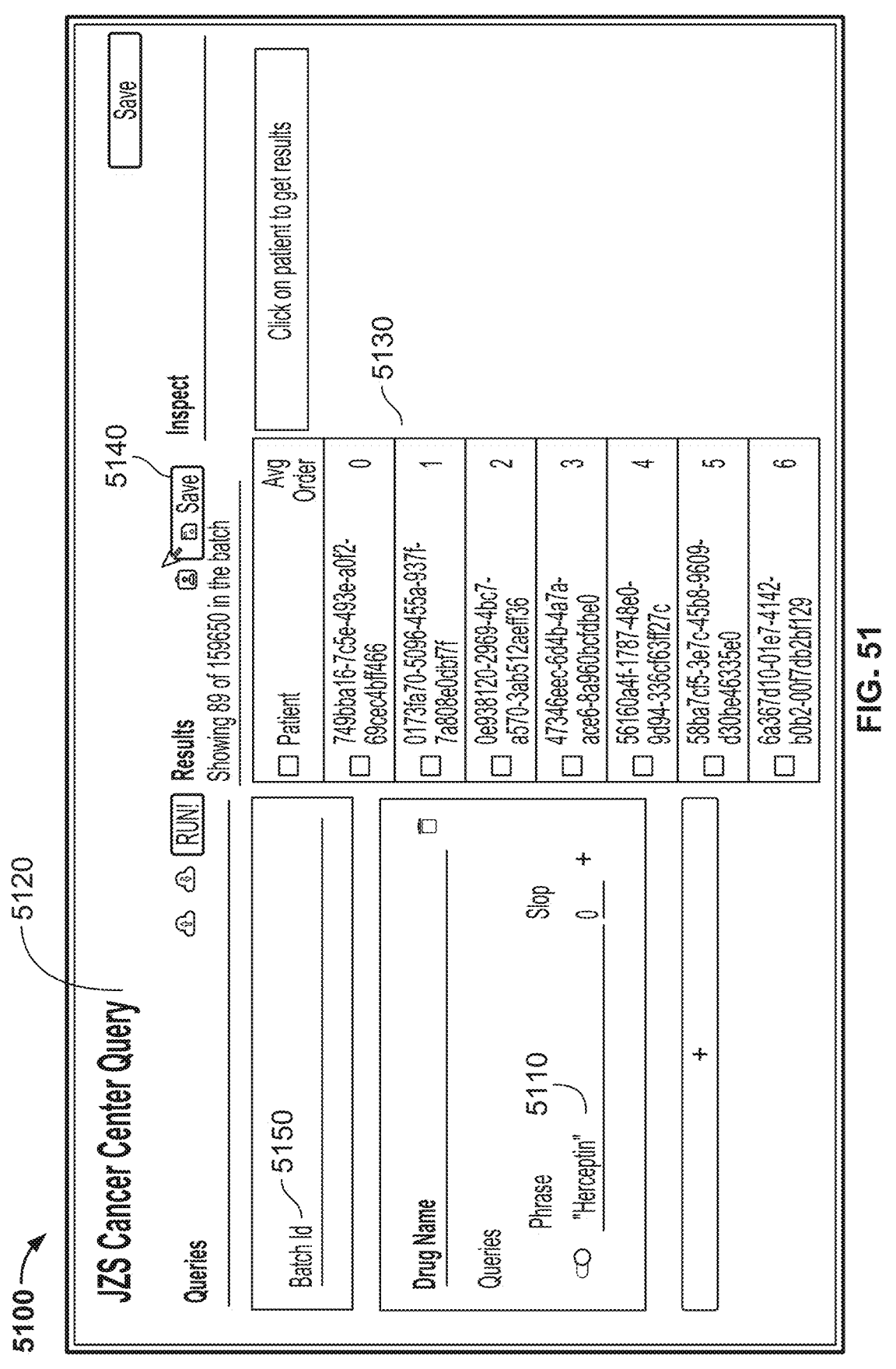

FIG. 51 is another image of an example graphical user interface (GUI), according to aspects of the present disclosure;

FIG. 52 is another image of an example graphical user interface (GUI), according to aspects of the present disclosure;

FIG. 53 is another image of an example graphical user interface (GUI), according to aspects of the present disclosure;

FIG. 54 is another image of an example graphical user interface (GUI), according to aspects of the present disclosure;

Figure 55:
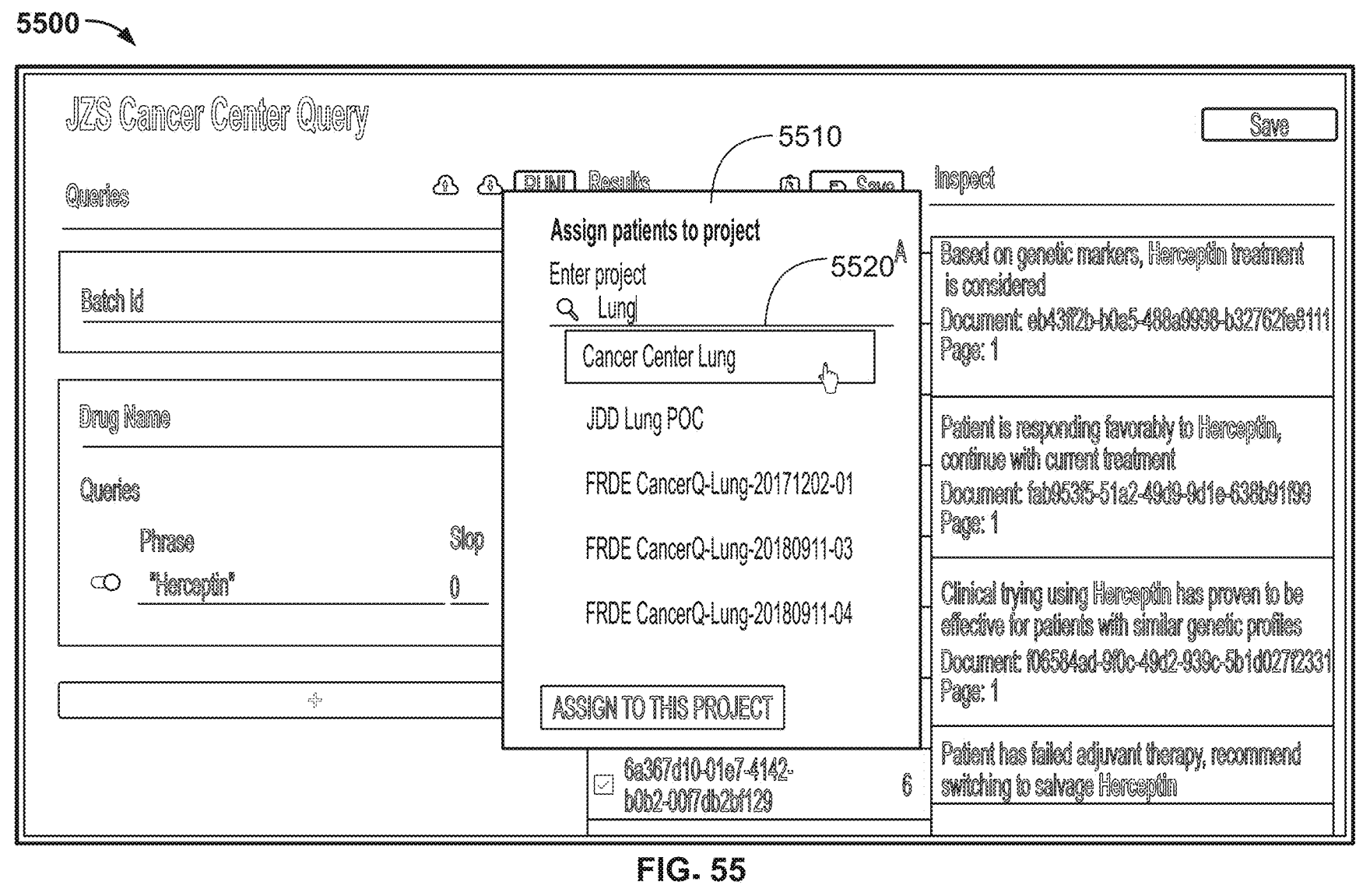

FIG. 55 is another image of an example graphical user interface (GUI), according to aspects of the present disclosure;

FIG. 56 is another image of an example graphical user interface (GUI), according to aspects of the present disclosure;

FIG. 57 is another image of an example graphical user interface (GUI), according to aspects of the present disclosure;

FIG. 58 is another image of an example graphical user interface (GUI), according to aspects of the present disclosure;

FIG. 59 shows an exemplary user interface that a clinical data analyst may utilize to structure clinical data from raw clinical data;

FIG. 60 depicts one example of EMR-extracted structured data that includes a payload of diagnosis-related data;

FIG. 61 depicts one example of EMR-extracted structured data that includes a payload of medication-related data;

FIG. 62 depicts a user interface that may be used by a conflict resolution user when a complex disagreement is identified for a patient record;

FIG. 63 depicts a user interface that may be used by a conflict resolution user when a more straightforward disagreement is identified for a patient record;

FIG. 64 depicts a list of test suites within a "demographics" root level category;

FIG. 65 depicts an exemplary test suite for determining sufficiency of a structured and/or abstracted instance of genetic testing;

FIG. 66 depicts a second exemplary test suite for determining sufficiency of a structured and/or abstracted instance of genetic testing;

Figure 73:
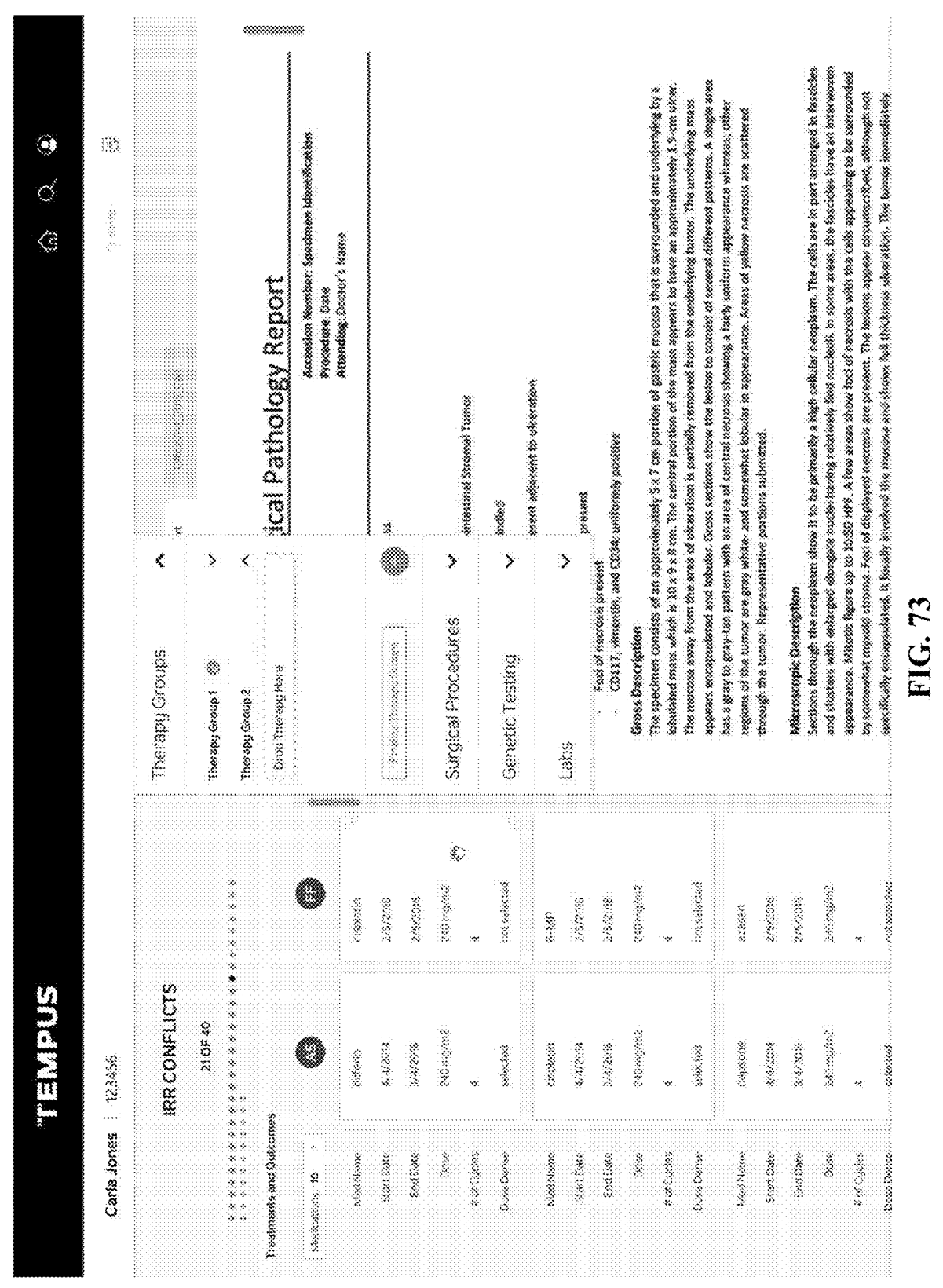

FIG. 73 depicts a second example of various metrics or reports generated by the present system;

Figure 1:
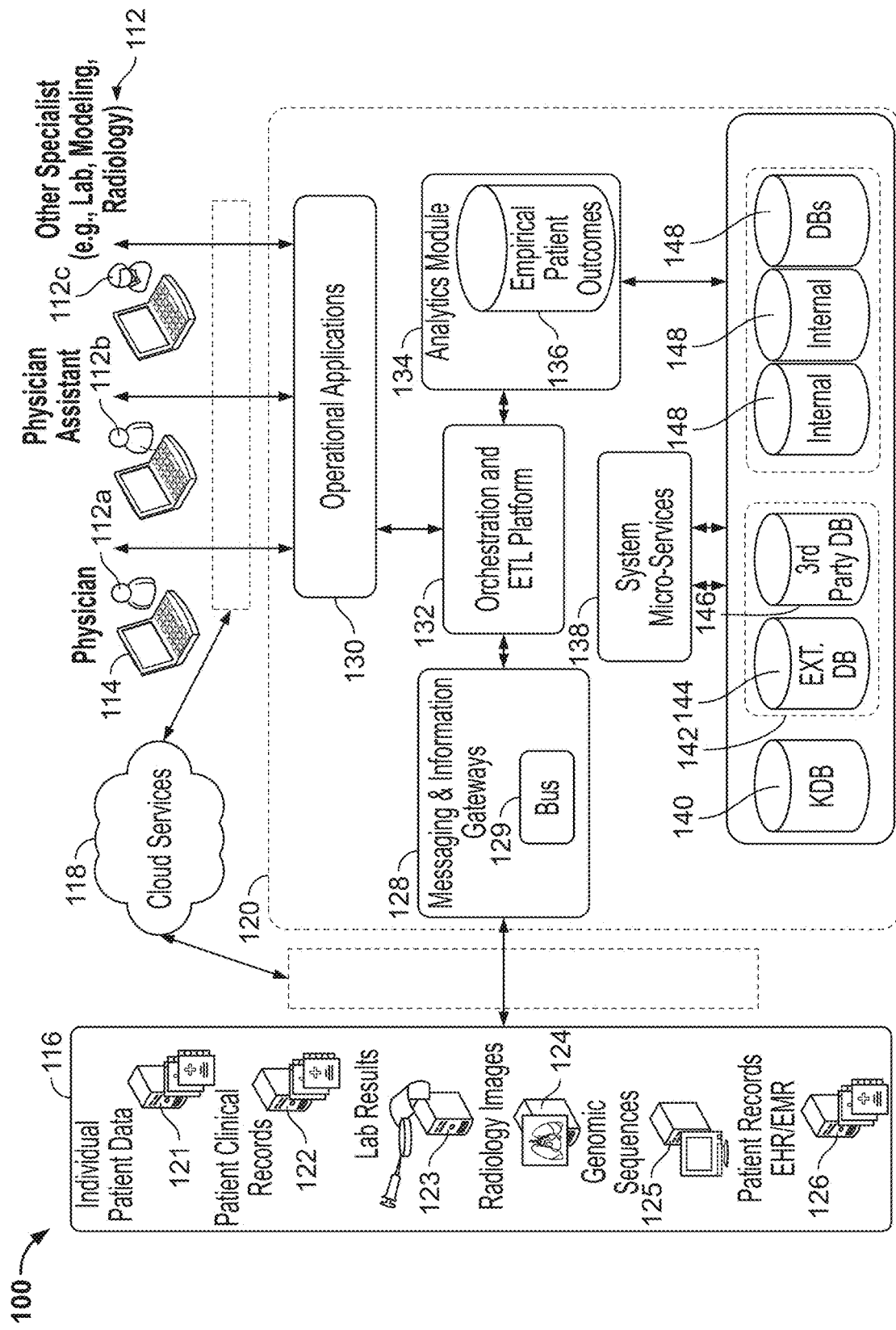
FIG. 1 is a block diagram of a data-based healthcare system, according to aspects of the present disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE DISCLOSURE

The various aspects of the subject invention are now described with reference to the annexed drawings. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

Furthermore, the disclosed subject matter may be implemented as a system, method, apparatus, or article of manufacture using programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (such as hard disk, floppy disk, magnetic strips), optical disks (such as compact disk (CD), digital versatile disk (DVD)), smart cards, and flash memory devices (such as card, stick). Additionally it should be appreciated that a carrier wave can be employed to carry computer-readable electronic data such as those used in transmitting and receiving electronic mail or in accessing a network such as the Internet or a local area network (LAN). Transitory computer-readable media (carrier wave and signal based) should be considered separately from non-transitory computer-readable media such as those described above. Of course, those skilled in the art will recognize many modifications may be made to this configuration without departing from the scope or spirit of the claimed subject matter.

Unless indicated otherwise, while the disclosed system is used for many different purposes (such as data collection, data analysis, data display, treatment, research, etc.), in the interest of simplicity and consistency, the overall disclosed system will be referred to hereinafter as "the system."

The methods and systems described herein may be implemented for any disease state by configuring the templates, validation rule sets, and value sets to reference fields and structured data particular to each disease state or widely encompass all disease states at once. Disease states may include oncology, cardiology, depression, mental health or other neurological disorders, diabetic disorders, infectious disease, epilepsy, dermatology, or autoimmune diseases, wherein a disease state may reflect the presence or absence of disease in a patient. Specific configurations of the methods and systems herein are described broadly in some aspects such as Laboratory results, and specifically to the disease state of cancers in some aspects such as diagnosis, treatments, and outcomes. It should be understood that the Figures and Descriptions herein are generally configurable to each disease state in turn or as a whole by adding extra disease state templates, validations rule sets, and value sets. Furthermore, aspects of QA review and abstraction review may operate agnostic to the disease state the methods and systems target.

The methods and systems described herein may be used on information generated from NGS techniques. The field of NGS for genomics is new and faces significant challenges in managing relations between sequencing, bioinformatics, variant calling, analysis, and reporting data. NGS involves using specialized equipment such as a next generation gene sequencer, which is an automated instrument that determines the order of nucleotides in DNA and RNA. The instrument reports the sequences as a string of letters, called a read, which the analyst may compare to one or more reference genomes of the same genes. A reference genome may be compared to a library of normal and variant gene sequences associated with certain conditions. With no settled NGS standards, different NGS providers have different approaches for sequencing patient genomics; and, based on their sequencing approaches, generate different types and quantities of genomics data to share with physicians, researchers, and patients. Different genomic datasets exacerbate the task of discerning and, in some cases, render it impossible to discern, meaningful genetics-treatment efficacy insights as required data is not in a normalized form, was never captured or simply was never generated. Extracted DNA from blood or saliva samples are single or paired-end sequenced using an NGS platform, such as a platform offered by Illumina.

The results of sequencing (herein, the "raw sequencing data") may be passed through a bioinformatics pipeline where the raw sequencing data is analyzed. After sequencing information is run through the bioinformatics pipeline, it may be evaluated for quality control, such as through an automated quality control system. If the sample does not pass an initial quality control step, it may be manually reviewed. If the sample passes an automated quality control system or is manually passed, an alert may be published to a message bus that is configured to listen for messages from quality control systems. This message may contain sample identifiers, as well as the location of BAM files. A BAM file (.bam) is the binary version of a SAM file. A SAM file (.sam) is a tab-delimited text file that contains sequence alignment data (such as the raw sequencing data). When a message notifying the topic is received, a service may be triggered to evaluate the sequencing data for pharmacogenomics factors.

The bioinformatics pipeline may receive the raw sequencing results and process them to identify genetic variants that are expressed in the patient's DNA or RNA. An identified variant may be referred to as a variant call. Once a variant has a sufficient number of reads from the raw sequencing results to qualify as a variant call, a variant characterization may be performed on that variant call. Variant characterization may include searching published variant datasets identifying variants of pharmacogenomic importance, searching FDA publications on therapies and their targeted variants, or comparing the variant calls to an internally curated list of variants having pharmacogenomic importance. Any variant calls with pharmacogenomic importance may be flagged for inclusion in a report, such as the reports described in more detail below.

A knowledge database may be generated for accumulating a cohort of patient NGS results and clinical information. The accumulated patient information may be analyzed to identify insights such as potential biomarkers or trends in pharmacogenomics.

The analytic power of NGS stands out above conventional methods of processing genetic variants or alleles which have pharmacogenetic importance. Because the entirety of the normal human genome may be referenced for each of the targeted genes (described in more detail below), NGS may identify previously unobserved variant calls even if the variant was not targeted by the NGS panel. For example, if the normal genome is ATTACCA for a given region of the chromosome, but an untargeted and/or previously undocumented variant exists such that a variant sequence is identified as ATTATCA in that same region, an allele mismatch indicating detection of a new allele spanning that region may be detected merely from the absence of an expected variant call. For example, alleles may be identified from a sequence of nucleotides that match the normal sequence, a sequence of nucleotides that match the sequence of any known allele variation from normal, or by identifying a new sequence which is not a match to any of the known alleles.

Furthermore, because NGS probe reads include the sequence of the DNA molecule that extended from each probe and not just the probe, probe reads from upstream in a DNA molecule which also encompass an untargeted downstream variant may be reported by the NGS sequencer. Confirmed detection of an untargeted variant may be made after analysis in the bioinformatics pipeline, based upon new research or published data. Additionally, sequence coverage over the whole genome allows for research to be performed across aggregated sequencing results and enables the identification of new biomarkers which were previously unknown. An exemplary system that provides a foundation to capture the above benefits, and more, is described below.

System Overview

The present architecture is designed such that system processes may be compartmentalized into loosely coupled and distinct micro-services for defined subsets of system data, may generate new data products for consumption by other micro-services, including other system resources, and enables maximum system adaptability so that new data types as well as treatment and research insights can be rapidly accommodated. Accordingly, because micro-services operate independently of other system resources to perform defined processes where development constraints relate to system data consumed and data products generated, small autonomous teams of scientists and software engineers can develop new micro-services with minimal system constraints that promote expedited service development.

This system enables rapid changes to existing micro-services as well as development of new micro-services to meet any data handling and analytical needs. For instance, in a case where a new record type is to be ingested into an existing system, a new record ingestion micro-service can be rapidly developed resulting in that addition of a new record in a raw data form to a system database as well as a system alert notifying other system resources that the new record is available for consumption. Here, the intra-micro-service process is independent of all other system processes and therefore can be developed as efficiently and rapidly as possible to achieve the service specific goal. As an alternative, an existing record ingestion micro-service may be modified independent of other system processes to accommodate some aspect of the new record type. The micro-service architecture enables many service development teams to work independently to simultaneously develop many different micro-services so that many aspects of the overall system can be rapidly adapted and improved at the same time. In some elements, a microservice architecture may include one or more microservices each targeted to a specific disease state.

A messaging gateway may receive data files and messages from micro-services, glean metadata from those files and messages and route those files and messages on to other system components including databases, other micro-services, and various system applications. This enables the micro-services to poll their own messages as well as incoming transmissions (point-to-point) or bus transmissions (broadcast to all listeners on the bus) to identify messages that will start or stop the micro-services.

Referring now to the figures that accompany this written description and more specifically referring to FIG. 1, the present disclosure will be described in the context of an exemplary disclosed system 100 where data is received at a server 120 from many different data sources (such as database 142, clinical record 122, and micro-services (not shown)). In some aspects, the server 120 can store relevant data, such as at database 136, which is shown to include empirical patient outcomes. The server 120 can manipulate and analyze available data in many different ways via an analytics module 134. Further, the analytics module 134 can condition or "shape" the data to generate new interim data or to structure data in different structured formats for consumption by user application programs and to then drive the user application programs to provide user interfaces via any of several different types of user interface devices. While a single server 120 and a single internal database 136 are shown in FIG. 1 in the interest of simplifying this explanation, it should be appreciated that in most cases, the system 100 can include a plurality of distributed servers and databases that are linked via local and/or wide area networks and/or the Internet or some other type of communication infrastructure. An exemplary simplified communication network is labeled 118 in FIG. 1. Network connections can be any type, including hard wired, wireless, etc., and may operate pursuant to any suitable communication protocols. Furthermore, the network connections may include the communication/messaging gateway/bus that enables microservices file and message transfer according to the above system.

The system 100 enables many different system clients to securely link to server 120 using various types of computing devices to access system application program interfaces optimized to facilitate specific activities performed by those clients. For instance, in FIG. 1 a provider 112 (such as a physician, researcher, lab technician, etc.) is shown using a display device 114 (such as a laptop computer, a tablet, a smart phone, etc.) to link to server 120. In some aspects, the display device 114 can include other types of personal computing devices, such as, virtual reality headsets, projectors, wearable devices (such as a smart watch).

In at least some embodiments, when a physician uses system 100, a physician's user interface (such as on display device 114) is optimally designed to support typical physician activities that the system supports including activities geared toward patient treatment planning. Similarly, when a researcher (such as a radiologist) uses system 100, user interfaces optimally designed to support activities performed by those system clients are provided. In other embodiments, the physician's user interface, software, and one or more servers are implemented within one or more microservices. Additionally, each of the discussed systems and subsystems for implementing the embodiments described below may additionally be prescribed to one or more micro-systems.

System specialists (such as employees that control/maintain overall system 100) also use interface computing devices to link to server 120 to perform various processes and functions. For example, system specialists can include a data abstractor, a data sales specialist, and/or a "general" specialist (such as a "lab" specialist). Different specialists will use system 100 to perform many different functions, where each specialist requires specific skill sets needed to perform those functions. For instance, data abstractor specialists are trained to ingest clinical records from various sources (such as clinical record 122) and convert that data to normalized and system optimized structured data sets. A lab specialist is trained to acquire and process patient and/or tissue samples to generate genomic data, grow tissue, treat tissue and generate results. Other specialists are trained to assess treatment efficacy, perform data research to identify new insights of various types and/or to modify the existing system to adapt to new insights, new data types, etc. The system interfaces and tool sets available to provider specialists are optimized for specific needs and tasks performed by those specialists.

Referring again to FIG. 1, server 120 is shown to receive data from several sources. According to some aspects, clinical trial data can be provided to server 120 from database 142. Further, patient data can be provided to server 120. As shown, a patient 116 has corresponding data from multiple sources (such as lab results 123 will be furnished from a laboratory or technician, imaging data 124 will be furnished from a radiologist, etc.). For simplicity, this is representatively shown in FIG. 1 as individual patient data 121. In some aspects, individual patient data 121 includes clinical record(s) 122, lab results 123, and/or imaging data 124. Further, in some aspects, clinical record(s) 122 may include longitudinal data, which is data collected at multiple time points during the course of the patient's treatment.

The individual patient data 121 can be provided to server 120 by, for example, a data abstractor specialist (as described above). Alternatively, electronic records can be automatically transferred to server 120 from various facilities and practitioners, where appropriate. As shown in FIG. 1, patient data communicated to server 120 can include, but is not limited to, treatment data (such as current treatment information and resulting data), genetic data (such as RNA, DNA data), brain scans (such as PET scans, CT, MM, etc.), and/or clinical records (such as biographical information, patient history, family history, comorbid conditions, etc.).

Still referring to FIG. 1, server 120 is shown to include analytics module 134, which can analyze data from database 136 (empirical patient outcomes), and individual patient data 121. Database 136 can store empirical patient outcomes for a large number of patients suffering from the same or similar disease as patient 116. For example, "individual patient data" for numerous patients can be associated with each respective treatment and treatment outcomes, and subsequently stored in database 136. As new patient data and/or treatment data becomes available, database 136 can be updated. As one example, provider 112 may suggest a specific treatment for patient 116, and individual patient data 121 may then be included in database 136.

Analytics module 134 can, in general, use available data to indicate a diagnosis, predict progression, predict treatment outcomes, and/or suggest an optimized treatment plan (such as a medication type, an available clinical trial) based on the specific disease state of each patient. Exemplary analytics may include machine learning algorithms or neural networks. A machine learning algorithm (MLA) or a neural network (NN) may be trained from a training data set. For a disease state, an exemplary training data set may include the clinical and molecular details of a patient such as those curated from the Electronic Health Record or genetic sequencing reports. MLAs include supervised algorithms (such as algorithms where the features/classifications in the data set are annotated) using linear regression, logistic regression, decision trees, classification and regression trees, Nave Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where certain features/classifications in the data set are annotated) using generative approach (such as mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, long short term memory networks, or other neural models where the training data set includes a plurality of samples and RNA expression data for each sample. While MLA and neural networks identify distinct approaches to machine learning, the terms may be used interchangeably herein. Thus, a mention of MLA may include a corresponding NN or a mention of NN may include a corresponding MLA.

Training may include identifying common clinical traits or genetic traits that patients of the overall cohort or patient database may exhibit, labeling these traits as they occur in patient records, and training the MLA to identify patterns in the outcomes of patients based on their treatments as well as their clinical and genetic information. Outputs from analytics module 134 can be provided to display device 114 via communication network 118. Further, provider 112 can input additional data via display device 114 (such as a prescribed treatment), and the data can be transmitted to server 120.

Display device 114 can provide a graphical user interface (GUI) for provider 112. The GUI can, in some aspects, be interactive and provide both comprehensive and concise data to provider 112. As one example, a GUI can include intuitive menu options, selectable features, color and/or highlighting to indicate relative importance of data, and sliding-scale timelines for the viewing of disorder progression. The GUI can be tailored to the type of provider, or even customized for each individual user. For example, a physician can change a default GUI layout based on individual preferences.

Figure 58:
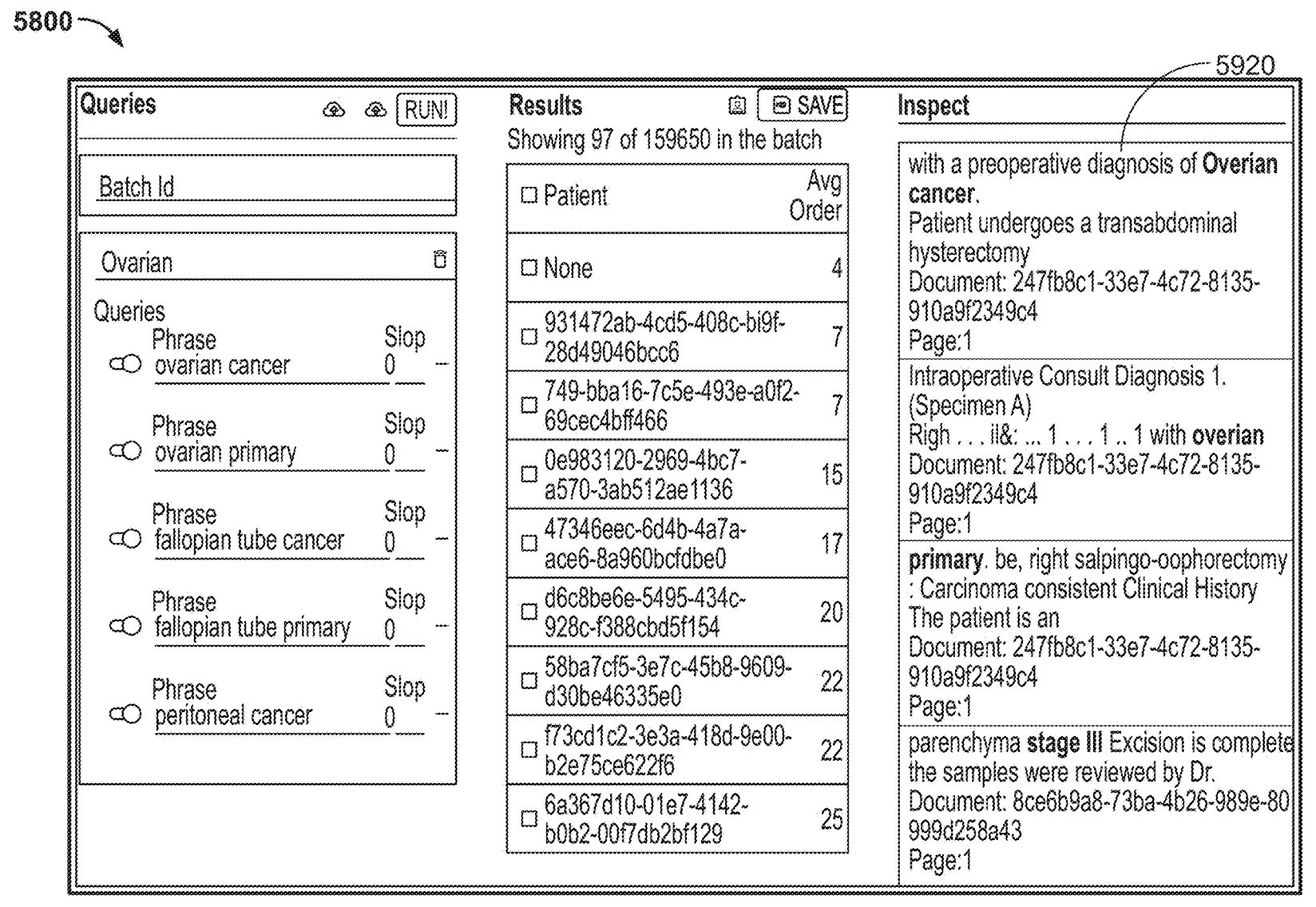

Further aspects of the disclosed system are described in detail with respect to FIGS. 2-58. In particular, an interactive GUI that can be displayed on display device 114, is shown and described.

Graphical User Interface

In some aspects, a graphical user interface (GUI) can be included in system 100. Advantageously, the GUI can provide a single source of information for providers, while still encompassing all necessary and relevant data. This can ensure efficient analysis, searching, and summary of health data. System specialists (e.g., data abstractors), can input patient health data into system 100 via the GUI. For instance, a data abstractor can ingest clinical records from various sources (such as clinical record 122) and convert that data to normalized and system optimized structured data sets. An exemplary GUI is shown and described with respect to FIGS. 2-58.

In some embodiments, system 100 can query relevant data sets. As additional source documents are provided to the system 100, quick search functionality and document management/indexing can improve user interaction with the system 100, as well as limit the amount of manual review and/or searching that occurs. In some embodiments, raw clinical documents and data can be injected into the system 100. A workflow management system/software can be configured to pull in new data and documents, according to some embodiments.

FIG. 2 is a graphical user interface (GUI) 200 that can be implemented in system 100 to enable clinical data structuring and abstraction work on a large scale. In some embodiments, GUI 200 can include several modules as part of a workflow management system. In particular, GUI 200 can include a "Patients" module, a "Projects" module, a "Templates" module, a "Valuesets" module, a "Magnet" module, a "QA Manager" module, and/or a "Validations Manager" module. The modules shown via GUI 200 can communicate data with one another (e.g., patient data, system rules regarding data input, etc.). In one embodiment, the GUI 200 may be created for a single project, for example, when the GUI 200 is only used for one client or for one ongoing project. In examples where the GUI does not have more than one project, the projects module may not be displayed as the entire GUI may be directed to the single project. Additionally, all attributes associated with projects may be further construed as associated with the single project. In yet another embodiment, projects may be associated with a disease state and a respective set of templates, validation rule sets, and value sets.

Referring broadly to FIGS. 2-7, GUIs 200-700 show details corresponding to the "Patients" module. In some embodiments, a data abstractor can use GUI 200 to enter patient health data from raw third party data. As shown in FIG. 2, GUI 200 can provide a split view, with a first panel 210 configured to accept input data from a user (e.g., data abstractor), and a second panel 220 configured to display raw documents corresponding to a patient. In some embodiments, for example, documents can include scanned forms and/or handwritten comments from a provider. Additionally, documents can include third party genetic sequencing reports. As shown by FIG. 2, the first panel 210 can include a data section corresponding to genetic testing and labs, with a plurality of data entry fields available. The first panel 210 is selectable by the user, so that different data fields are displayed depending on the item selected from the first panel 210. For instance, as shown in FIG. 2, the "Genetic Testing and Labs" item has been selected, and so the data fields for Genetic Testing and Labs are displayed, such as date of testing results, testing provider, date of specimen collection, test method, results, and so forth. Each data entry field may have a drop-down menu that lists a plurality of options for the user to select. For instance, "FISH (Fluorescence in situ hybridization)" has been selected in the "Test Method" field in FIG. 2. Other options may be selected from a drop-down menu that has been populated with different test methods. Similarly, the other data fields may be populated with lists. Different types of user interface elements may be utilized in the first panel 210, such as expansion lists (indicated in first panel 210 by a plus sign within a square), dropdown lists (indicated in first panel 210 by a rectangular box with a downward pointing triangular arrow on the right-hand side), free text boxes, and other input elements from the user interface arts.

The GUI may be arranged so that the first panel 210 remains on the screen while the user views different original medical records. Tabs for example original medical records are shown in FIG. 2, namely, a pathology report, a progress note, a first lab report, a second lab report, and a progress note. Each tab may also indicate the date of the record, as is shown in FIG. 2. The pathology report is displayed; however, the user may select one of the other records to display by selecting (via mouse click or other known methods) its associated tab. Selecting a different record while keeping the first panel 210 on the screen allows the user to more easily develop a comprehensive set of structured data about a patient based on review of multiple medical records.

Figure 3:
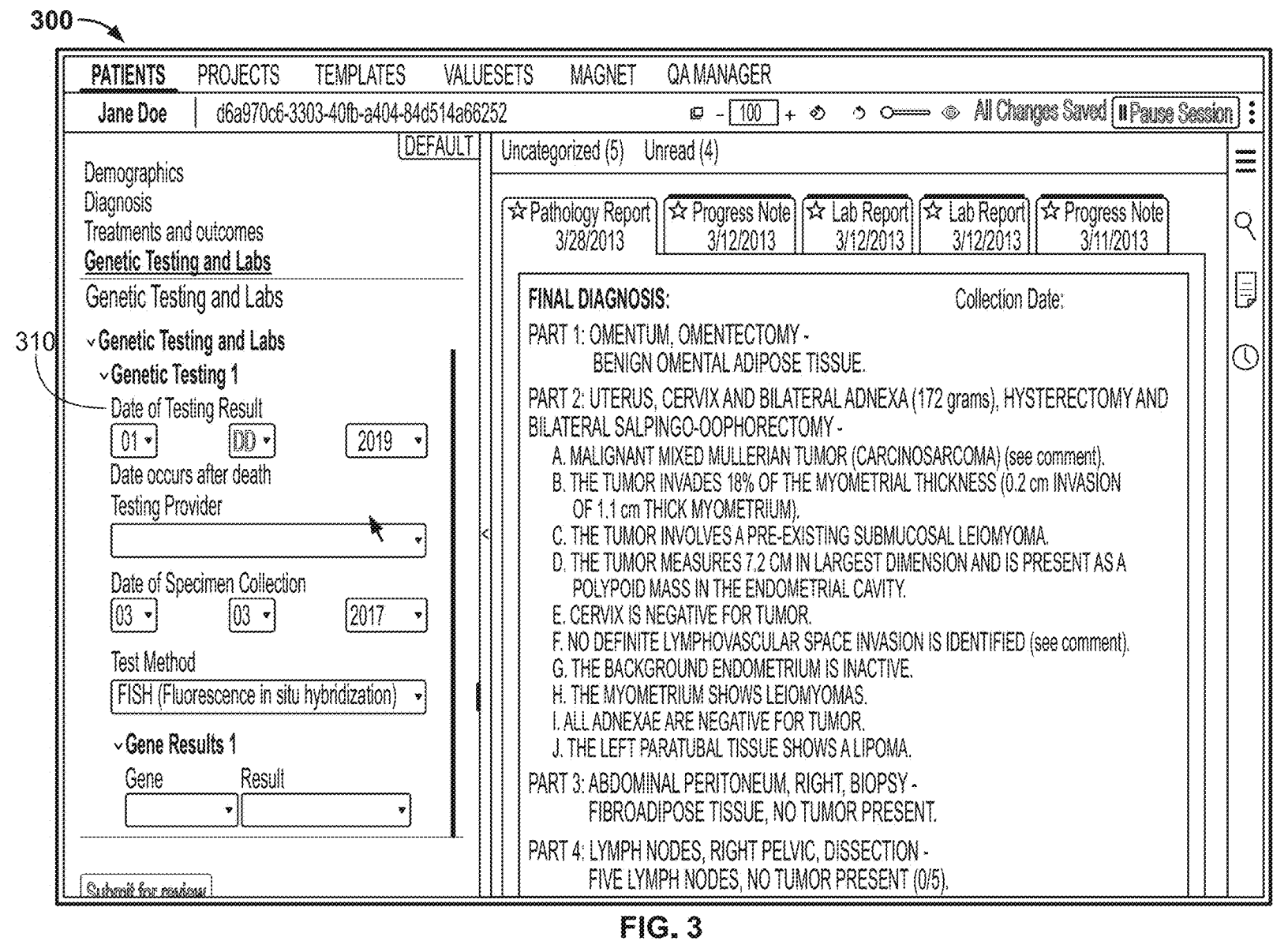

In some embodiments, system 100 (via GUI 200) can include two warning modes with respect to data entry. Colored text and/or a colored outline corresponding to the text field can provide a visual indication of a warning to the user. A first warning mode can be a "soft" warning mode, which can correspond to a first color indicator (e.g., yellow). A soft warning may permit the user to submit the data as-is, but can still provide an indication of sub-optimal data entry. A second warning mode can be a "hard" warning mode, which can correspond to a second color indicator (e.g., red). A hard warning may prevent the user from submitting the data as-is, and additional data or revised data may be required before system 100 allows the user to continue with submission. Soft and Hard warnings may be tracked and reported on an abstraction user by user basis for QA tracking with respect to users. As shown by FIG. 3, for example, a hard warning 310 indicates that the entered "date of testing result" occurs after the instant patient's date of death. Accordingly, a data abstractor can be prevented from submitting this patient's data, until the "date of testing result" warning is reconciled. The warning modes may be designed in advance of a user operating the GUI in order to abstract health information from an original medical record.

Figure 4:
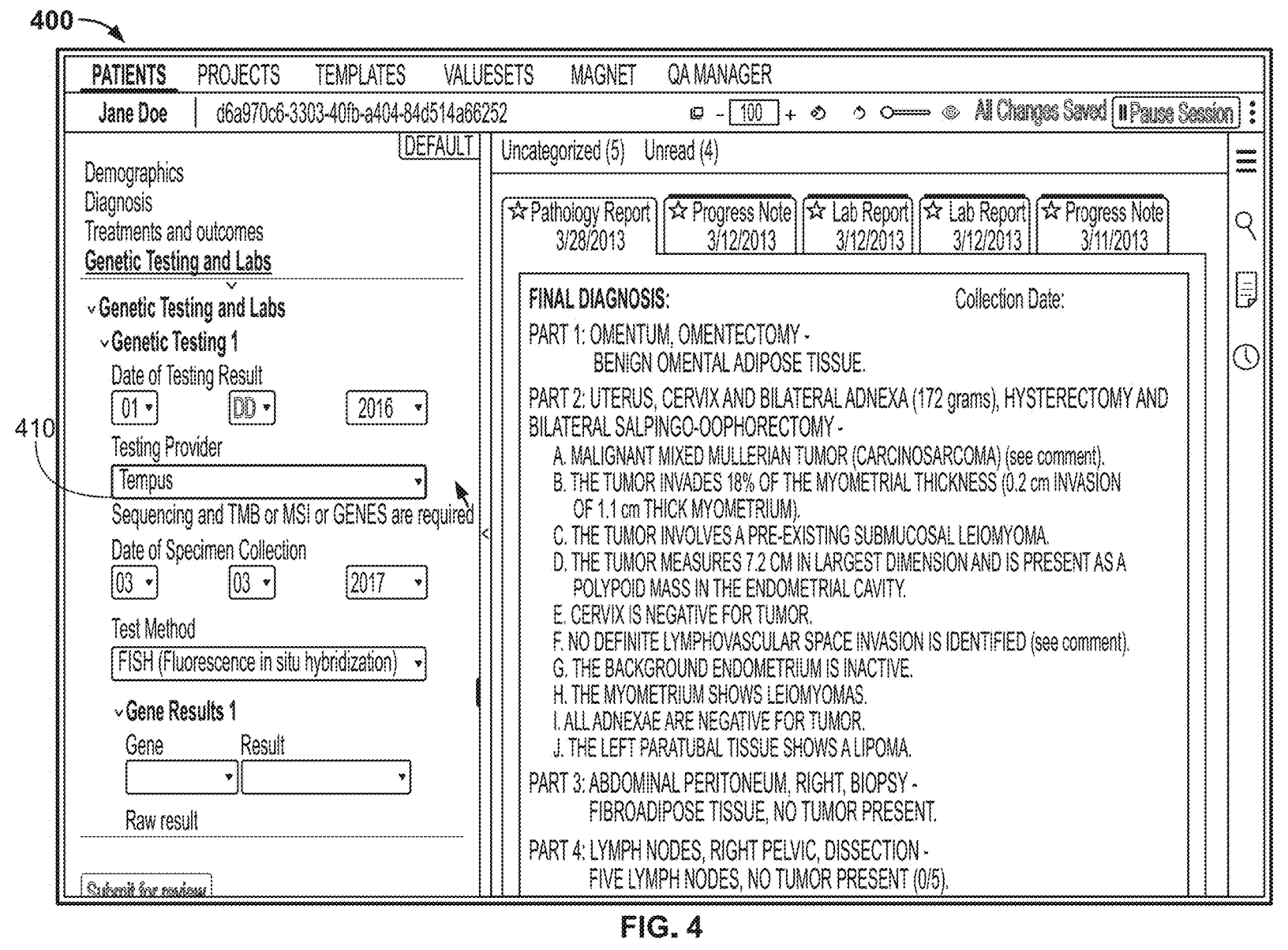
Figure 5:
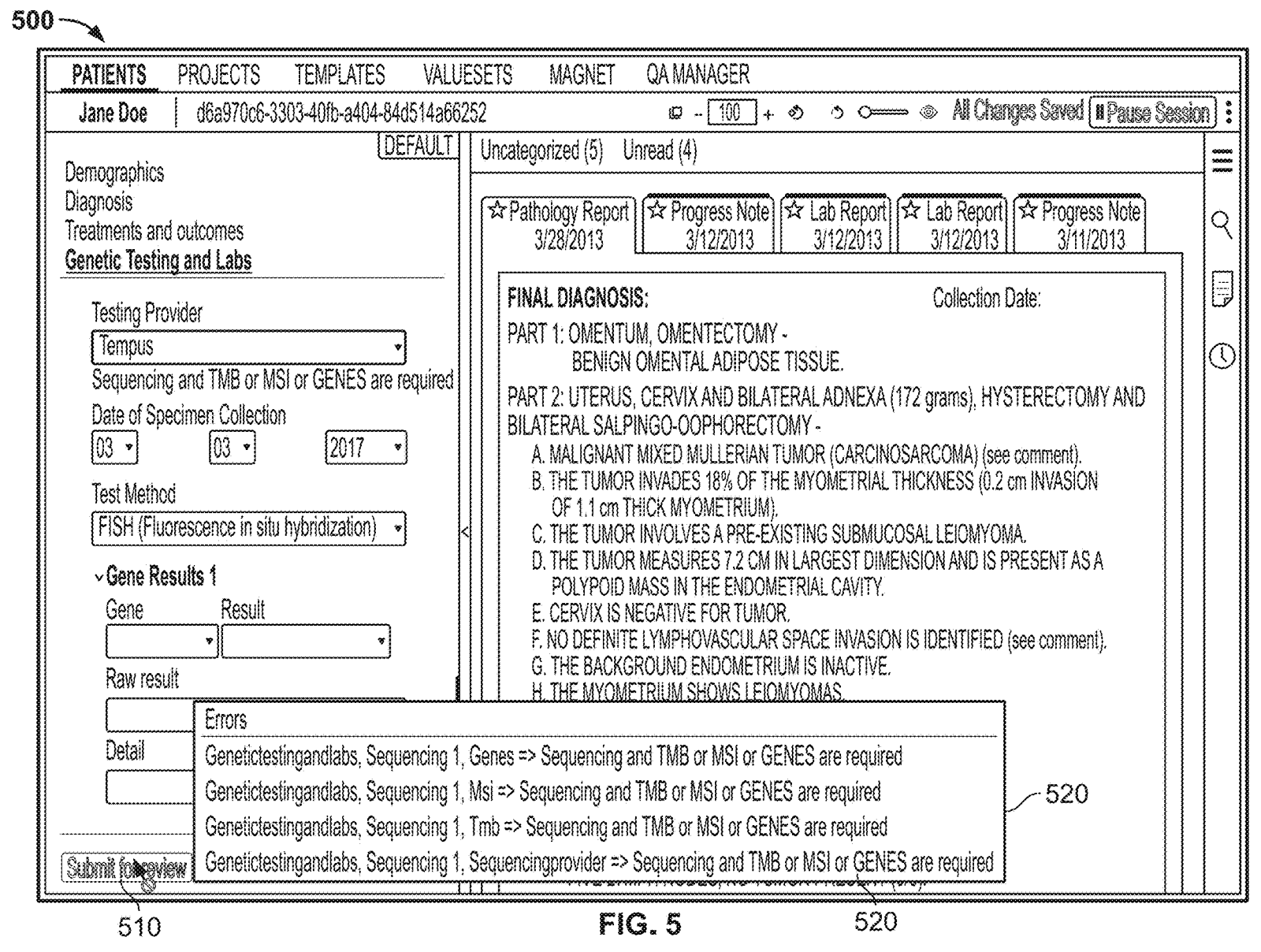

Referring now to FIGS. 4-6, another hard warning example is provided via GUIs 400-600. As shown, entering the testing provider "Tempus" can generate a hard warning 410. System 100 can recognize that "Tempus" testing reports can have a number of attributes (e.g., TMB, MSI, IHC, etc.), and accordingly, an error/warning state can occur when system 10 detects that the entered data is insufficient. As shown by FIG. 5, the selection button "submit for review" 510 can appear grayed out if certain data (e.g., genetic data) is missing and/or insufficient. Hovering over the "submit for review" button 510 can trigger an error pop-up window 520, which can list each outstanding error in the current data entry form. As indicated above, based on the testing provider ("Tempus"), system 100 is looking for specific information before the abstractor is permitted to submit the data form. As indicated by the red warning boxes 610 shown by FIG. 6, TMB and MSI data has not been entered. The data, in some embodiments, cannot be properly structured and stored without one or more of the TMB and MSI options filled in. In other embodiments, the data can be properly structured and/or stored without such options, with the approval of a designated individual (such as the user's manager).

Figure 7:
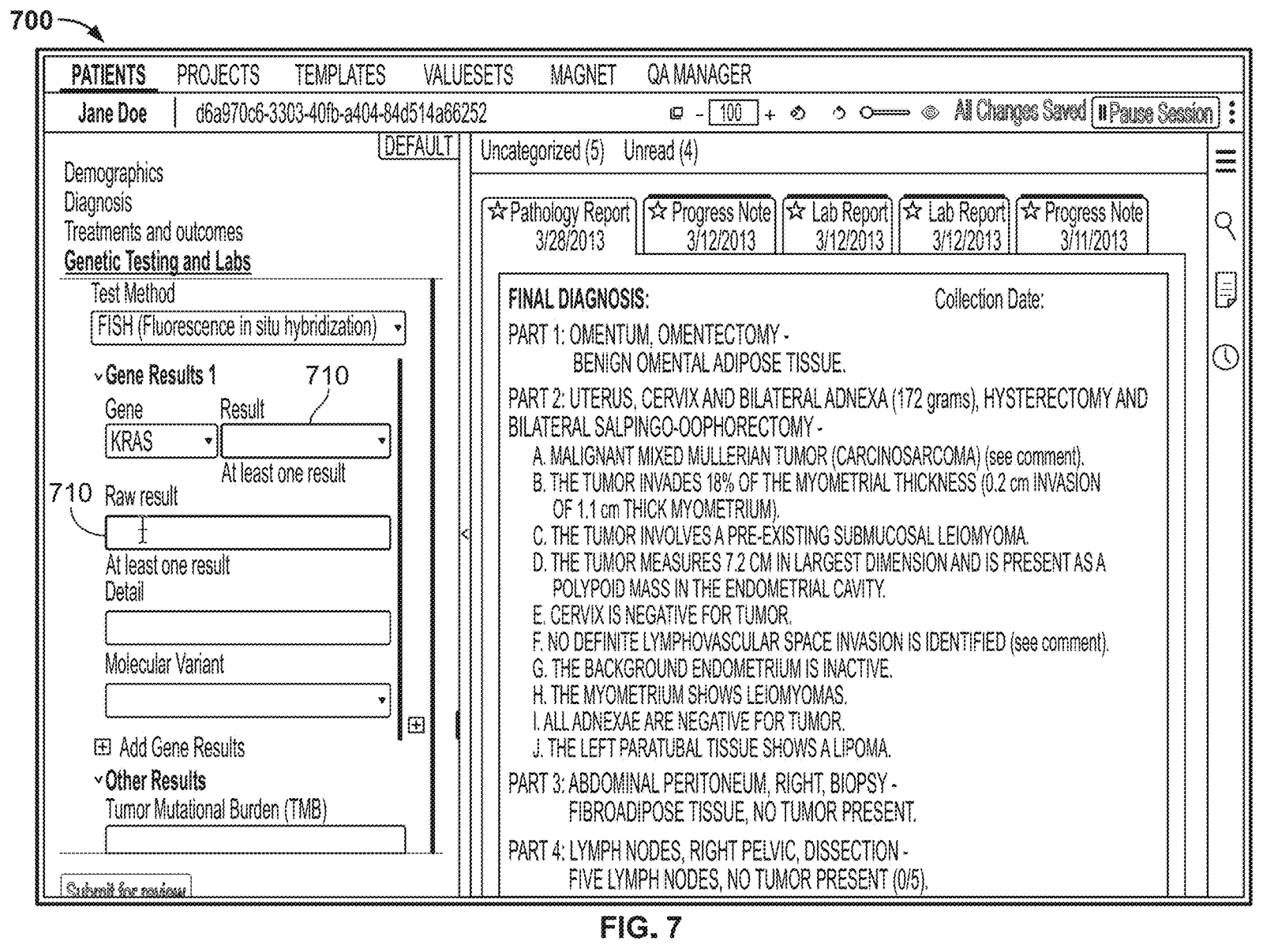

Referring to FIG. 7, as an example, the gene "KRAS" can be input into the gene results portion of the data form. As shown, new warnings occur; for instance, the data entry element may be outlined with a warning color (such as red). For instance, entering "KRAS" as the Gene may cause outline of the result entry box 710 to change color to red. A written warning (such as "At least one result") may also automatically be displayed in proximity to the result entry box 710. Similarly, hovering over or selecting the "submit for review" selection button 720 can trigger an error pop-up window with new outstanding errors corresponding to the data entry form. Selecting a "result" that corresponds to the gene can eliminate the outstanding error warning, and the user (e.g., data abstractor) can now successfully select the "submit for review" button 720.

Referring now to FIGS. 8-17, the "Validations Manager" module can be an administrative module where validations can be contained, revised, authored, etc. FIG. 8 shows an example table 810 via GUI 800 within Validations Manager that contains multiple exemplary validations and test validations that can produce some of the soft and hard warnings as described above. Some example validations include "immunophenotyping result text is a number" 820 (i.e., text entries are not permitted for immunophenotyping results), "heme additional diagnosis date of recurrence" 830 (i.e., date entries before the date of diagnosis are not permitted), and "date validations after birth" 840 (i.e., date entries that occur before birth are not permitted). In some embodiments, the various validations can ensure that only quality data is accepted into the system 100. Each validation can be represented with a name, description, date of creation, a user ID corresponding to the validation author, a level (e.g., error, warning), and the option to edit the validation. Additional disclosure relating to validations may be found below, with respect to FIGS. 59-76.

Figure 9:
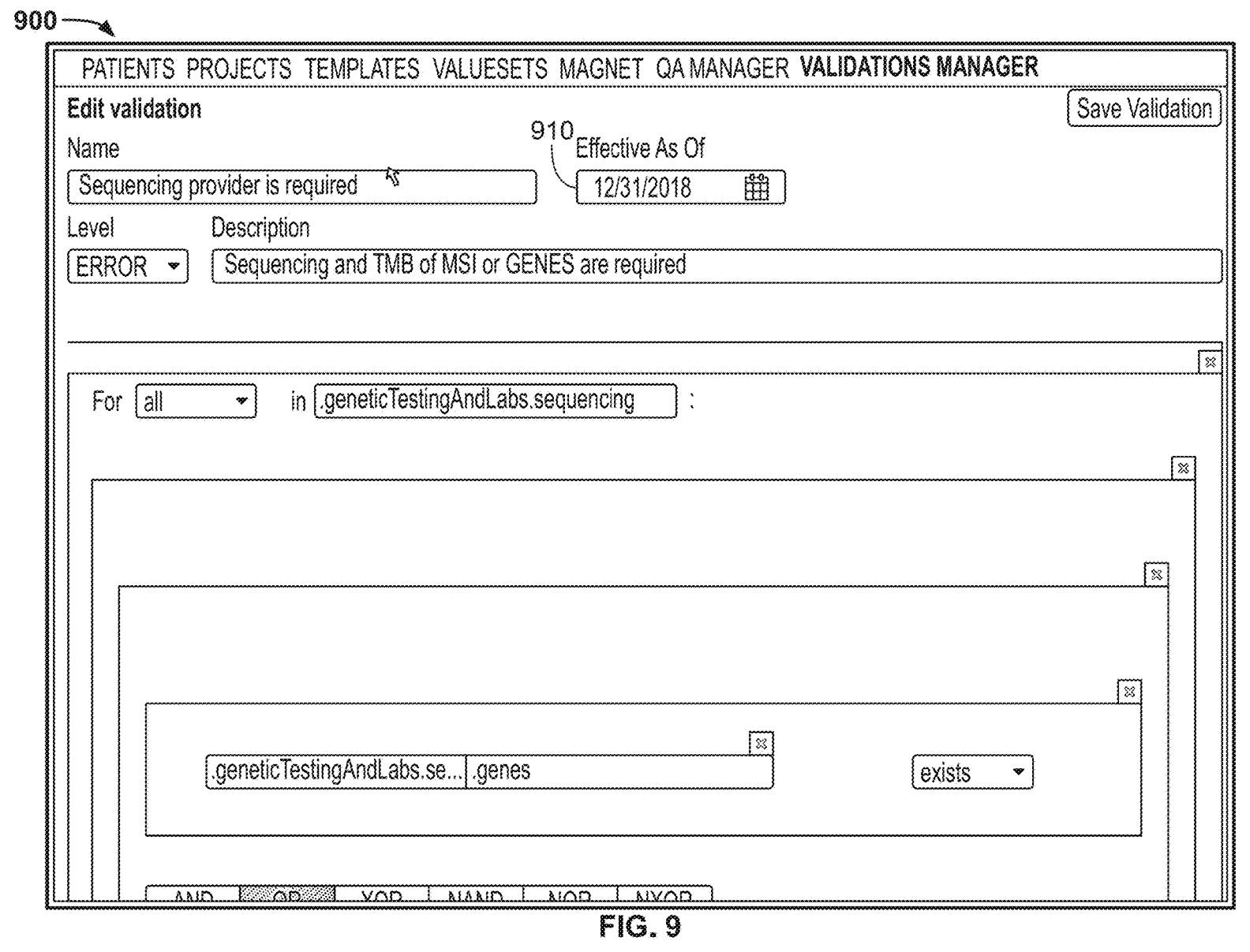
Figure 10:
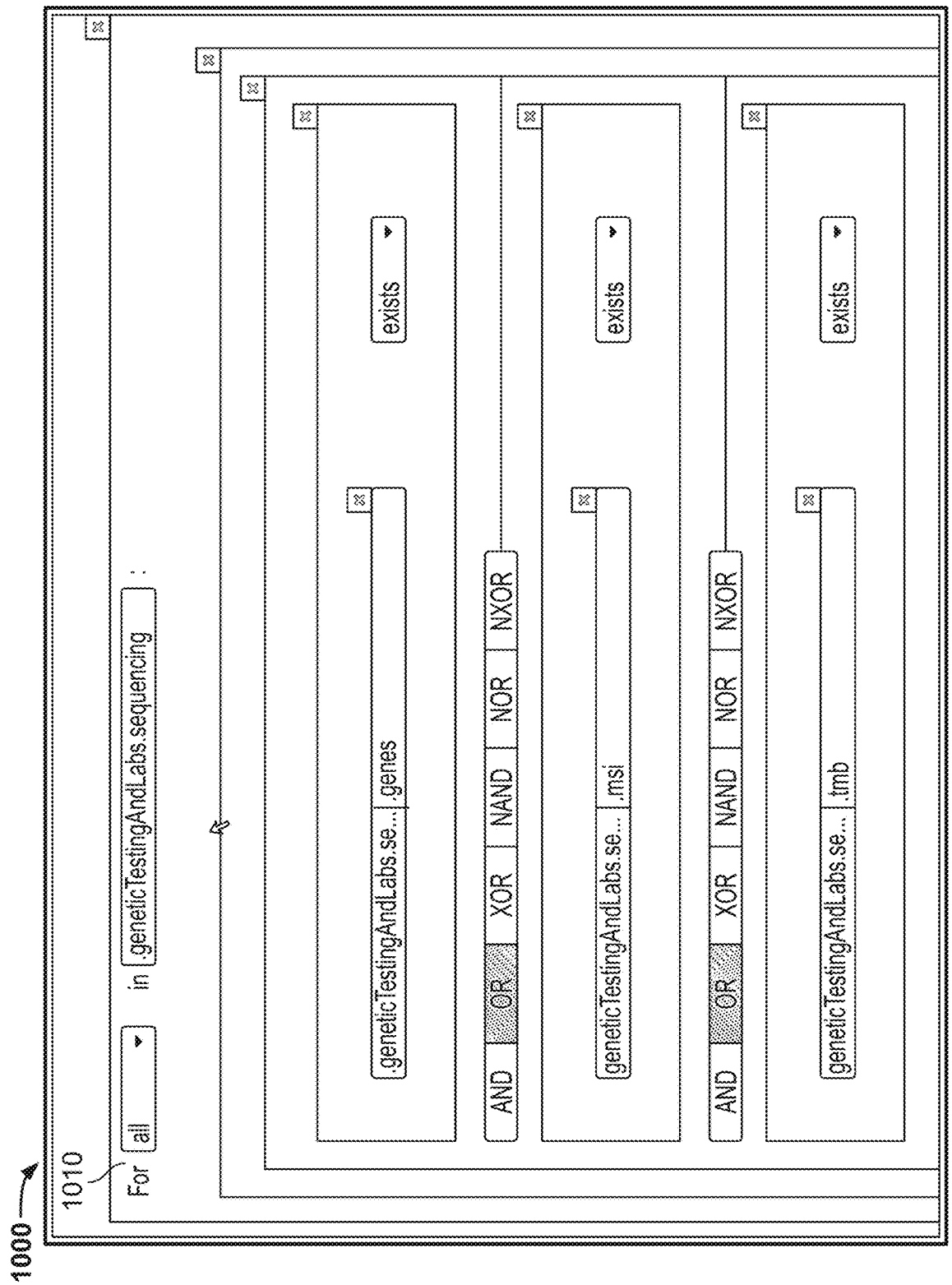
FIG. 10 is another image of an example graphical user interface (GUI), according to aspects of the present disclosure.

As shown by FIG. 9, a user can edit existing validations via GUI 900. In some embodiments, the effective date can be set to a future date using an input such as a calendar dropdown menu 910, and the validation will not activate until that future date. In the lower portion of the window, a dropdown menu is displayed that has been selected to an "all" value. This selection reflects that FIG. 10 shows a rule authoring system that can be configured to create rules for each validation via GUI 1000, according to some embodiments. Various combinations can be created using conditional statements (e.g., AND, OR, NOT, etc.). In some embodiments, multiple data sets can correspond to a single patient. As one example, a patient can have a first genetic test and a second genetic test. The rules for each validation can, for example, apply to each instance of data (e.g., validation can occur for both the first genetic test data and the second genetic test data). This can be configured and/or changed using the rule authoring system, and specifically, the "For" dropdown menu 1010 which is shown as "For" "all." As shown by FIG. 10, each gene report for this sequencing provider requires a gene, or MSI, or TMB data.

Figure 11:
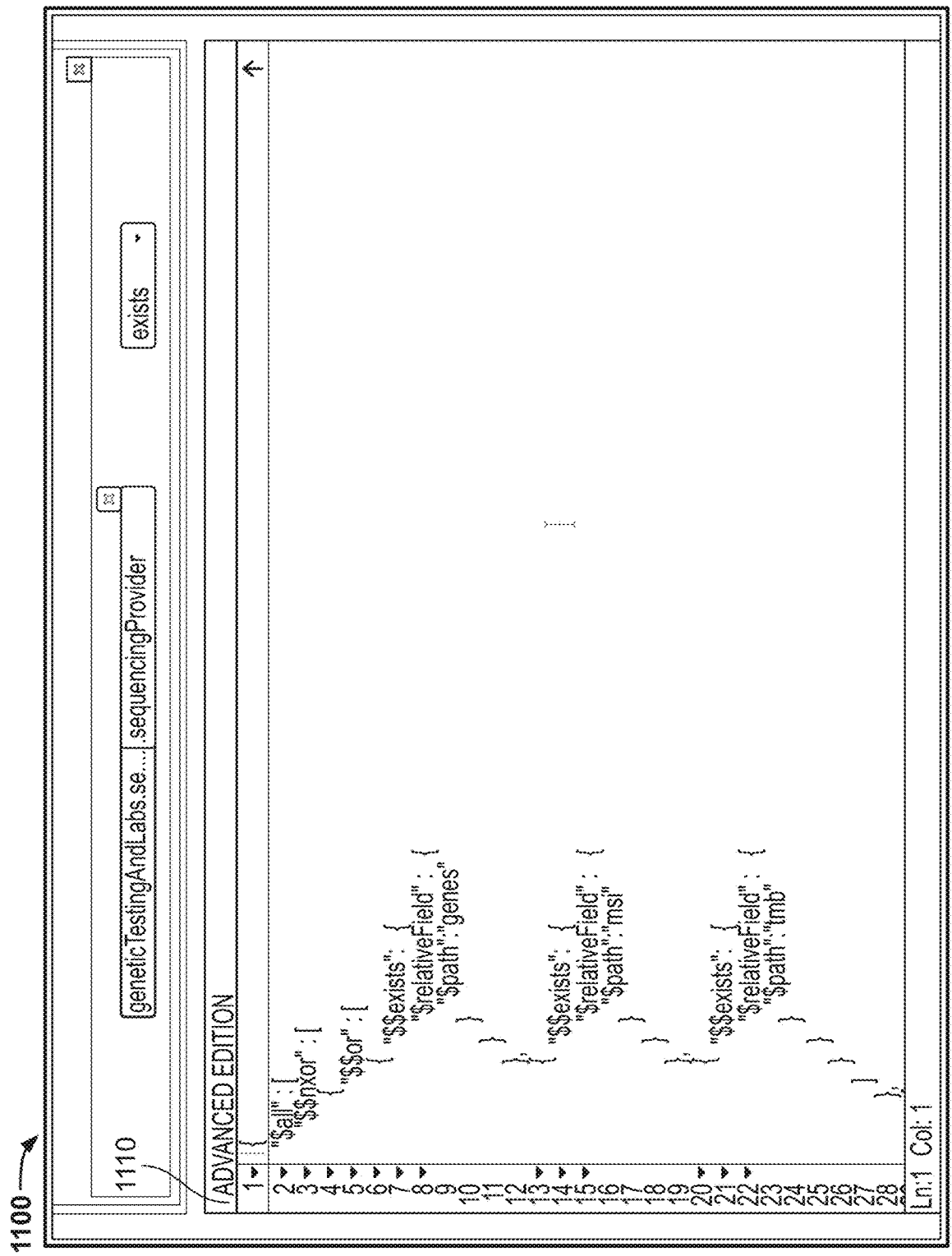
FIG. 11 is another image of an example graphical user interface (GUI), according to aspects of the present disclosure.

As shown by FIG. 11, via GUI 1100, the rule authoring system can include a validation language that can take rules authored in the user interfaces of FIGS. 9-10, and translate the rules to corresponding code 1110 for implementation in system 100. In some embodiments, a new rule can be applied retroactively to existing patient data, such that new insights can be gleaned without being restricted to patient data entered moving forward. In some embodiments, the ability to add new rules to existing validations may be restricted to certain authorized users. However, a broader class of authorized users can still create new validations with new rules.

In some embodiments, the ability to add new and manage existing rules can be performed programmatically in the absence of a GUI (e.g., GUI 1100). In some situations, this can help with the composition of bulk validation checks that, for example, can assess the validity of reported AJCC cancer staging by cancer and its corresponding sub-type. Additionally, in some embodiments, programmatic rule management can enable, accelerate and/or help to manage various validation checks within and across systems (e.g., system 100), tools and applications, such as clinical trial matching, the management of lab specimens in a Laboratory Information Management System (LIMS) solution, the information stored in a patient electronic health record, or the information stored in medical coding and billing systems.

Referring now to FIG. 12, a new validation can be created by a user via GUI 1200, according to some embodiments. In contrast to editing existing validations (which can be restricted to certain authorized users), creating a new validation can now provide a user with an "add block" function. As shown, GUI 1200 can display a dropdown menu 1210 of selectable functions that can be customized for the specific validation.

Figure 13:
FIG. 13 is another image of an example graphical user interface (GUI), according to aspects of the present disclosure.
Figure 21:
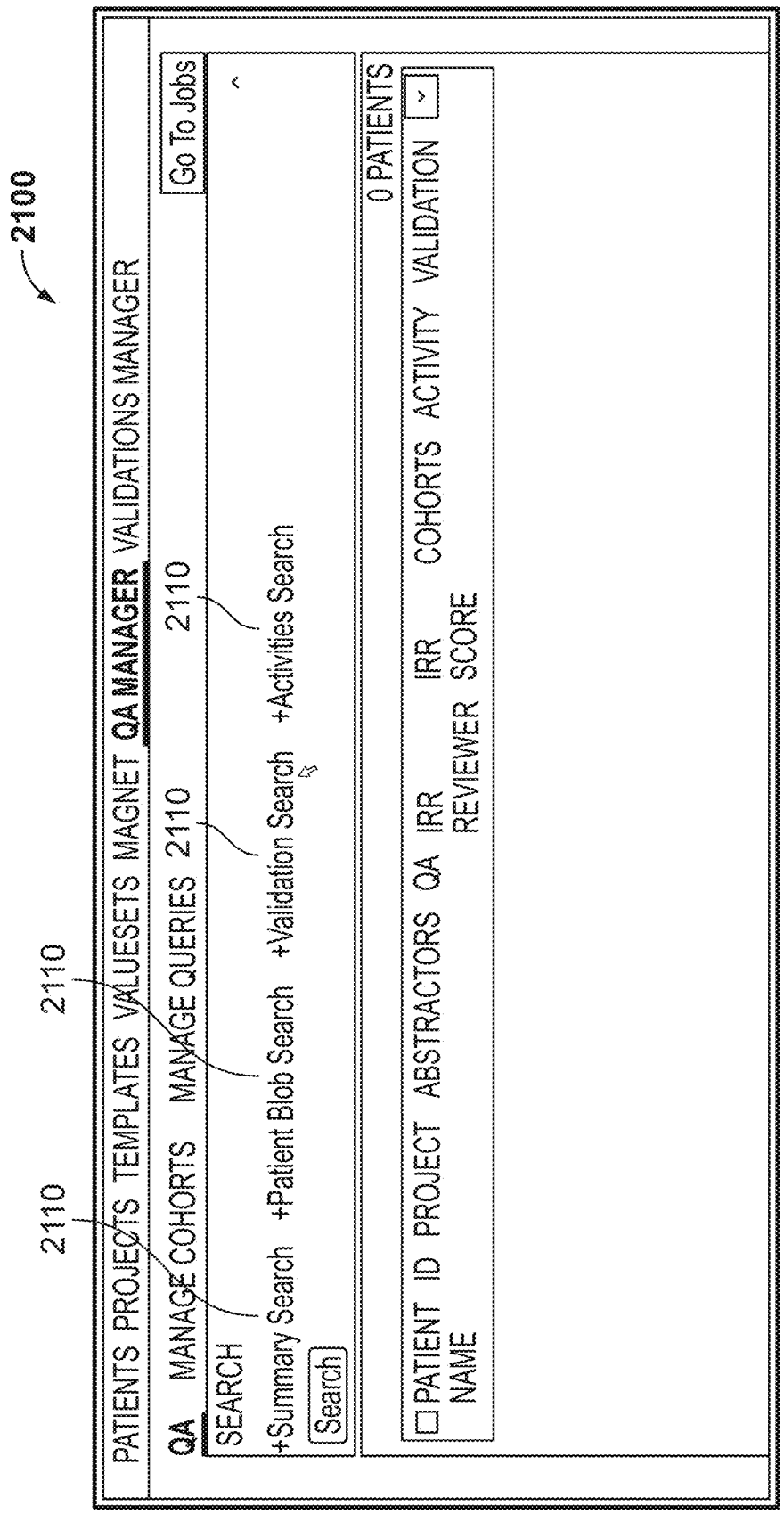
FIG. 21 is another image of an example graphical user interface (GUI), according to aspects of the present disclosure.

FIGS. 13-15 show the development of a new validation via GUIs 1300-1500. A new validation may enable the utilization of a template that permits the grouping of patients into one or more distinct cohorts. Such a grouping may be valuable for a variety of purposes, such as being able to search the one or more cohorts for certain health criteria, such as clinical, molecular, genetic, or imaging criteria. In other use cases, the system 100 can find all sites for all patients where an indicated diagnosis exists.

In some embodiments, the validation may be developed using a selection tool such as a search bar 1310, that may receive a search term from a user and display a suggestion menu 1410 based on the search term in order to reduce user search time. The suggestion menu 1410 may be populated from the one or more templates associated with the validation. As an example, the four categories displayed in suggestion menu 1410 may be matched back to the list of items displayed in panel 210. After a category 1510 from suggestion menu 1410 has been selected, the rule authoring system can create the corresponding system code for the new validation. For example, the selection of the category 1510 may trigger the appearance of sub-level data entry elements tied to the selected category 1510. As shown in FIG. 15, for example, the selection of .diagnosis.primaryDiagnosis.site.display as category 1510 populates the rule displays shown below the label. The field ".diagnosis.primaryDiagnosis.site.display" refers to the text that is in a set of structured data that reflects the primary diagnosis of a tumor at a site of biopsy. For example, the value of that text entry may be "breast cancer," "prostate cancer," or the like. However, it should be understood that in the examination of a patient's medical record, particularly the medical record of a medically complex patient such as a metastatic cancer patient, there is a substantial amount of information in the record that may suggest the factual primary diagnosis of a cancer at a site. In addition, because medical records are updated over a period of many years and many clinical visits, it is often the case that information collected in the medical record over time may be inconsistent—that is to say, records from a first clinical visit may indicate that the size of the tumor is 5 cm while records from a second clinical visit may indicate that the size of the tumor is 6 cm. This may be because the size of the tumor has changed between appointments. Or, it may be a data entry error that was not corrected in the medical record. For this reason, a validation may be set up to check one or more structured data fields for internal value consistency as a condition to ensuring that the primary diagnosis text can be relied on with a high level of confidence, given the extensive and sometimes contrary information in a medical record.

Referring back to FIG. 15, an entry field may receive input related to the selected category 1510. As shown in FIG. 15, the entry field is in the form of a text box with the informational label "Type . to get suggestions . . . ". This indicates to the user that she/he may start typing in this text box in order to get suggestions about rule items, such as the rule items shown in FIG. 17 labeled 1720.

Figure 17:
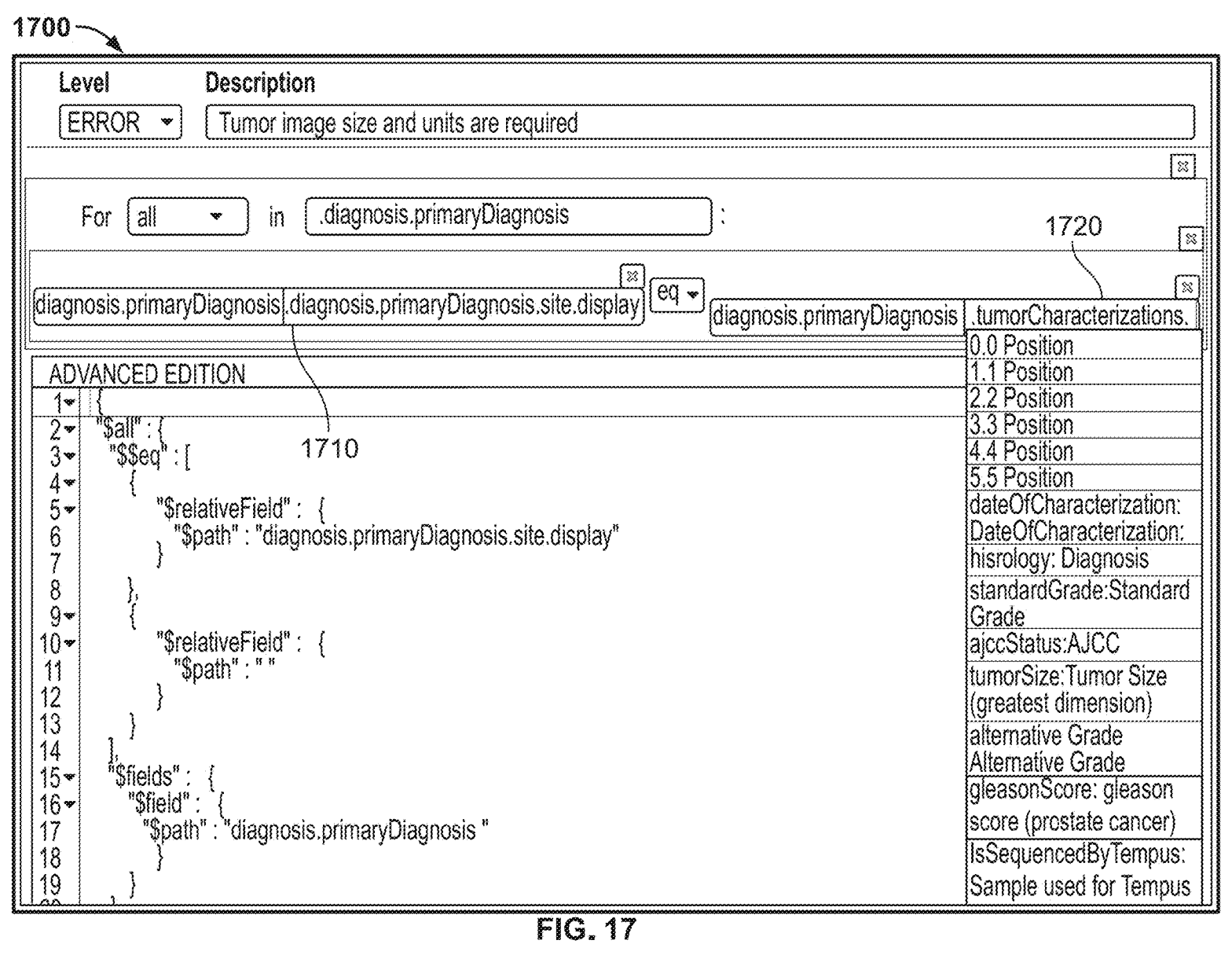
Figure 19:
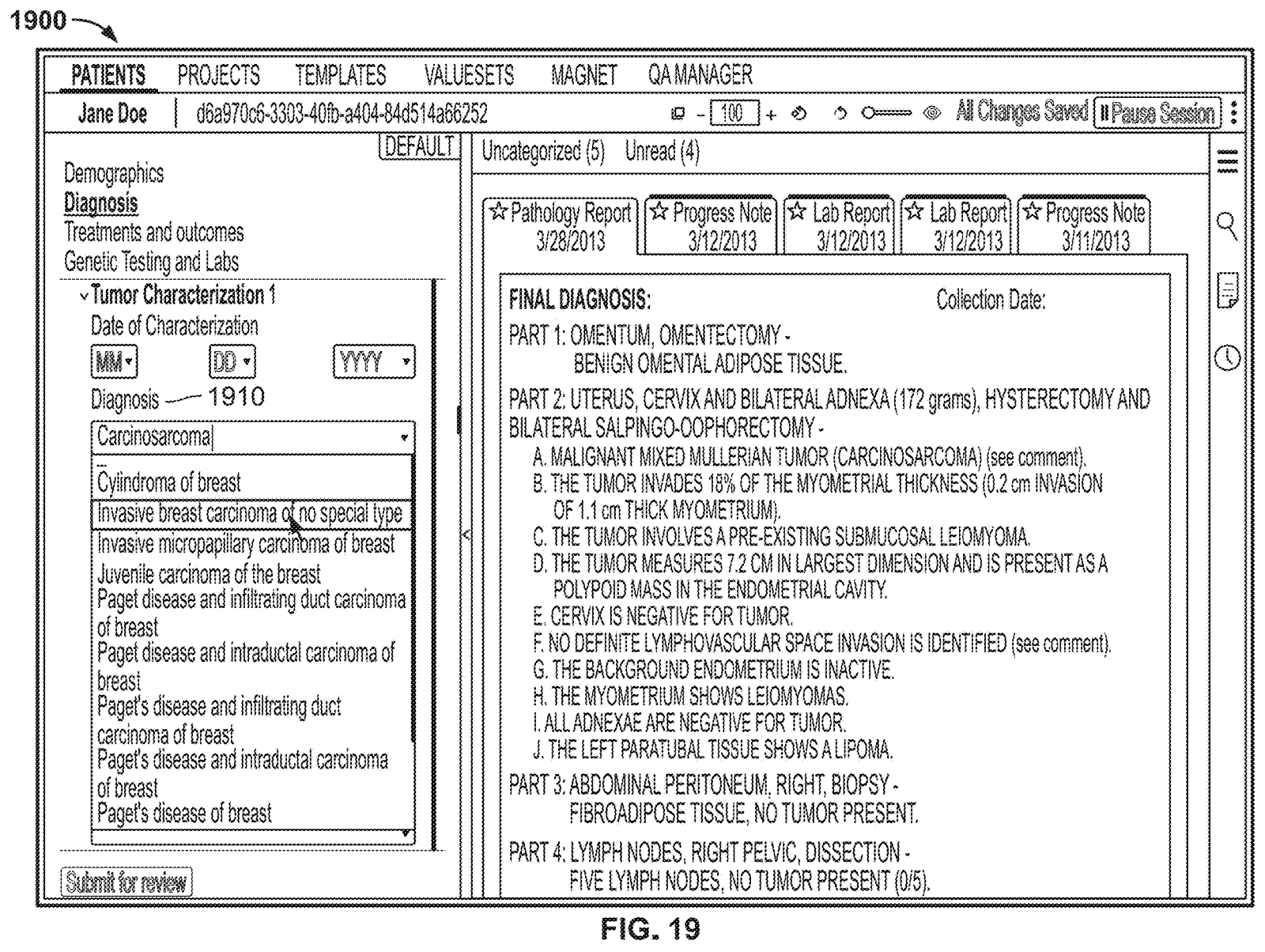

As shown by FIGS. 16-17, additional rules can be added to the new validation via GUIs 1600-1700. As an example, a comparison can be added as a rule using a selection tool such as a dropdown menu 1610. In this comparison, the query starts with primary diagnosis and the display text for the primary site. As shown, system 100 can consider every single diagnosis for a patient, and enforce the equality between the site display text for the primary diagnosis 1710 (e.g., "breast," "lung"), and any tumor characteristic 1720 that has been entered with a histology. As an example, FIGS. 18-19 show, via GUIs 1800-1900, a tissue of origin text 1810 corresponding to "ovary," and a diagnosis text 1910 that includes "carcinosarcoma." Accordingly, the equality of the new rule can be satisfied, and no new errors/warnings would result from the instant patient data.

Figure 20:
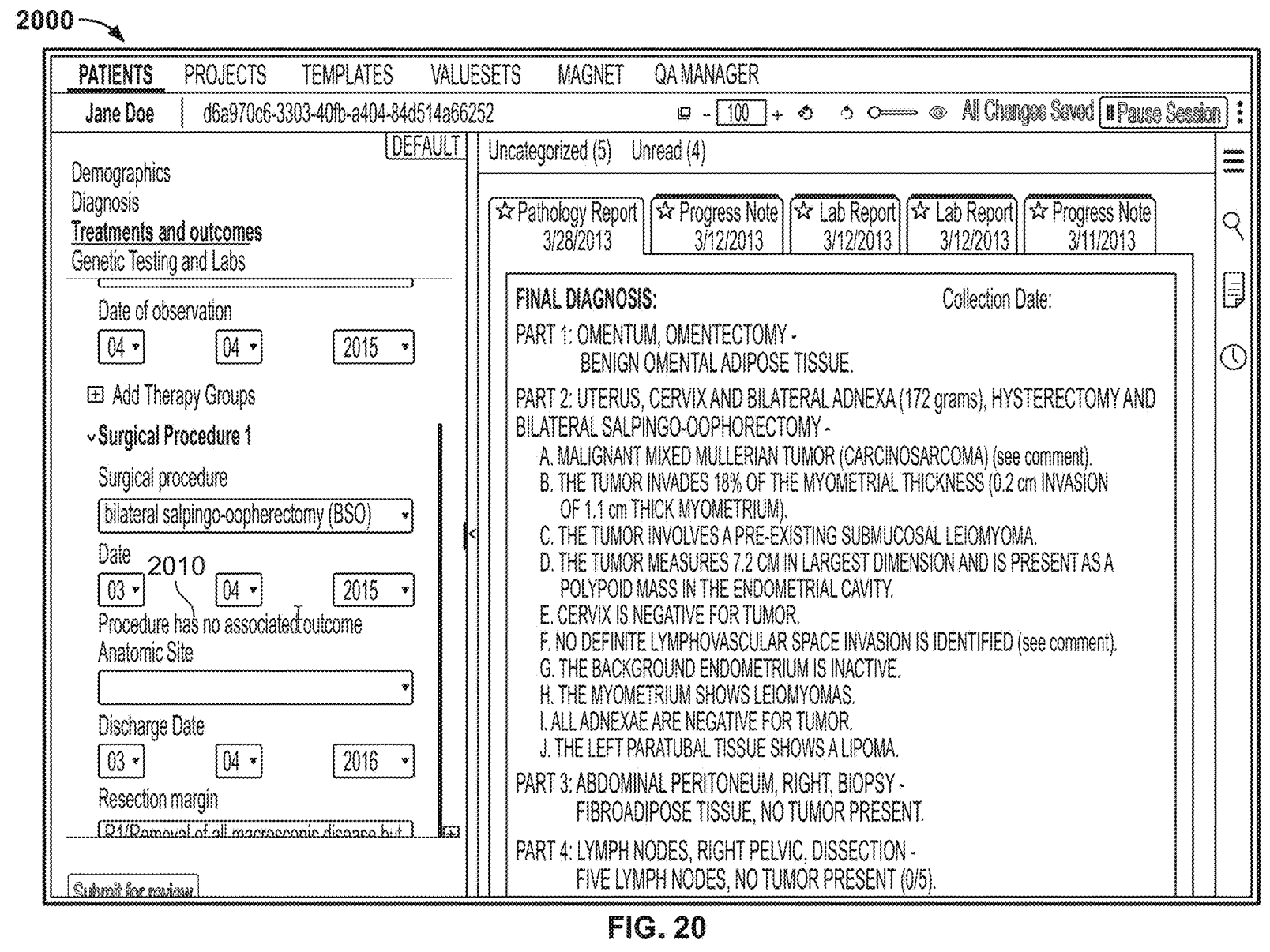

Referring now to FIG. 20, an example of a "soft" warning is shown, according to some embodiments. GUI 2000 can display a yellow warning text 2010, such as the text shown in FIG. 20. As shown, system 100 expects a procedure outcome due to the input surgical procedure "bilateral salpingo-oopherectomy (BSO)." Notably, a user (e.g., a data abstractor) may still submit the patient data without resolving the soft warning, and the GUI 2000 may continue displaying the yellow warning text 2010.

Figure 24:
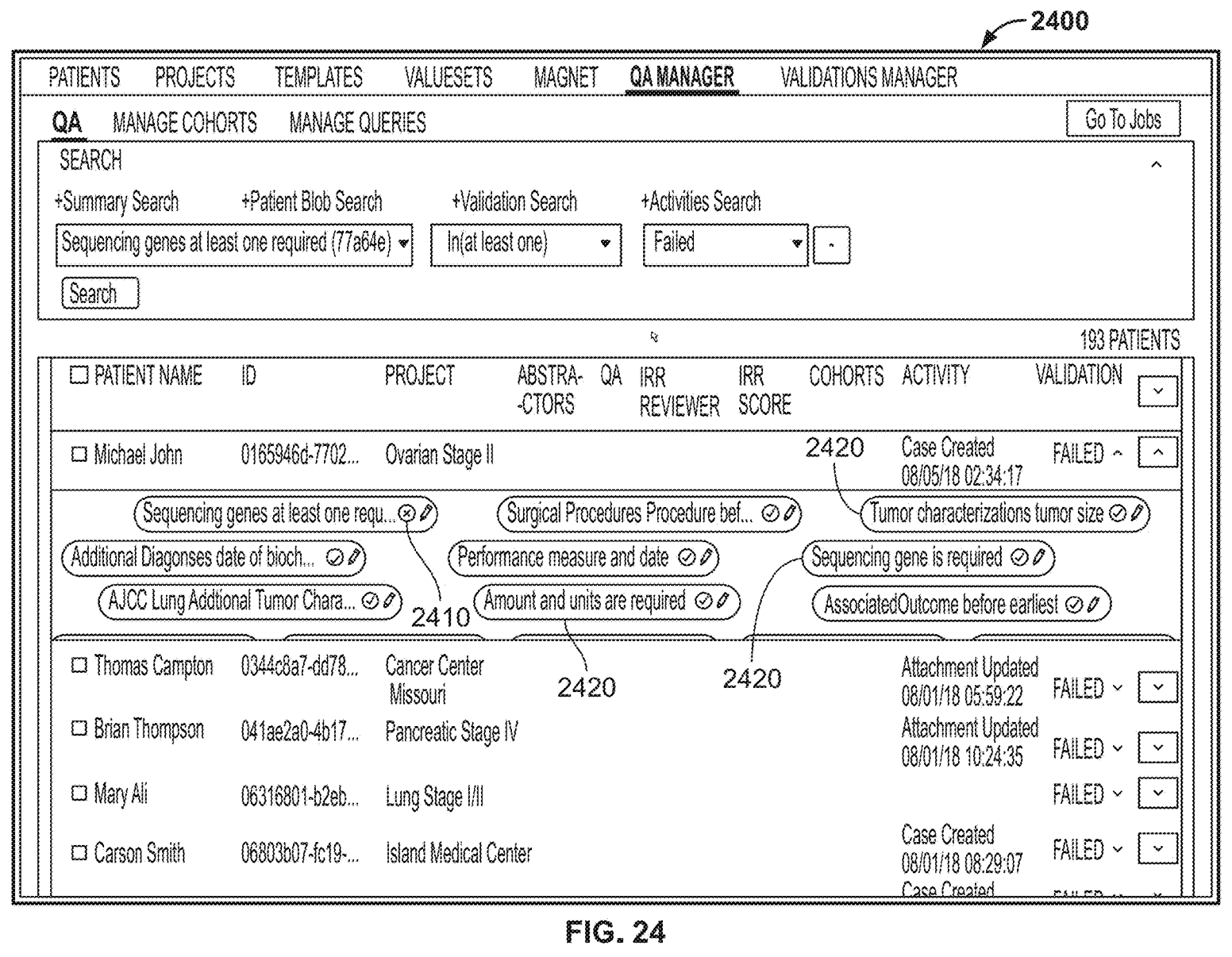
Figure 25:
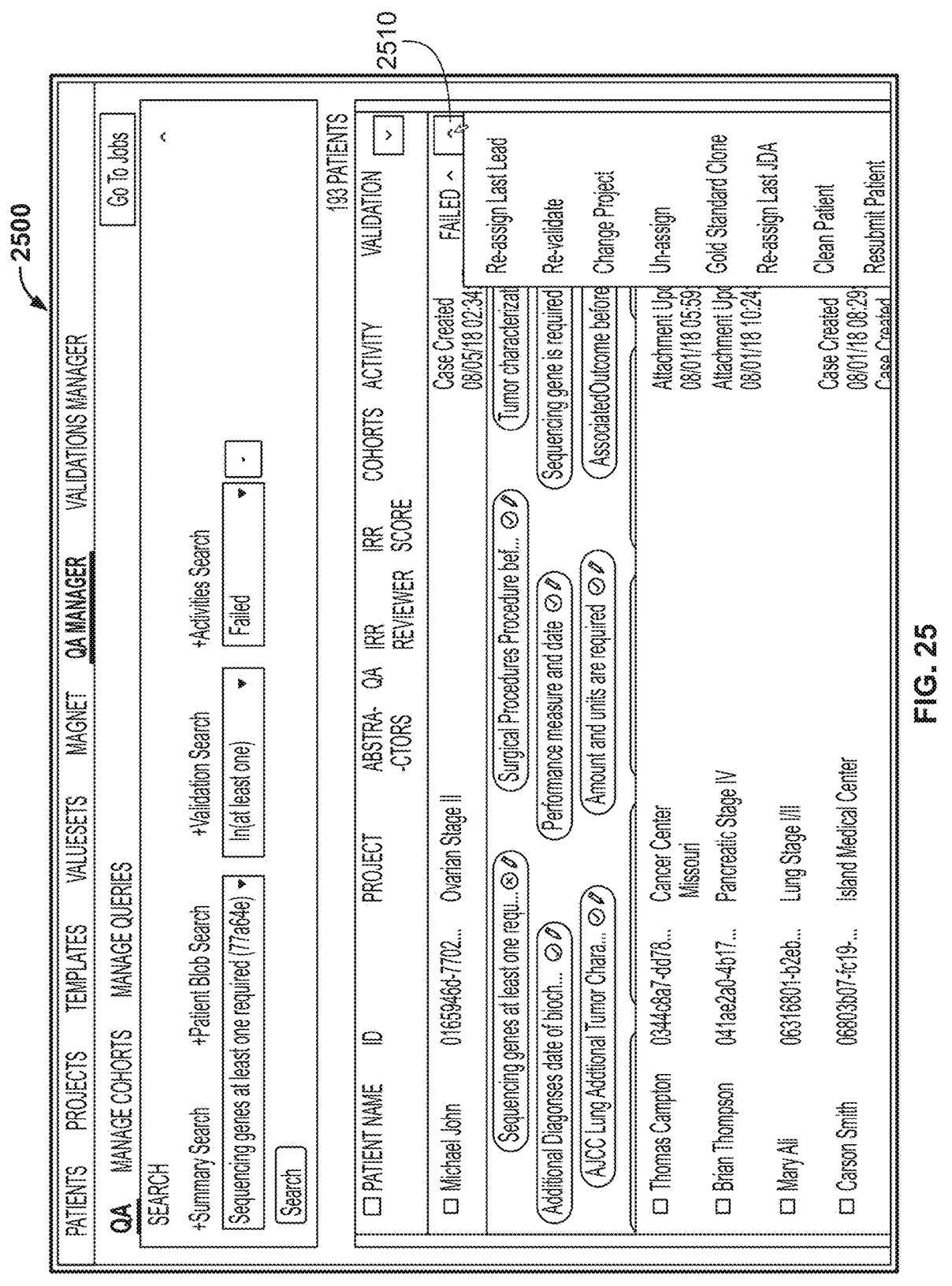

Referring now to FIGS. 21-25, a "QA Manager" module is shown, via GUIs 2100-2500, according to some embodiments. In some embodiments, the QA Manager can include a number of controls that allow users to find matching patient cases based on certain criteria. Further aspects of the QA Manager module are discussed below with respect to FIG. 63. The controls may include one or more add search buttons 2110, which may be used to create one or more search rows 2210 corresponding to a search type such as a summary search, a patient search, a validation search, an activities search, or another applicable search type. Each search type may have one or more dropdown menus, search bars, or other input selectors to receive one or more search parameters. A search may permit the selection of a particular validation for further analysis. For instance, as shown in FIG. 23, the exemplary validation "sequencing genes at least one required (77a64e)" can be selected from a dropdown menu 2310 of existing validations. A user can, for example, search for all patients from one or more cohorts where that selected validation has "failed." In some situations, this search functionality can be used to efficiently resolve errors across many patients. Cases that are in a "failed" state can quickly be identified based on this status within system 100, and action can be taken to resolve each case. As shown by FIG. 24, a user (via GUI 2400) can select individual patients, and a dropdown summary can be displayed. As an example, an error identifier 2410 indicates that the selected patient data failed the validation "sequencing genes at least one required." As shown, other identifiers 2420 indicate data types that were successfully validated. In some embodiments, a dropdown menu 2510 (as shown by FIG. 25) can provide several options for the selected case/patient. In particular, the case/patient can be reassigned to a different abstractor (or "JDA"), assigned to a new manager (or "Lead"), moved to a different project, or resubmitted, among other things.

In some embodiments, role-specific errors and/or warnings can be included within system 100. This can include, for example, requiring a user (such as a data abstractor) to acknowledge a soft warning before submitting the patient data for review. In some embodiments, this can further include prompting a user to provide a rationale for ignoring the soft warning. Advantageously, this can ensure that users are at least aware of the soft warnings prior to submitting the patient data.

In some embodiments, the workflow management system can accommodate not only written patient documents, but also electronic medical records (EMRs). For example, the workflow management system may be integrated into an existing EMR platform, such as the EMRs offered by companies like Epic, Cerner, or other providers. When integrated into an existing EMR platform, the workflow management system can, according to some embodiments, automatically pre-populate data fields within system 100. Accordingly, data abstractors can verify/correct pre-populated data as opposed to exclusively performing manual data entry.

Additionally, in some embodiments, optical character recognition (OCR) and natural language processing (NLP) can be implemented to pre-populate data fields from written/scanned patient documents. Once pre-populated, the data fields may be displayed to a user for manual approval, or the data fields may be automatically approved based on pre-determined criteria, such as a threshold that indicates the probability that the pre-populated information is in error is less than an error rate for manual data entry.

Referring broadly to FIGS. 26-41, GUIs 2600-4100 show details corresponding to the "Templates" module, according to some embodiments. A user can utilize a template created in the "Templates" module in order to allow a data abstractor to ingest clinical records from various sources (such as a clinical record) and convert that data to normalized and system optimized structured data sets specified in part by the template, according to some embodiments. In one embodiment, templates may be associated with a project, so that any source documents which are abstracted for the project automatically are associated with the template. In another embodiment, templates may be selectable by the abstractor during abstraction based off of the source document they are currently working on. In yet another embodiment, templates may be associated with specific documents so that when a source document is opened, the corresponding template is referenced to build the correct abstraction fields. During abstraction, an abstraction user may add new fields into the preloaded template fields as needed.

Referring to FIG. 26, GUI 2600 shows details corresponding to the "Templates" module. A template 2610 can be linked to one or more projects, and can specify what types of data fields can be input for patients in each linked project, as will be explained below. Each project linked to the template 2610 can be shown in a project list 2620. Each template can have a name 2630 and a "date created" 2640 displayed. Each template 2610 can be used to quickly and dynamically change data fields of each patient case belonging to a given project. A new template can be created by selecting a "new template" button 2650.

Referring to FIG. 27, GUI 2700 shows details corresponding to the "Patients" module. The template (e.g., template 2610) can be used to set one or more data fields that are enabled for use by the abstractors in the "Patient" module for each patient case in the project. In some embodiments, a data field 2710 may have one or more nested elements 2720, such as in the case of the data field "Date of birth," which can have nested elements "Month," "Date," and/or "Year." A client such as a hospital can provide raw data in the form of clinical documents, pathology reports, progress notes, testing data, electronic medical records (EMRs), or other relevant medical history data for each patient. A client can have any number of projects, and some projects may have the same template. In some embodiments, the same template may be used across multiple projects and/or multiple clients. For instance, if Hospital A and Hospital B each require services to structure their clinical data for stage III ovarian cancer, one template may be prepared with the data fields most relevant to stage III ovarian cancer and then utilized for Hospital A's project and for Hospital B's project. In some embodiments, each data field or nested element can have a data type such as repeatable, select, text, row, text, dropdown, date, Boolean, or combinations thereof such as dropdown and date. Some data fields in each patient case may be pre-populated depending on the type of raw data containing the relevant information for the data field. For example, optical character recognition (OCR) may be run on certain file types, and the data extracted using OCR can be used to pre-populate certain data fields 2710 and/or nested elements 2720.

Figure 28:
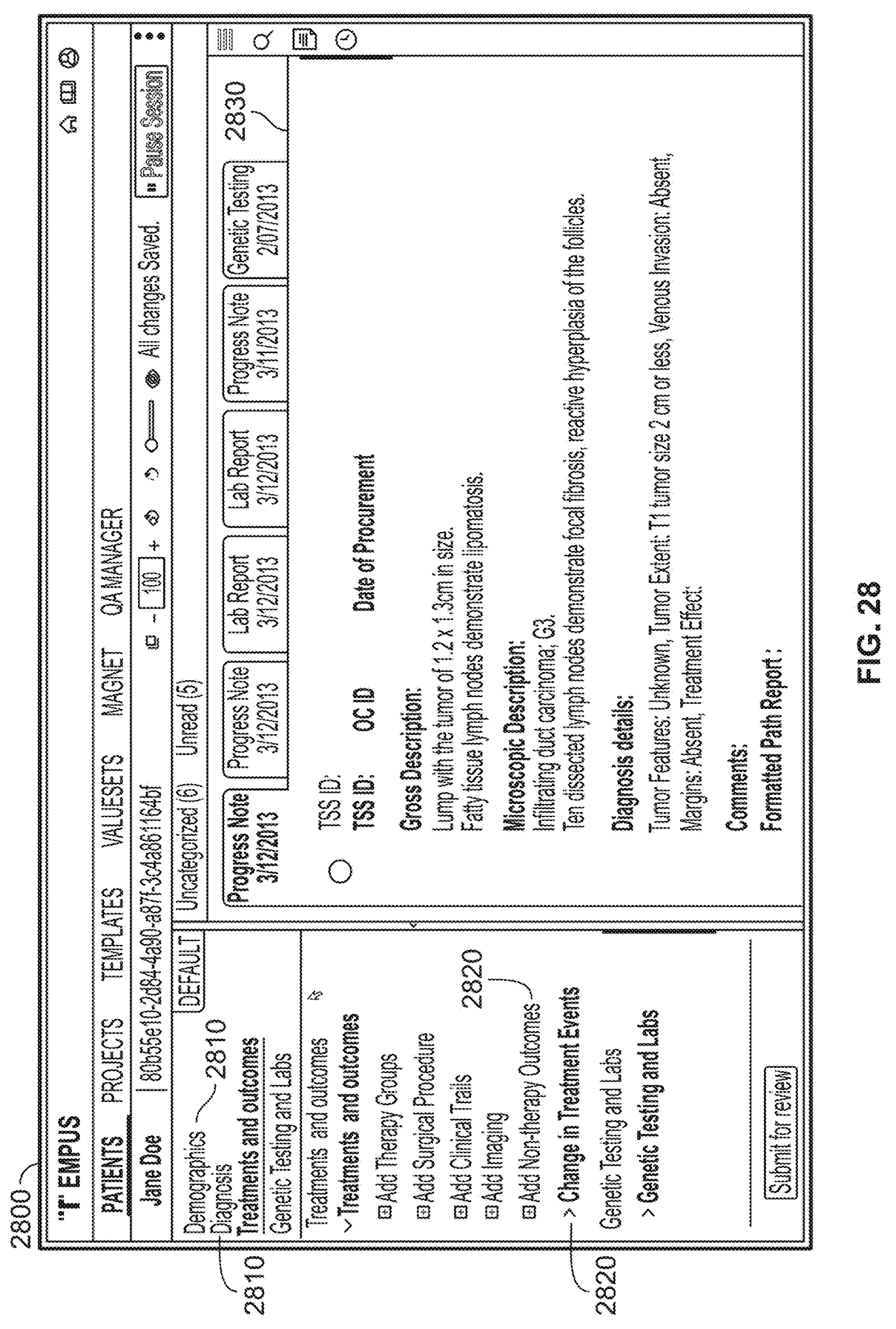
Figure 30:
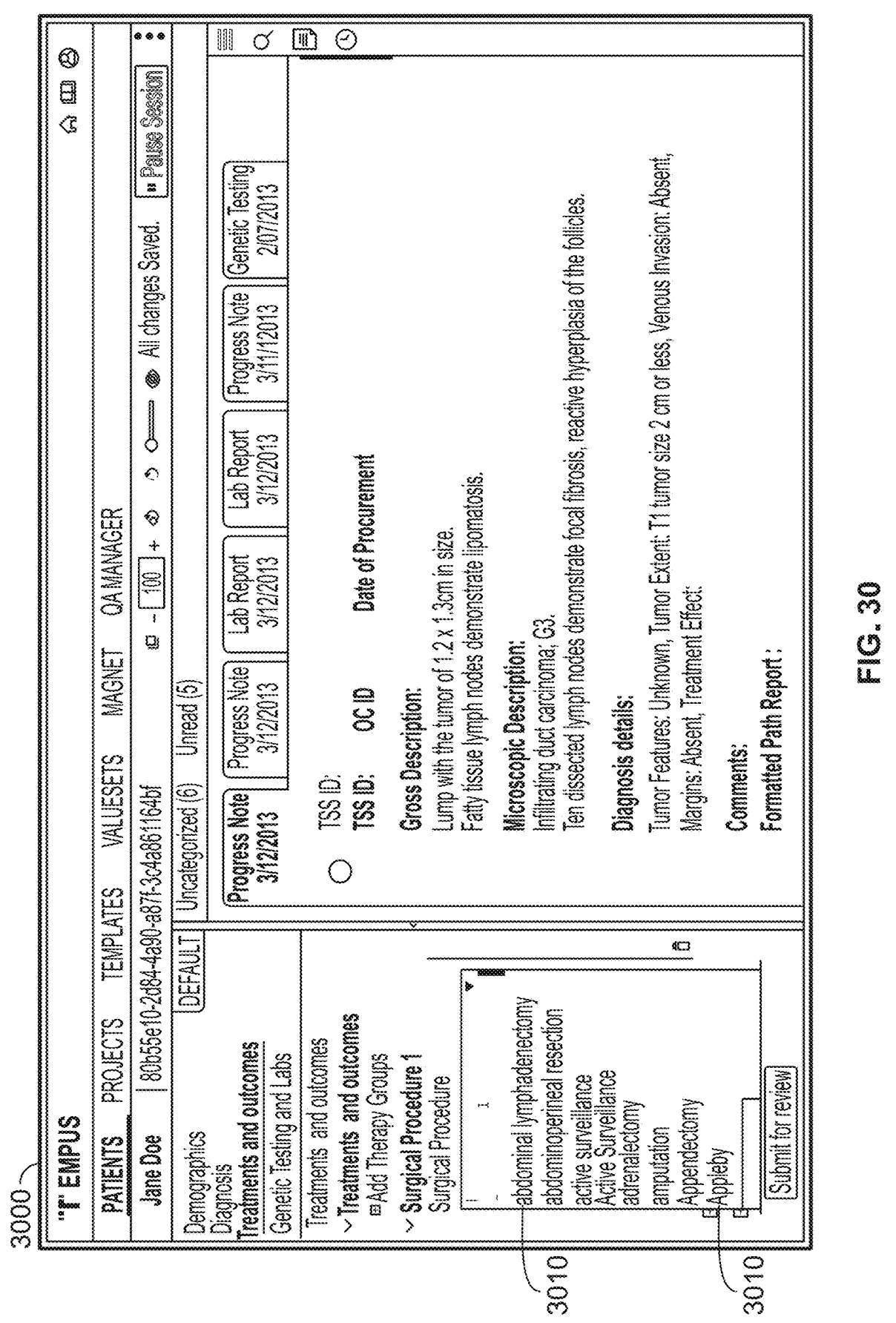

Referring broadly to FIGS. 28-30, GUIs 2800-3000 show details corresponding to the "Patients" module. For each patient case in a project, abstractors can view the data fields 2810 of the template corresponding to the project. The abstractors can then populate any unpopulated data fields 2810 in the patient case when extracting information from the raw data (e.g. progress notes, lab reports, genetic testing results, and so forth) of the patient case. Some data fields 2810 can be populated using a dropdown menu containing one or more field values 3010. The field values 3010 can be selected or set in the "Templates" module and/or the "Valuesets" module, as will be explained below.

One or more patient documents 2830 from the data provided by the client can also be viewed simultaneously, in tabbed fashion as shown in the figures, along with the data fields 2910 to allow the abstractor to efficiently populate the data fields 2910 and any required nested elements (e.g., nested elements 2720) of the data fields, according to some embodiments. The system 100 can load the patient documents 2830 using a patient identification code of the patient case. The data fields may be categorized by a root category 2810 such as demographics, diagnosis, treatment and outcomes, genetic testing and labs, or any other category that may help better organize the data fields.

Each root category 2810 can have one or more sub-categories 2830 to further organize the data fields. Some root categories 2810, sub-categories 2820, and/or data fields 2910 can be related to oncology, cardiology, depression, mental health, or other neurological disorders. diabetic disorders, infectious diseases, epilepsy, dermatology, autoimmune diseases, or neurological disorders, or any other branch of medicine. The root and/or sub-categories of each data field can be changed depending on the project using the "Templates" module. For example, a data field such as "diabetes" may be categorized in the "demographics" category for one project while being categorized in the "diagnosis" category in another project. The enabled data fields from the project's template can be shown to the abstractor.

Referring to FIGS. 31 and 32, GUIs 3100 and 3200 show details corresponding to the "Patients" module. Certain data fields can have one or more soft warning messages 3110 and/or one or more hard warning messages 3210 that the system 100 displays based on a set of rules for the data fields stored in the template. Each rule can prevent the abstractor from entering improper data and/or the abstractor from saving a patient case if the rule is violated, as described in detail above with respect to FIGS. 2-25.

Figure 34:
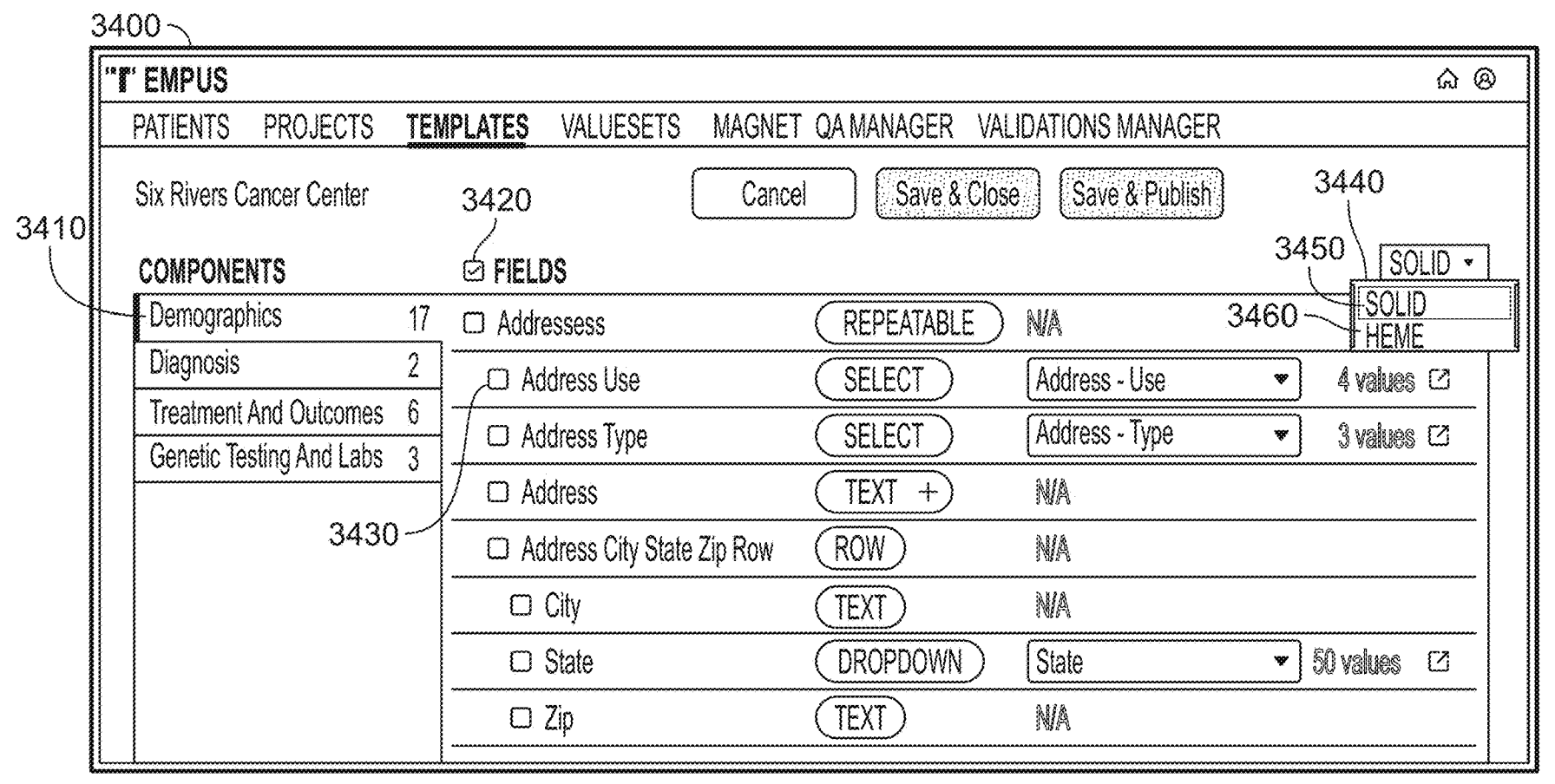

Referring broadly to FIGS. 33-35, GUIs 3300-3500 show details corresponding to the "Templates" module. A user can save a template using a save and close option 3310, which can allow the template to be saved but not published. When the template is published, any projects using the template (i.e. linked projects) will be updated by the system 100 to have the data fields of the new template available in the "Patients" module and, in some examples, elsewhere throughout the system. If the template is saved but not published, the abstractor working on a patient case in a project may not see any changes to the data fields of the template, such as updates to the data fields and/or added or removed data fields. In some embodiments, the system 100 may periodically save the template without publishing.

Alternatively, a user can save the template using a save and publish option 3320, which can allow the template to be published to projects and/or patient cases using the template. In other words, the abstractors or end users of projects and/or patient cases will see all updated, added, or removed data fields of the template. In some embodiments, the user may be prevented from removing or modifying any active fields, i.e. fields that have a checked box, in order to preserve data from being lost and/or protect the template. In some embodiments, the user may be allowed to add more active fields after publishing. In some embodiments, the template may be published, but only with respect to projects selected by the user.

Each category and/or data field may be defined and stored within a database associated with the system 10, and re-used as needed for individual templates. Each category and/or data field can belong to one or more template medical groups corresponding to various branches of medicine, conditions, diseases, or disorders that can be selected from medical group dropdown menu 3440. For example, there may be a solid tumor group 3450 of categories and data fields and a heme group or blood cancer group 3460 of categories. In some embodiments, the solid tumor group 3450 may include a diagnosis category, while the heme group 3460 may have a heme diagnosis category. Some categories may have a different number of data fields in different template medical groups, for example the solid tumor group 3450 may have seventeen data fields in the demographics category 3410, while the heme group 3460 may have fourteen data fields in the demographics category 3510. The categories and data fields of the medical group can be selected by a user to be present or not present.

After a template has been named and/or saved, the "Templates" module may prevent the user from switching the medical group of the template in order to prevent templates from overlapping and/or loss of data populated in the data fields. The system 100 may display a warning such as a red box 3520 in response to a user attempting to change the template's medical group after naming and/or saving the template. A dropdown menu of valueset options of some data fields may change between template medical groups. In some embodiments, the "Templates" module may allow cross population of data fields and/or categories between multiple template medical groups. In these embodiments, the data fields may be labeled and/or grouped by template medical group. For example, data fields unique to the solid tumor group 3450 would be marked to clearly differentiate from the data fields of the heme group 3460. As templates are improved or revised, the system may save each separate version so that a user can revert to a prior template version. Each version may store the content of the template, including the enabled data fields, the types of each field, the valuesets related to each data field, and the values related to each valueset.

Once the template medical group has been selected, the user can choose which of the data fields and/or nested elements of the data fields to present or not present in the template and to show or not show in the "Patient" module by checking or not checking a box 3430 by each data field name. Active fields can be marked by a checked box such as box 3530. A user may select or deselect all data fields in a category or template by checking or unchecking a select all box 3420.

Figure 36:
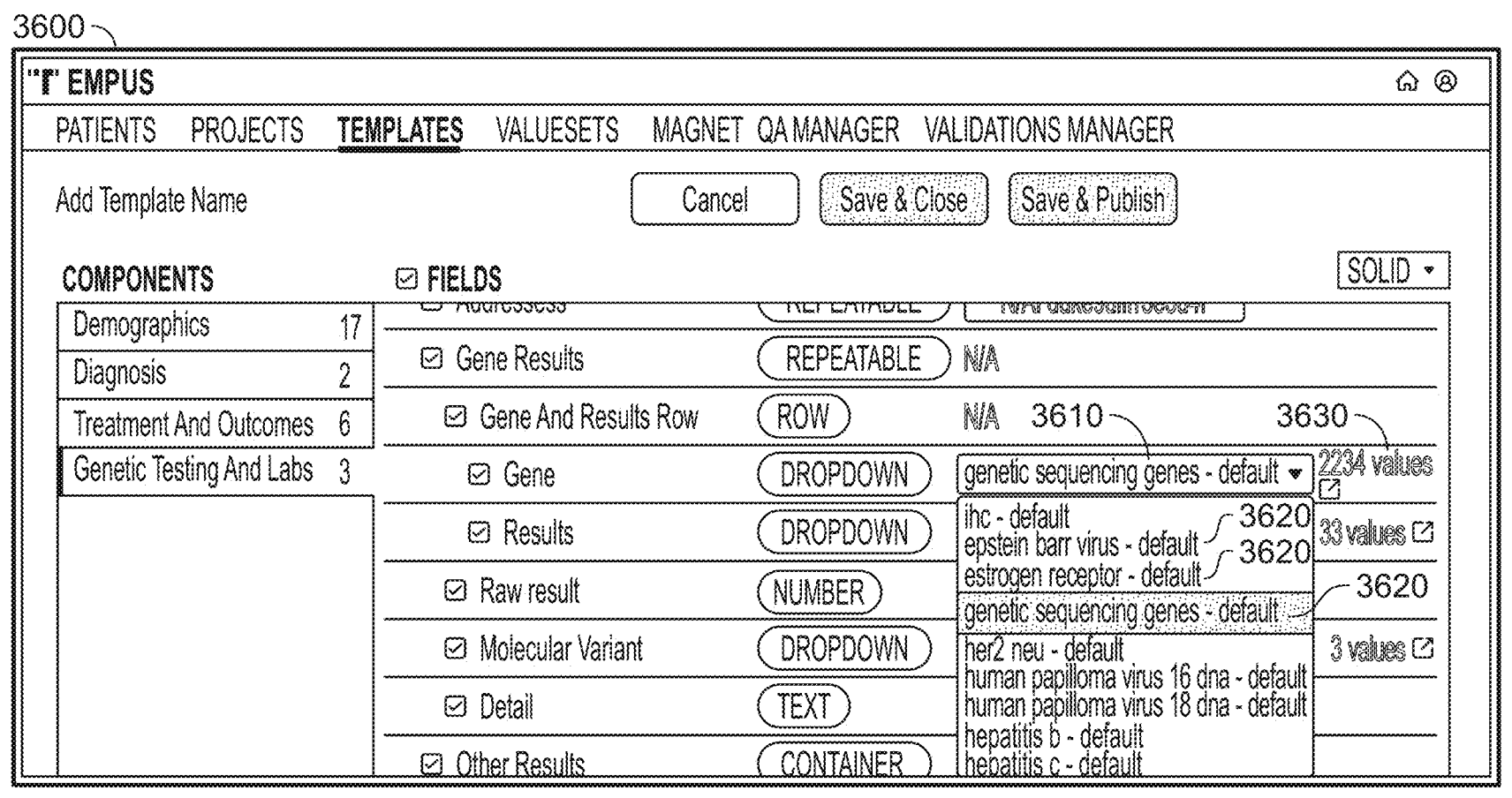
Figure 37:
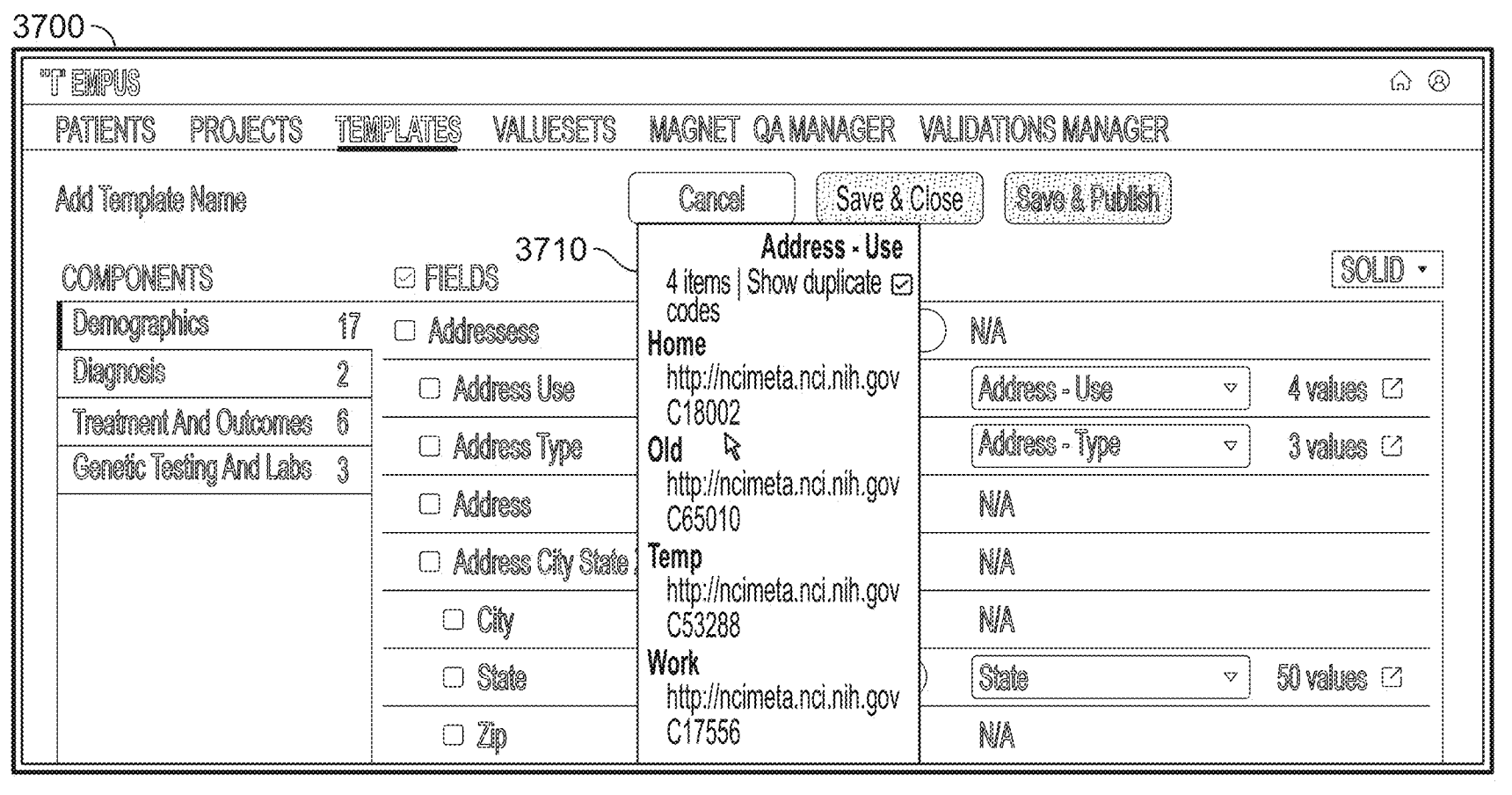
Figure 38:
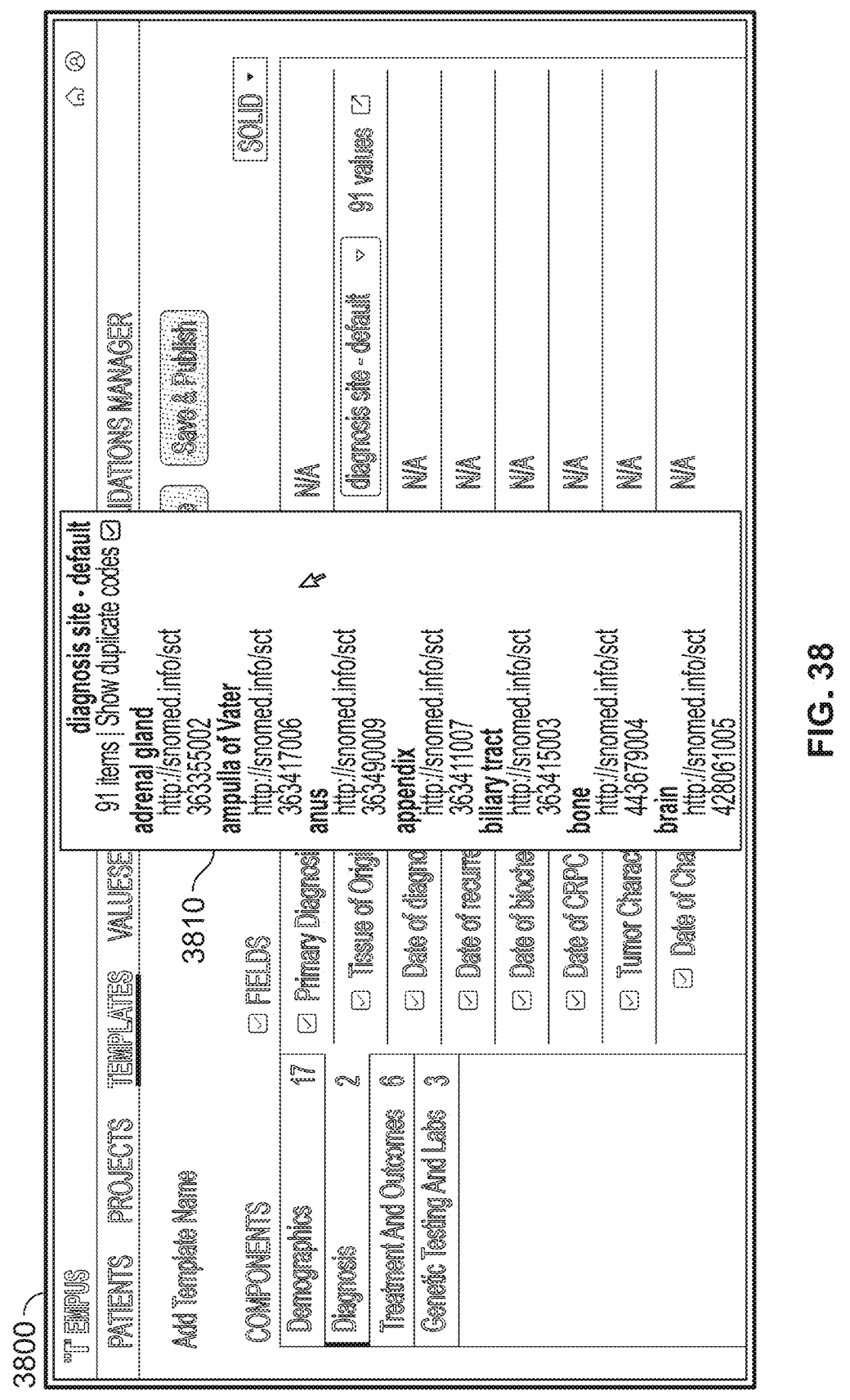

Referring broadly to FIGS. 36-38, GUIs 3600-3800 show details corresponding to the "Templates" module. Some data fields and/or nested elements such as the address use field may have a valueset dropdown menu 3610 with a one or more valuesets 3620, each valueset 3620 having a set of values for populating the data fields that an abstractor can select from when populating the data field using the "Patients" template. A valueset size 3630 of the selected valueset 3620 can be displayed near the valueset dropdown menu 3610. The actual values 3710, 3810 of the selected valueset 3620 may be viewed by a user by selecting the valueset size 3630 on the GUI (e.g., GUI 3600, 3700, 3800).

With respect to FIG. 36, the "genetic sequencing genes—default" valueset is selected. This valueset has 2234 values, with each value representing a specific gene that may be abstracted from a medical record, such as a genomic sequencing report. Valuesets may be amended to add, subtract, or modify their associated values, and re-saved with the modified values for further use throughout the system.

For instance, as shown in FIG. 38, a portion of values in the "diagnosis site—default" valueset are displayed in a pop-up window. The values include a description of the diagnosis site and an associated URL with a SNOMED code associated to the diagnosis site. It should be apparent that the values may contain more than as many type or quantity of data fields in order to sufficiently characterize the value, including but not limited to text descriptors, number descriptors, URLs, FHIR elements, and so forth.

A valueset can be selected for certain data fields and/or nested elements in order to help the abstractor find values more efficiently. Some values in data fields or nested elements such as a gene nested element can be associated with one or more other data field values such as a testing provider or test method, which can be used to filter the number of gene options available to the abstractor using the "Patients" module. Certain genes may only be associated with certain testing methods, and eliminating non-associated genes reduces the lookup time for the abstractor.

Figure 39:
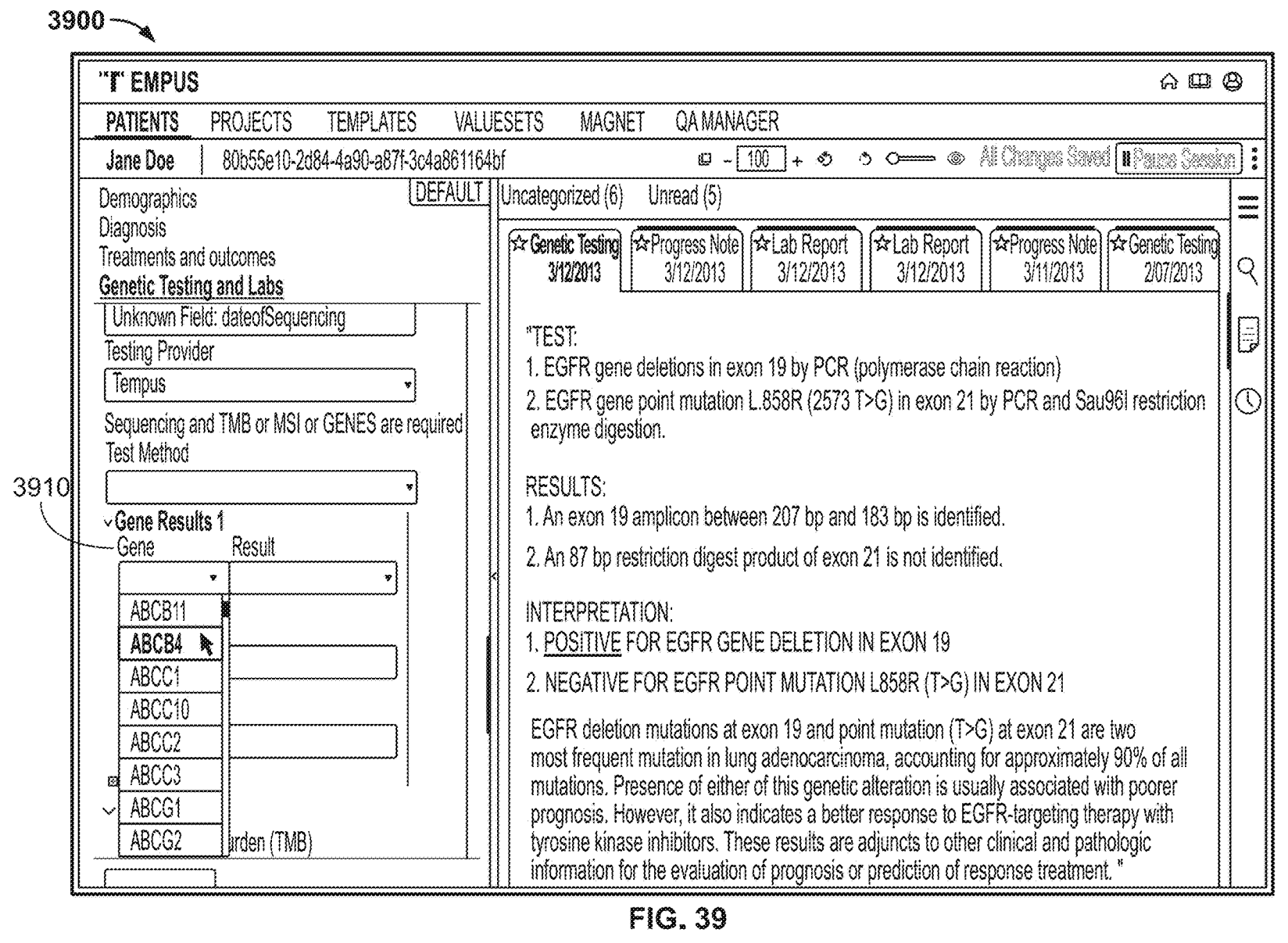

Referring to FIG. 39, GUI 3900 can display the values of the chosen valueset for certain data fields using the "Patient" module. Some data fields 3910 such as the gene data field may have over two-thousand values in a given valueset, as one example. A user with proper access to editing valuesets can select the values available for the data field or nested element by modifying a valueset associated with the data fields using the "Valuesets" module. Certain users such as administrators with sufficient privileges may be able to add new fields and/or modify the corresponding attributes of the valueset associated with the field. Different valuesets can be selected in order to reduce the number of options available for the abstractor for certain data fields and/or nested elements such as the gene nested element.

Figure 40:
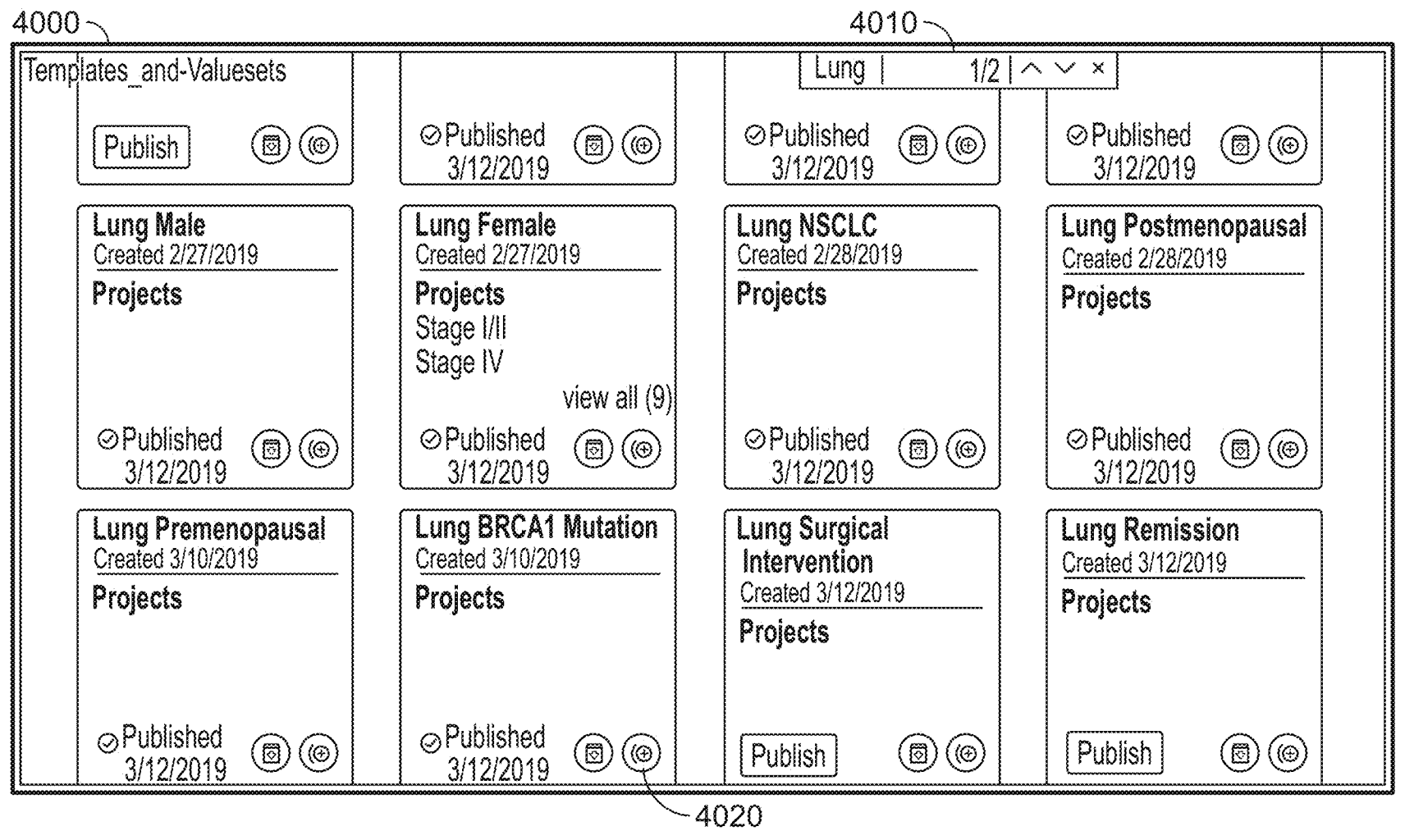
Figure 41:
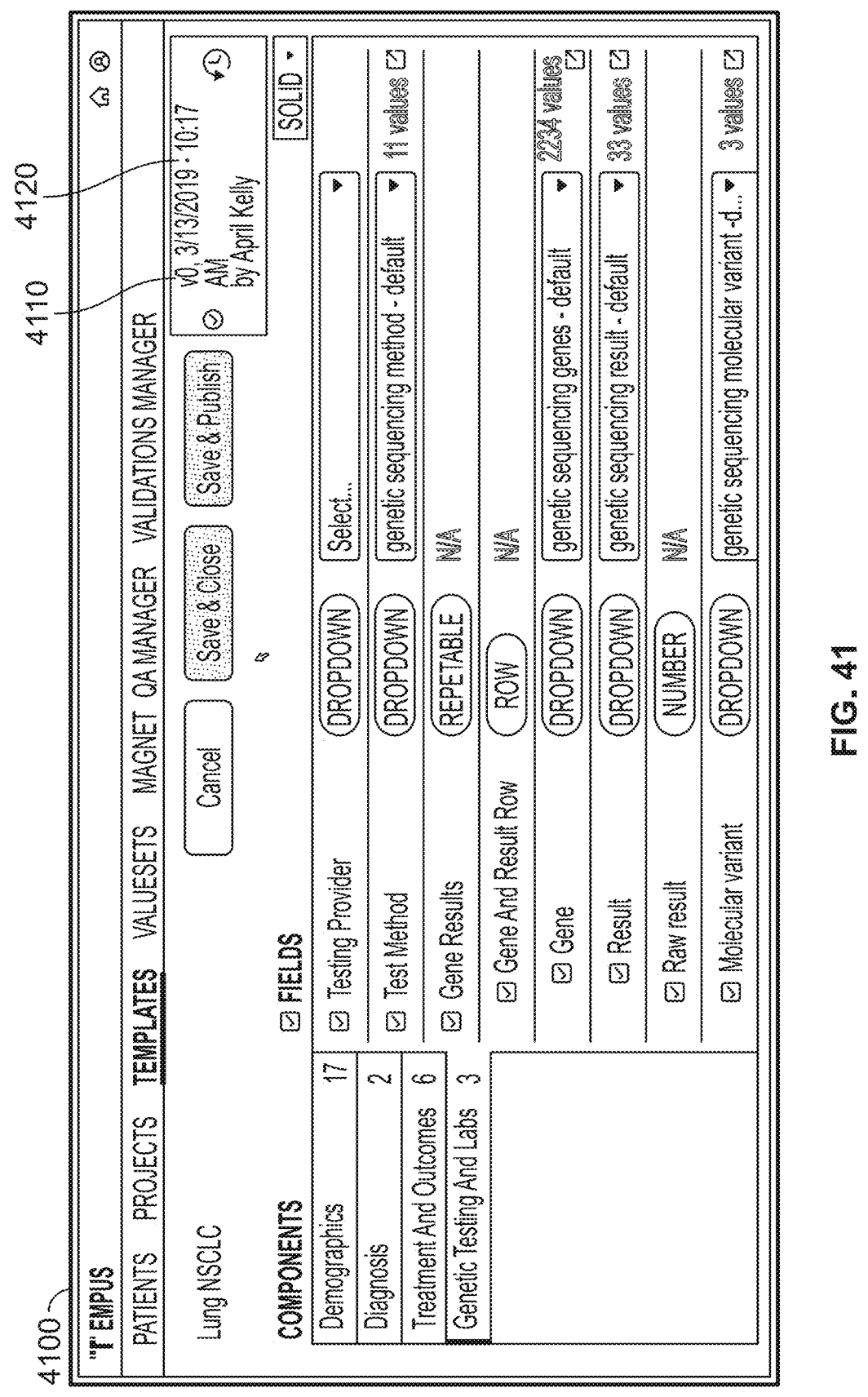

Referring broadly to FIGS. 40-41, GUIs 4000, 4100 can have a search function box 4010 in the template module to better find module, data fields, or another item of interest in the module more quickly. Templates may have a clone button 4020 to copy the template's data fields and other characteristics to a new template and thus create the new template more quickly. Multiple versions of the template can be automatically or manually saved during the modification of the template in order to preserve a history of the modification of the template. A version number 4110 of the most recently saved version of the template and/or a time 4120 that the version was saved may be displayed. Each template may displayed in a manner that shows projects which rely on that template. For instance, the "Lung Female" template has a "Stage I/II" project, a "Stage IV" project, and nine other projects that utilize the template.

Templates can be stored within an open source platform (e.g., FHIR), and can generally be accessible by URL. The platform can be used to represent molecular and clinical data in a uniform, consistent, and portable manner. Each template can have a corresponding URL, and can include related code definitions. This can allow templates to be shared with any number of third parties that uses the open source resource, allowing secure sharing of templates. Templates may comply with multiple open source platforms in order to be shared with even more third parties.

Figure 43:
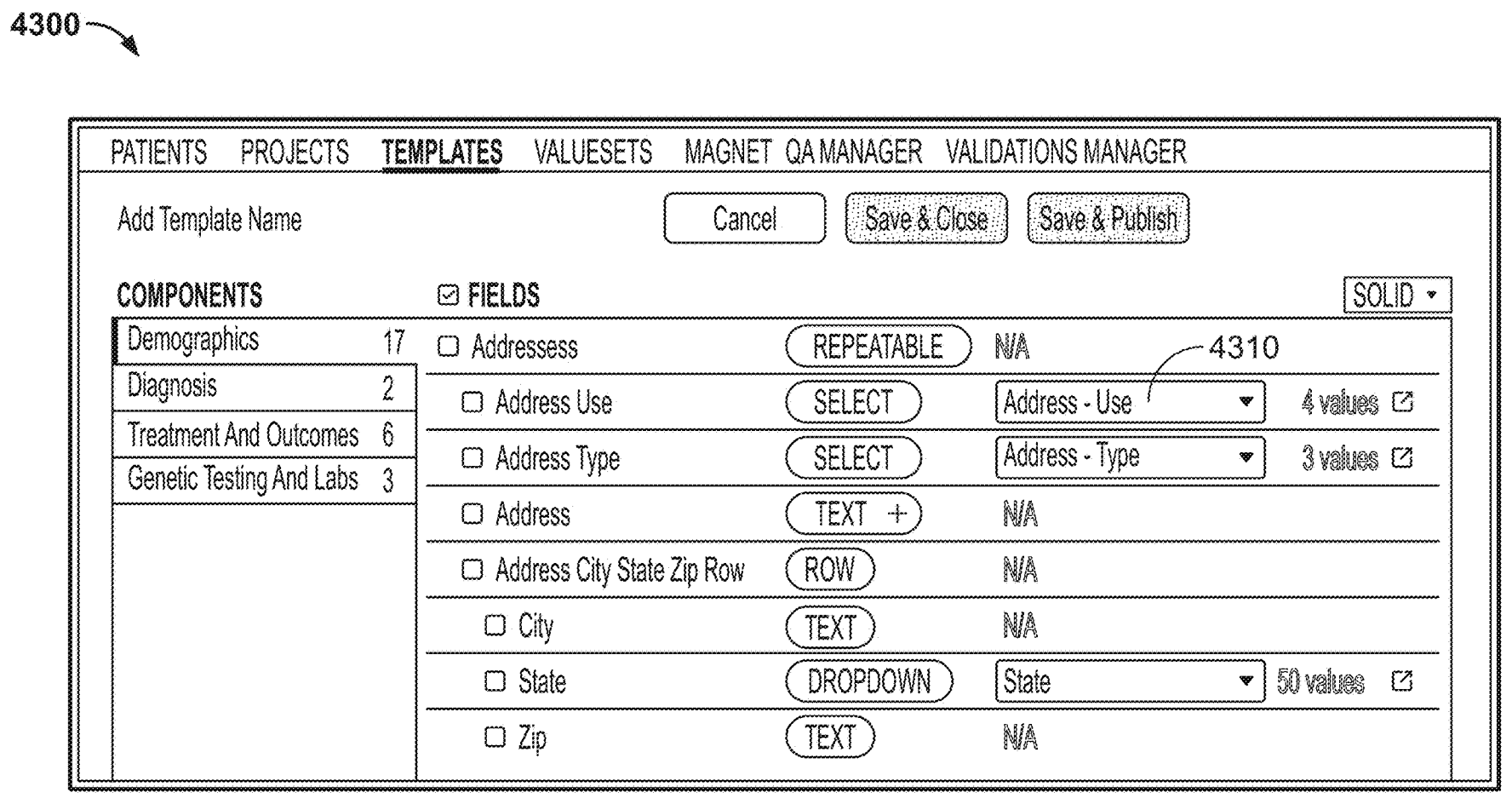

Referring broadly now to FIGS. 42-48, GUIs 4200-4800 show details corresponding to the "Valuesets" module, according to some embodiments. FIG. 42 shows an example valueset 4210 entitled "Address—Use," according to some embodiments. Address—Use 4210 can, for example, be stored within an open source platform (e.g., FHIR), and can generally be accessible by URL. The platform can be used to represent molecular and clinical data in a uniform, consistent, and portable manner. Each valueset can have a corresponding URL, and can include related code definitions 4220. As shown, for example, "Address—Use" 4210 includes code definitions related to home, work, old, and "temp," all within the context of addresses. Every valueset can have a distinct ID. Adding a code to a valueset can retroactively make all new entries available in every instance of the valueset call from the abstraction portal (e.g., via a template). In some embodiments, the code can be associated with an external system (such as a dictionary from SNOMED, GCNU, etc.) or a custom and proprietary system as in TEMPUS. These entries are visible in a dropdown from the abstraction portal for that particular field. As shown by FIG. 43, the "Address—Use" valueset 4310 can be included in a listing of demographics-related templates. Notably, the valueset 4310 is indicated as having "4 values"—which aligns with the four codes (home, work, old, temp) shown in FIG. 42.

In some embodiments, multiple systems can be combined to create a robust valueset. Abstraction could include, for example, genes from HUGO, TEMPUS, COSMIC, etc. By allowing the integration of all systems in one valueset, system 100 can provide quality, meaningful results without having to maintain convoluted combined datasets, or require unique fields associated with only a single dataset from a single system. System 100 can include valuesets for every data field, and not all have an external database. Accordingly, valuesets without an external database can be assigned an internal representation with unique codes.

Figure 44:
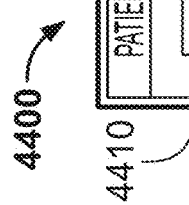
FIG. 44 is another image of an example graphical user interface (GUI), according to aspects of the present disclosure.
Figure 45:
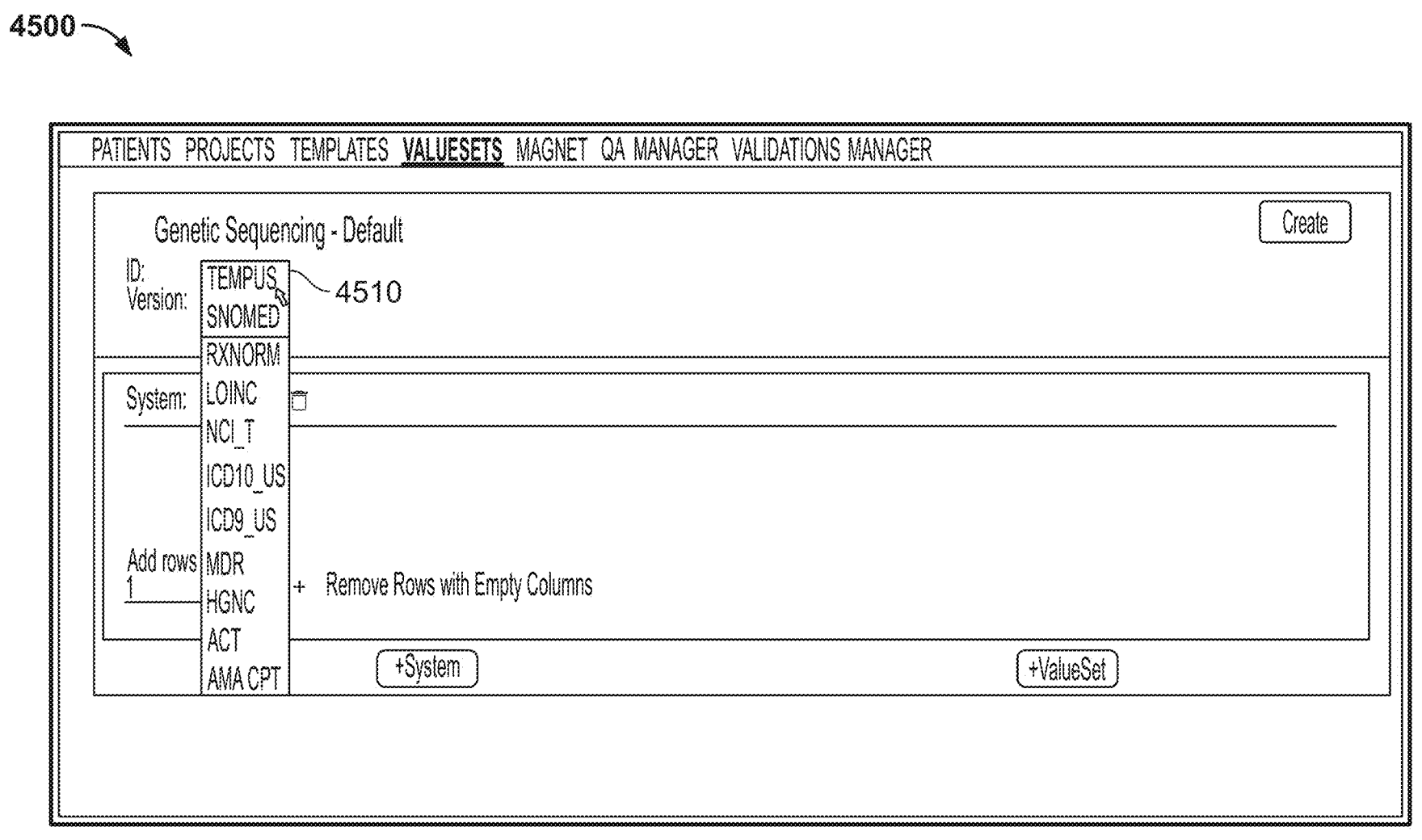

Referring to FIG. 44, a list 4410 of exemplary existing valuesets within system 100 is shown via GUI 4400. Selecting a valueset can show additional details for that particular valueset. Additionally, new valuesets can be created by system users. A user can create a valueset, and when a system (e.g., a third party data system) is subsequently selected, all codes tied to that system may be imported to memory. As an example, FIG. 45 shows a new valueset entitled "Genetic Sequencing—Default" with a dropdown menu 4510 of various known systems. A user can select a desired system, such as HUGO, for example.

Figure 46:
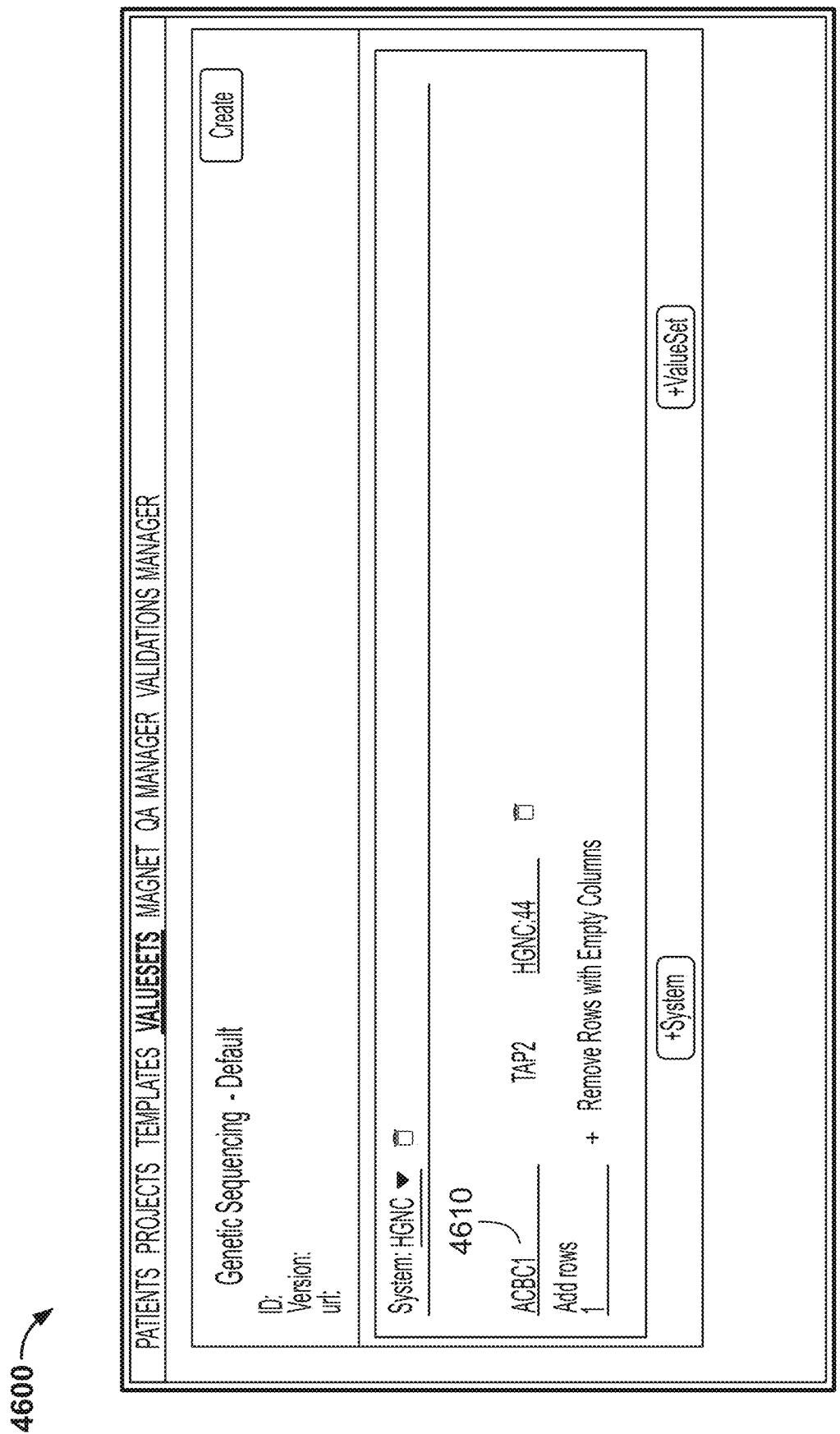
FIG. 46 is another image of an example graphical user interface (GUI), according to aspects of the present disclosure.
Figure 47:
FIG. 47 is another image of an example graphical user interface (GUI), according to aspects of the present disclosure.
Figure 50:
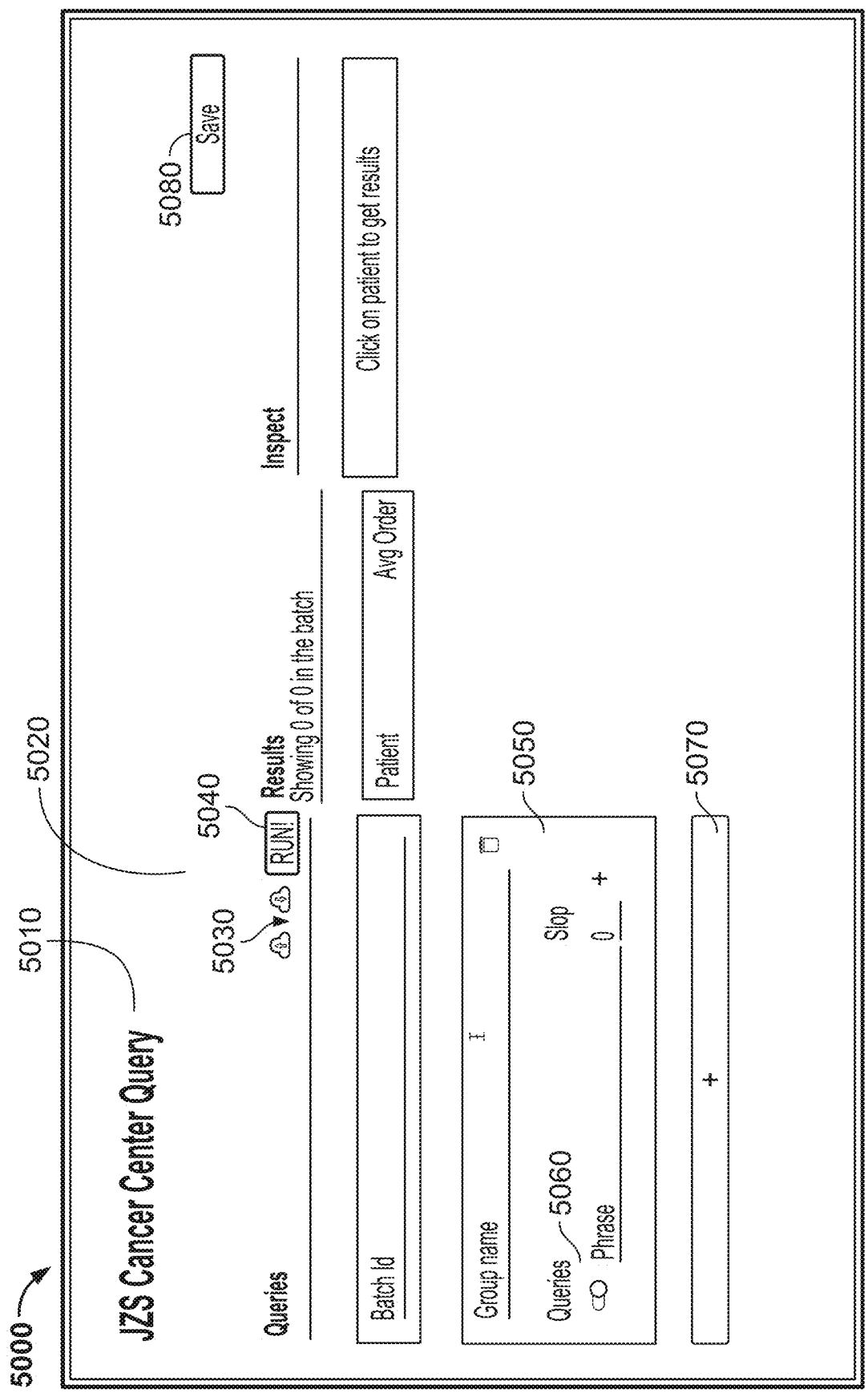
FIG. 50 is another image of an example graphical user interface (GUI), according to aspects of the present disclosure.
Figure 67:
FIG. 67 depicts one example of a user interface through which a manager-level user can view and maintain validations, quickly determine which patient cases have passed or failed, obtain the specific detail about any failed validation, and quickly re-assign cases for further manual QA and issue resolution prior to clinical sign-out and approval.

Referring now to FIG. 46, a user can add rows 4610 within the valueset. In some embodiments, a user can input a common term into each row 4610 (here, ABCB1, corresponding to a specific gene). As shown by FIG. 47, system 100 can output a corresponding code definition 4710 that relies on the user's input, as well as the desired system (e.g., HUGO). As an example, system 100 is shown to output "HGNC:40," which corresponds to HUGO's nomenclature for ABCB1. In some embodiments, system 100 can import all codes from an external system without the user having to type each entry. Further, in some embodiments, system 100 can provide dynamic representation of codes, meaning, auto-population of the name, the ID, or both from a partial name or partial ID can occur.

Accordingly, in some embodiments, the valueset, the codes, internal name, and a reference name from any external source of the dataset can by synced within system 100. This enables efficient assignment of human readable values in the valueset to the system-important code designation that can be meaningful to data curation, abstraction, analysis and research, and/or algorithms.

Figure 48:
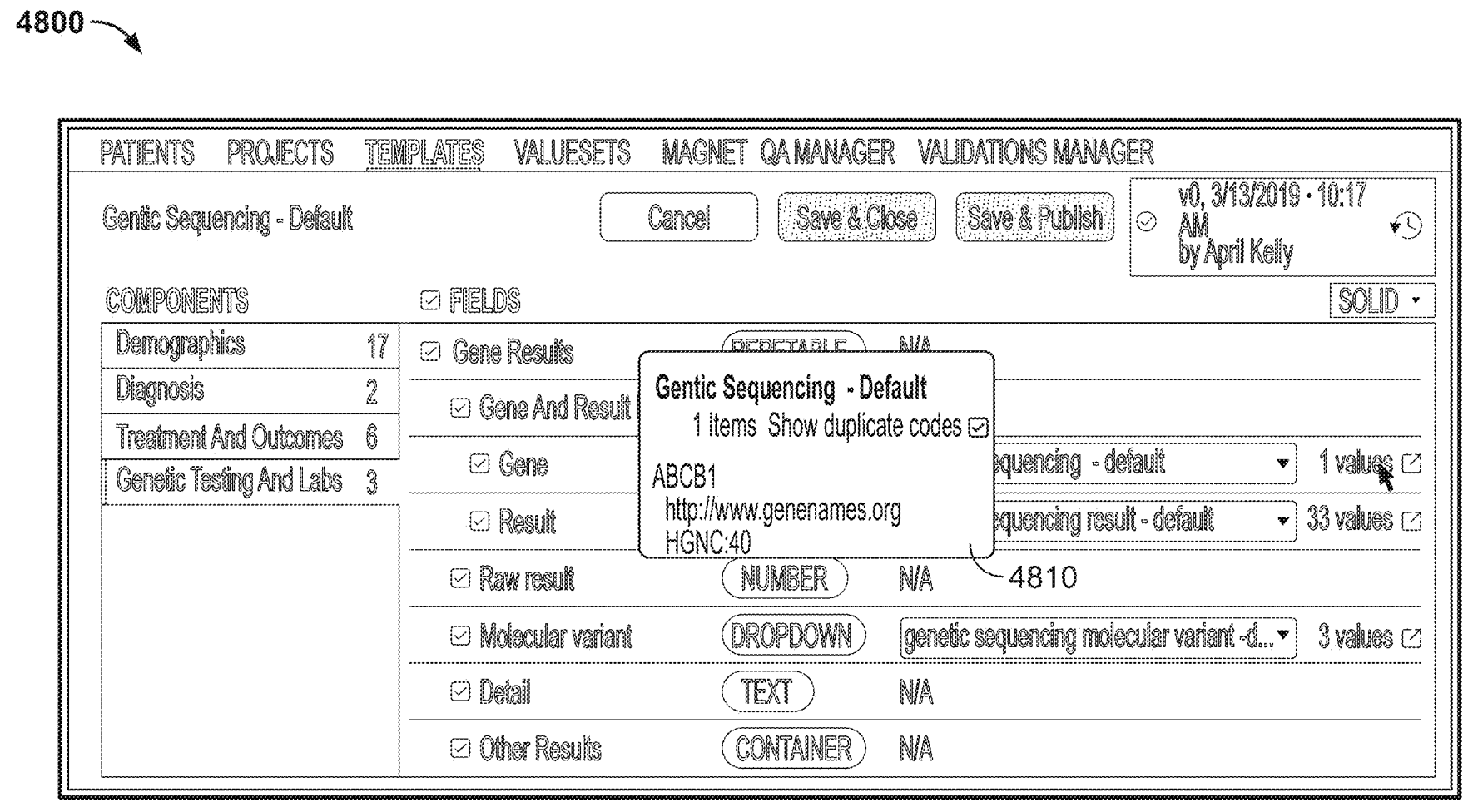

Still referring to FIG. 47, a user can save the new valueset, which can prompt system 100 to assign a new valueset ID, set the version to 0.0.0 (or as appropriate based on major/minor version changes), and assign a URL to the valueset based on the valueset name. The saved valueset can be added to the template system for selection, and any changes to the valueset can be propagated to all templates that utilize that valueset. As shown by FIG. 48, the new valueset "Genetic Sequencing—Default" can now be accessed via the system templates. When selected, the corresponding data 4810 can be displayed (e.g., which genes are included, code, name, etc.).

As described above, a workflow management system/software can do the orchestration of file upload and saving files to storage (e.g., a permanent document storage). There can be a number of metadata tags that come along with new documents, for example, file type, file extension, file size, etc. Once the document(s) are communicated to storage, additional processing can occur. In some embodiments, the workflow management system/software can determine if each document should be converted to a particular format, if optical character recognition (OCR) can be utilized, etc. Once this optional formatting occurs, the output can be provided to a search/analytics engine. In some embodiments, the search/analytics engine can be a commercially available product, such as Elasticsearch®.

The search/analytics engine can store each document, all of the related insights, all of the known information about each document, and/or scoring certain criteria for the attributes in the clinical text. In some embodiments, raw data content can be provided into a main element of the search/analytics engine, with metadata then stored on top. In some embodiments, words extracted from the document during OCR can be stored in a list, array, or other data structure, alongside the document in the search/analytics engine, which can allow searches to be run on the documents more quickly as will be explained below.

In some embodiments, access to the search/analytics engine can be limited to application accounts. Authorization service can be used, and access restrictions can be enforced at the user role level. The search activity, and even the ability to see the GUI can be controlled by various permissions at the application level. Accordingly, system 100 can't perform the look up by responding to actuation of the run button, unless the application and/or the user is sufficiently credentialed.

FIG. 49 is a graphical user interface (GUI) 4900 that can be implemented in system 100 to manage a number of operational tasks, and specifically, to enable clinical data structuring and abstraction work on a large scale. In some embodiments, GUI 4900 can include several modules as part of a manager console. As shown, the GUI 4900 can include a module that enables user search of a large repository of protected health information documents. In some embodiments, the GUI 4900 (within, for example, system 100), can provide for searching particular keywords or other phrases, and subsequently return a list of patients whose documents potentially match the search terms. In some embodiments, the returned documents can be analyzed by a person (e.g., a data abstractor) for further analysis, data structuring, and other purposes.

In some embodiments, the GUI 4900 (e.g., via the system 100) can identify patient cases of interest, before any structuring of clinical data occurs. In particular, system 100 can identify cases that match certain criteria, and then perform a responsive action. In some embodiments, the action can be extracting patient ID's for the purposes of analytics. Alternatively, in some embodiments, the action can be extracting patient ID's for clinical data structurers and abstractors. The data structurers and/or abstractors can subsequently review the specific cases that match the search criteria, and select a subset of cases for abstraction. Previous systems and methods required manual review of all clinical documents, typically one document at a time, with a user personally identifying patient ID's to include in relevant analytics.

Healthcare providers, in some embodiments, may supply large data sets for analysis via the system 100. Often, a subset of the larger data set needs to be structured. As one non-limiting example, a healthcare provider can supply all of their electronic health records, with the request for a data structure corresponding to a certain type of mutation. The mutation can be called out and/or described within unstructured or structured patient records. Additionally, the healthcare providers may request an analysis based off of the unstructured medical records. Such an analysis can identify patients who might be eligible for a clinical trial. Accordingly, the system 100 can conduct a first data search of unstructured documents within electronic health records. The GUI 4900 can output a patient list, for example, of patients who are likely eligible for the clinical trial.

Referring again to FIG. 49, a query homepage 4910 can include a plurality of query tiles 4920, 4930 that each represent an existing search query. Notably, queries can be re-run over time, and the search results can change based on new clinical documents, new notes, etc. Additionally, in some embodiments, a user can create a new query by selecting button 4940 ("Create New Query"). As shown, each query tile 4920, 4930 can include a query title (shown in bold), a creation date, and "batch" filtering data (when desired).

As used herein, the term "batch" can generally be defined as a subset of a complete dataset. As an example, implementing a "batch" search can provide an additional layer of filtering. In some embodiments, when there is no defined batch, the corresponding query can search all available data (e.g., across all patients, providers, facilities, etc.). Alternatively, when a batch is selected/defined, the data that is subsequently searched can be limited to that data subset ("batch"). A batch can be, for example, data received on a specific date, data received from a specific provider, input type (e.g., FHIR, HL7), source institution, integration type, trust level of the data, and/or score carding of the data. As shown in FIG. 49, a user can view all batches by selecting button 4950 ("List All Batches").

In some embodiments, the query title can be indicative of the characteristics that are being searched for. As one example, a query title can be "RET Fusion," and the query can search for RET fusion characteristics—characteristics of cancer that are found in a small minority of cancer patients, making clinical trial enrollment expensive and difficult. As another example, a query title can be "PIK3CA KRAS Mutations," which can be tied to pancreatic cancer. As another example, a user may input a query title corresponding to a key phrase which may be found within clinical documents or notes (e.g., "minimal residual disease"). In some embodiments, a user can nest and/or combine search terms to yield further focused results. Further, in some embodiments, the query title can correspond to a certain combination of drugs, or name associated with a drug regimen. A user can title queries as being focused on one or more particular biomarkers for one or more particular disease characteristics (e.g., HRD status), which might be indicated in the underlying unstructured medical record.

Referring now to FIGS. 50-55, additional illustrations of GUIs 5000-5500 are shown, according to embodiments of the present disclosure. User selection of the button 4940 can initiate the GUI 5000 to display a new query, via query tile 5020. In some embodiments, selecting a refresh button on GUI 5000 can allow a user to fill in a new query title. When saved, via selection of a button 5080, the new query tile 5020 can appear on the query homepage 4910. In some embodiments, a user can import previous query criteria, if desired. As shown, an example query title 5010 can be the name of the health care provider whose records are being searched, such as "JZS Cancer Center." The query tile 5020 can include a group tile 5050, a selection button 5070, and/or a query list 5060. The group tile 5050 can include a group name ("Drug Name"), a batch ID 5150, and the query list 5060. The query list 5060 can have one or more query entries that correspond to a search term/phrase. The batch ID 5150 can be blank, which can indicate that the full data set will be searched. Alternatively, a selected batch ID 5150 can indicate a subset of data that will be searched. Some projects may only have a single batch, which can allow the user to easily search for documents relevant to the project using the batch ID 5150 of the single batch. In some embodiments, a user can press the selection button 5070 to add a new group tile. Accordingly, each group can have multiple search phrases, and each query tile can have multiple groups, if desired.

Additionally, each query entry can include a slop number and/or a fuzziness number. As used herein, the term "slop" can generally be defined as how far apart words within search terms are allowed to be while still considering the document a "match," while "fuzziness" is how far letters within the search term are. For example, a search query with the search phrase "Aug. 1, 1991" may return a document with the phrase "August 1" or "August 1991" with a certain slop number. In another example, a search query with the search phrase "Aug. 1, 1991" may return a document with the phrase "Aug. 1, 1992" with a certain fuzziness number. In some embodiments, the selection button 5070 can perform a live call against a system data set (e.g., a search/analytics engine data set). Additionally, in some embodiments, a user can select an upload/download button 5030. The system 100 can upload existing search queries, if desired. Similarly, the system 100 can download queries to save for future reuse.

Each query entry may also include a maximum patient number. The maximum patient number can be used to limit the number of results returned by the search to no more than the specified maximum patients number. A batch may have thousands of documents containing the search phrase, and a user may wish to limit the results to a fraction of the documents.

Each query entry may provide a search language to the search/analytics engine in order to refine the results returned from the search/analytics engine. The search language may include a subset of words from a written language such as English, Spanish etc. The subset of words may include medical terms commonly used in documents about a certain medical disorder. For example, a search language used for a blood disorder may have words such as "hemophilia" or "von Willebrand" that may be commonly used in describing blood disorders but less common in everyday use. The query entry can select the search language based on a batch number, as the batch number may correspond to a project with a specific medical focus, or by the search term. For example, the query entry may provide a search language related to blood disorder if the search term is "von Willebrand." The search language can then be used by the search/analytics engine to adjust internal search parameter to return more relevant results to the user.

As shown, the group tile 5050 can have a query that includes a search "phrase" 5110. As one example, the search phrase 5110 can be "Herceptin." In some embodiments, using quotation marks within the search phrase 5110 can result in a system output corresponding to documents having an exact match to the search phrase 5110. Alternatively, using a search phrase 5110 without quotation marks can broaden the number of documents that will match. As one non-limiting example, the term "perception" may flag a document for review, simply based on the number of shared letters with the search phrase 5110 "Herceptin." In some embodiments, a certain character such as a "$" inserted at the start of the search phrase 5110 can result in a search being conducted with no fuzziness. Running searches without fuzziness may be desired when searching for specific stages of cancer, such as when documents related to "Stage III" are desired but documents related to "Stage II" are not.

In some embodiments, the query tiles, for example query tiles 5020 and 5120, can include a run button 5040, a results list 5130, and a save button 5140. When a user selects the run button 5040, the system 100 can run the search query and display the results list 5130. As shown, 89 patients have documents corresponding to the search phrase 5110. If a user wants to save a portion or the entirety of the results list 5130, they can select the save button 5140. As shown, the results list 5130 can include one or more search results 5250, which can provide additional detail when selected. As an example, FIG. 52 shows the GUI 5200 with the search result 5250 selected. In some embodiments, upon selection, a patient window 5240 can open. The GUI 5200 can include the query tile 5210, query list 5220, and/or results list 5230. The patient window 5240 can display high level information such as the query title, project name, status, document number(s), etc. In some embodiments, the system can run a separate search for each group tile.

As shown in FIG. 53, each result in the results list 5310 can include a selection box 5320. In some embodiments, an assignment button 5330 can be used to assign selected (e.g., via selection box 5320) results to a project. When a result is selected via the selection box 5320, inspection data 5340 can be displayed via the GUI 5300. The inspection data 5340 can include a document portion corresponding to the matched search phrase. In some embodiments, the desired search term/phrase can be shown in the inspection data 5340 using bold text, highlight, a different font size, etc. As shown, each entry within the inspection data 5340 can display identifying parameters, such as document number, file size, number of pages, document type (progress note, pathology report, etc.) page number (of the relevant document portion), and/or relevant phrase text. Notably, in some embodiments, a patient's data may be represented in the results list 5310 by a single entry. In contrast, a single patient may correspond to multiple documents shown in the inspection data 5340. Each document can be tied to a patient via a patient ID.

The system 100 may sort the results list 5310 by putting the most relevant documents at the beginning of the results list 5310 before displaying. In some embodiments, the system 100 may run separate searches for each group tile and then compare document ranks between group tile search results before displaying a final results list. In some embodiments, the system 100 may average the ranks of each document across multiple group tile searches and then order the documents by the determined average rank in the results list 5310. For example, the system may determine a document ranked first in a first group tile search and third in a second group tile search, and place the document second on the final results list. Polling search results from multiple group tile searches can normalize and/or better rank the results, as documents that consistently rank highly in various group tile searches will be displayed near the top of the final results list while documents that ranked highly in one group tile search but lower in many other group tile searched will not be ranked near the top of the final results list. In other words, this approach can help prevent outlier documents that may be less relevant from being displayed to a user.

Figure 54:
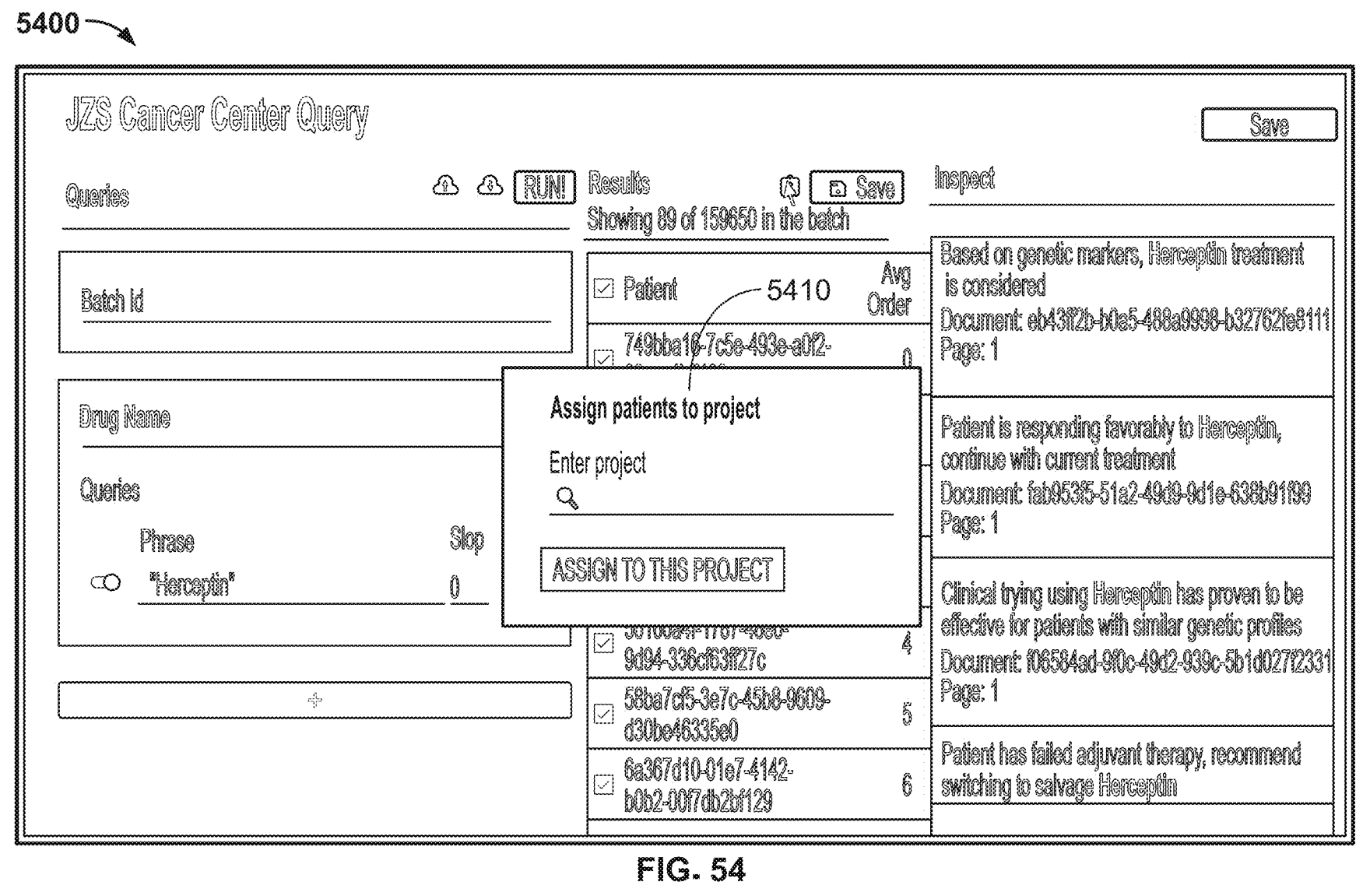

In some embodiments, selection of the assignment button 5330 can prompt a new data window within the GUI. As shown by FIG. 54, an assignment window 5410 can be displayed in response to selection of the assignment button 5330. Once a project is identified, each selected result from the results list 5310 can be added to the corresponding project workspace. In some embodiments, the assignment window 5510 can include a project search field 5520, which can update suggested projects as the user types out a search. A user can select a listed project via the assignment window 5510. As one non-limiting example, if a user were to select the "Cancer Center Lung" project, 89 new cases would then become available immediately for abstraction to clinical data structurers, and abstractors on their interface. In some embodiments, abstractors can then manually look at the documents that are in the project, followed by the actual work of data structure. Project types can include, for example, abstract patients for clinical pipeline, institution specific projects, and institutions that identify specific research areas.

Figure 56:
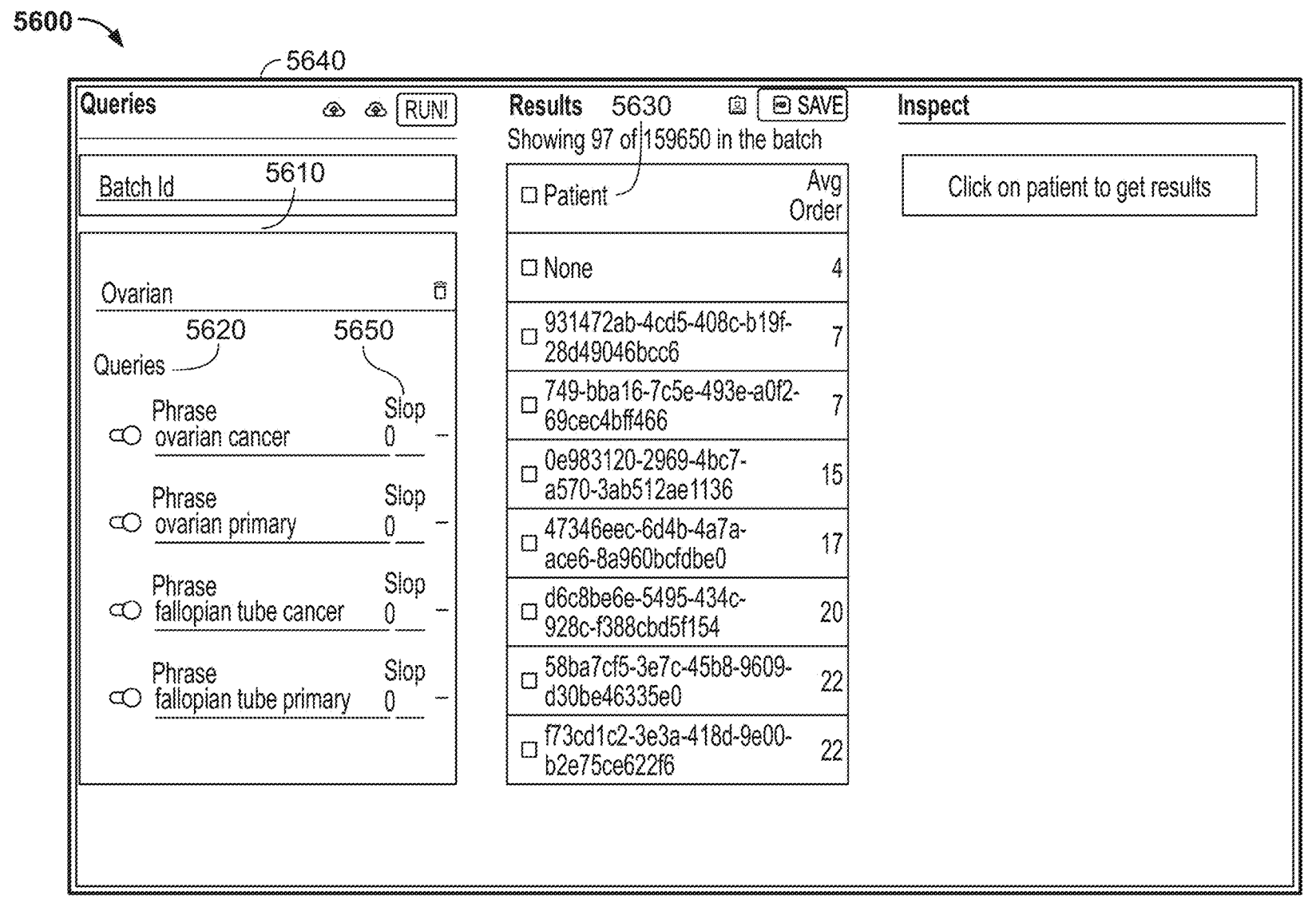

Referring now to FIGS. 56-58, additional illustrations of the GUIs 5600-5800 are shown, according to embodiments of the present disclosure. As one non-limiting example, the query tile 5640 can be directed to searching for a type of ovarian cancer. The group tile 5610 can include a title "Ovarian." The query list 5620 can include multiple phrases for searching. In some embodiments, phrases can include "ovarian cancer," "fallopian tube cancer," and variations thereon. FIG. 57 is shown to include a second group tile 5720. The group tile 5720 can include a title "Stage II-IV." In some embodiments, search phrases corresponding to group tile 5720 can include "stage $ii," and "stage $iia." Notably, within group tiles 5710, 5720, phrases are not within quotations, which can allow for non-exact matches within searched documents. As shown, slop numbers 5650 can be set to 0. In some embodiments, the results list 5630, 5730 can include each patient with at least one document that indicates ovarian cancer stages II-IV (i.e., conditions of both group tiles 5710, 5720 are satisfied). It should be understood that dozens or more of different phrases may be included in a single query, providing a powerful and flexible tool to permit differentiated searching of records. In other examples, the record set to be searched may be from a plurality of health care providers.

As shown by FIG. 58, the inspect data 5820 can include documents that potentially discuss ovarian cancer stages II-IV. In some embodiments, system 100 can provide an average order 104. The average order 104 can rank patient results based on defined search parameters. As one example, the search/analytics engine can perform scoring and/or ranking of results. The average order 104 can provide an indication of result quality. In some embodiments, for example, the average order calculation can consider the frequency of phrase appearance within documents, and/or the overall number of matching phrases within documents.

Thus, as described herein, system 100 is capable of efficiently capturing all treatment relevant data including disease state factors, treatment decisions, treatment efficacy and exploratory factors (such as factors that may have a causal relationship to treatment efficacy) and structuring that data to optimally drive different system activities including memorialization of data and treatment decisions, database analytics and user applications and interfaces. In addition, system 100 is highly and rapidly adaptable so that it can be modified to absorb new data types and new treatment and research insights, as well as to enable development of new user applications and interfaces optimized to specific user activities.

In another aspect, elements of system 100 may be further described in FIGS. 59-76. A comprehensive data integrity evaluation and validation system is described herein, the system usable, e.g., to generate a definitive clinical record for a patient or consistency among groups, projects, or cohorts of patients. Due to the quantity and varying intricacy or elements of a clinical record, multiple categories of basic and complex validations may be needed to provide the requisite completeness and accuracy. In the functionality described below, various authors use software tools to compose validation rules that can be run independently on one or more patient records or applied in aggregate to all patient records comprising a given grouping, project or defined cohort.

These validations can be applied to a specific attribute (e.g. gender) or to a combination of attributes (e.g. gender and primary diagnosis) that results in the authoring of basic and advanced rule-based logic. In particular, the system may include a dynamic user interface enabling a user to design and build a new query by selecting one or more attributes represented in the system and then associating a desired rule (e.g. is present, is above/below/within a certain threshold value or range, etc.) with those attributes. Validation rules can operate in a stand-alone fashion or can be chained and/or linked together at a project and/or patient cohort level.

The construction of these validations is performed through the selection of one or more existing query sets as part of a validation query and/or through the design of a new query. Alternatively, validation checks can also be grouped and bundled into query sets or used individually as part of an ad-hoc quality assurance check initiated either manually or automatically upon delivery of a cohort of patient data. Still further, the system may maintain the ability to programmatically seed and/or populate a predefined set of validation rules that may be applicable to one or more streams.

A validation rule may be composed of a seeded set of rules and/or checks that enable data integrity. From a system perspective, a series of API endpoints await a sufficiently articulated and valid rule definition as well as a corresponding validation rule name. The API for the service may enable the creation, update, and/or deletion of the validations; alternatively, the validations may be managed in an administrative user interface or directly via database queries.

In a separate transaction, the rule can be associated with a query set (a combination of validation queries) and/or a specific cohort of patients where it can be run automatically to detect data inconsistencies and anomalies. Query sets may be groupings of validation rules and checks that are grouped as a result of similarity in the types of checks performed and/or the needs of a quality assurance ("QA") user wanting to identify the integrity of patient records via use of bulk and/or combined validation rules and checks.

Applying a query set to a patient record or a portion thereof may result in the system verifying an accuracy of the data structuring within an acceptable system- or user-defined threshold level, in which case the structured data may be deemed accepted and the patient record may be amended to include that structured data. In another instance, the query set result may indicate the presence of one or more errors in the data structuring, requiring further review and/or modifications to the structured data, and the patient record then may be amended to include the modified structured data.

Structuring Data

In order to properly apply the validation rules, it may be necessary to standardize, normalize, or otherwise structure the input data. Thus, systems and methods are described herein that permit the automatic analysis of different types of structured clinical data. The structured clinical data may differ on the basis of the types of data elements within each list of structured clinical data, the organization of data elements within a structured clinical data schema, or in other ways.

Certain systems and methods described herein permit a patient's structured clinical record to be automatically evaluated and scored in a consistent manner, while also simultaneously allowing for the determination of data integrity across various data sources. In some aspects, inter-rater reliability and a comprehensive clinical data validation system facilitate the identification and resolution of gaps in a patient's record when abstracted across multiple disparate streams.

Certain systems and methods may be utilized within an overall clinical data structuring platform. The platform may include a workflow tool and an administrative user interface for querying, reporting, and output tagging.

In one aspect, the system may support externally sourced data validations and/or edit checks corresponding to custom data science analysis workflows as well as data integrity enforcement for various purposes, such as for clinical trial management. In this context, "externally sourced" may refer to validation rules or checks authored by one or more external parties, e.g., health systems, clinical trial management services, etc., importable and ingestible into the present validation system, for use and integration with other rules and/or validation checks. "Externally sourced" also may refer to ingestion of other validations originated by other individuals or applications other than the present validation system while still internal to the entity employing the present system.

Additionally or alternatively, the system may compare multiple sets of structured clinical data for a single patient, select the most correct data element for each of the structured data elements, and return a new list of structured clinical data containing the most correct data element value for each data element. The new list reflects a single "source of truth" for a patient based on the raw clinical data for that patient.

Certain systems and methods may make use of various systematic validation checks at multiple stages in a process that commences with raw data input and ends with the data being curated, including at a data abstraction stage and/or a quality assurance stage. Additional stages in this timeline may include a data sufficiency score-carding stage in which the raw inputs are analyzed to determine whether they contain a sufficient amount of clinical data to proceed with the abstraction stage, and a downstream stage in which validation checks are used for patient cohorts.

In certain embodiments, the structured clinical data may be merged into a larger dataset. The larger dataset may have the same or a similar data schema to the structured clinical data. The larger dataset may be used for the conduct of research, may be associated with published research or clinical guidelines, and may be provided to third parties for their own research and analysis.

Figure 59:
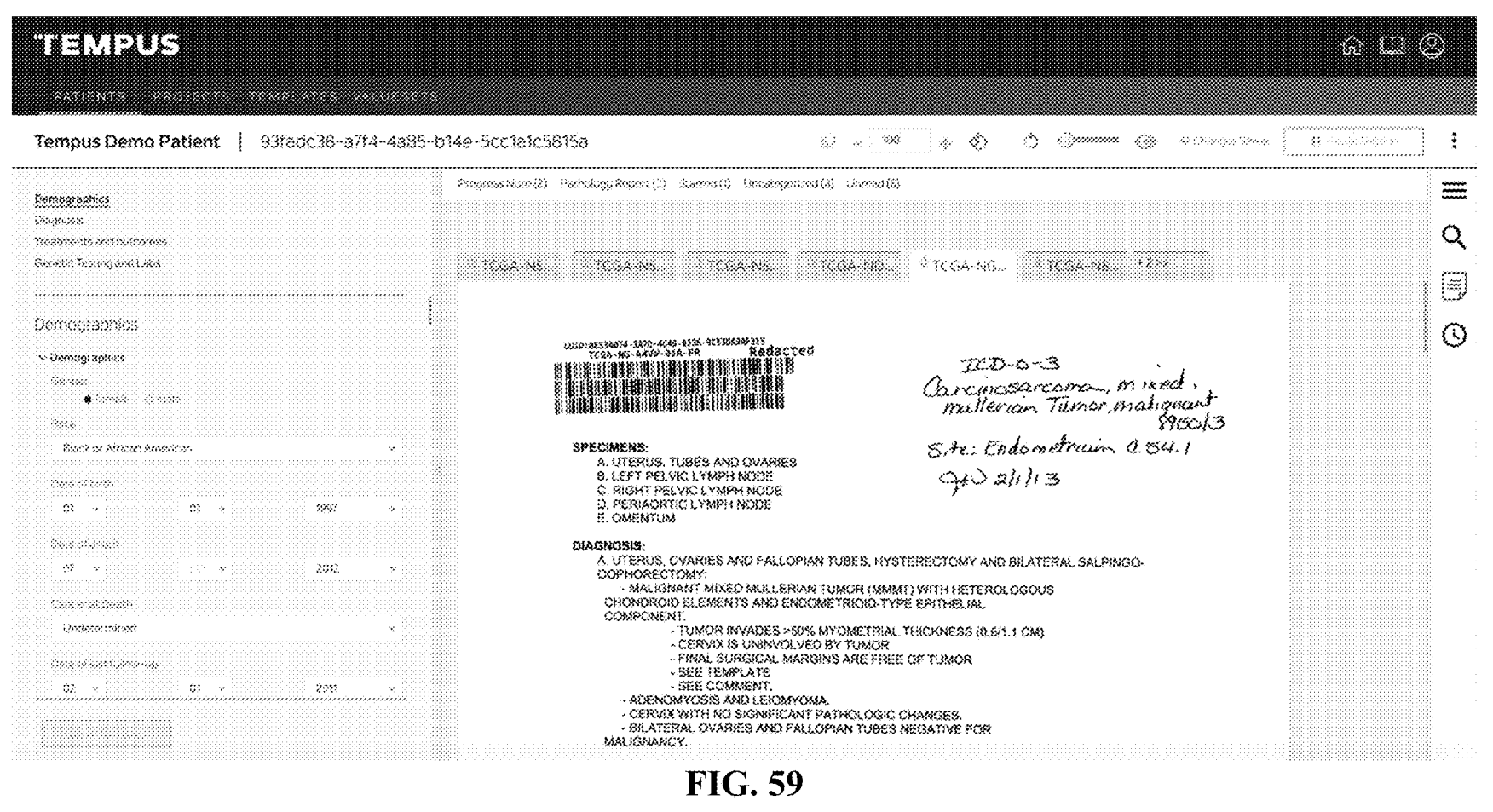

Turning now to FIG. 59, an exemplary user interface that a clinical data analyst may utilize to structure clinical data from raw clinical data is depicted.

In one aspect, the input data may be abstracted data that signifies a comprehensive, dynamic representation of a patient's clinical attributes across multiple categories, e.g., demographics, diagnosis, treatments, outcomes, genetic testing, labs, etc. Within each of these categories, attributes may be repeated to reflect multiple instances of a particular clinical data attribute present in multiple locations within the patient data.

In a second aspect, patient data can be extracted from source records, research projects, tracking sheets and the like. For example, sample source fields from unstructured flat files may include: enrollment_date, age_at_enrollment, sex, race, marital status, gravidity, menopause, cancer_status, age_at_diagnosis, laterality, T_stage_clinical, T_stage_pathological, histology, grade, etc., and the system may extract both the source fields as well as their respective data values.

In both aspects, the form of this input data often is inconsistent and dynamic to the principal investigator, researcher and/or partnering organization providing the patient data. As a result, a mapping exercise may be required to relate information from unstructured data originating in flat files into a canonical schema, format and/or model for evaluation purposes. In particular, the mapping exercise may identify source data fields and attributes from the data provider, e.g., a third party organization or researcher, and analyze that data in its raw form in order to determine linkages between the data and medical concepts or terminology reflected by the data and a data model used by the system. Such concept mapping may be performed manually by specially-trained informatics engineers or other specialists or one or more software applications specifically designed to undertake such mapping, as would be appreciated by one of ordinary skill in the relevant art.

In a third aspect, patient data may be Electronic Medical Record (EMR)-extracted structured data. This data can include a set of text strings representing various clinical attributes but may also include various ontological code systems and concepts to represent each text string in a way that can be compared against other data sets and/or validations. As a result of this structuring, the data mapping exercise may be significantly more straightforward than the exercise required for either of the other two instances. FIG. 60 depicts one example of EMR-extracted structured data that includes a payload of diagnosis-related data, specifically, data pertaining to a diagnosis of Malignant neoplasm of larynx, unspecified. Similarly, FIG. 61 depicts one example of EMR-extracted structured data relating to the medication Paclitaxel, provided intravenously.

In a fourth aspect, patient data may be extracted through a clinical concept identification, extraction, prediction, and learning engine such as the one described in the commonly-owned U.S. patent application Ser. No. 16/702,510, titled "System and Method Including Machine Learning for Clinical Concept Identification, Extraction, and Prediction," the contents of which are incorporated herein in their entirety. The output of this engine may be a configurable and extensible set of predictions about a given patient's clinical attributes across a variety of content types. These types may include (but may not be limited to) primary diagnosis & metastases sites, tumor characterization histology, standard grade, tumor characterization alternative grade, medication/ingredient, associated outcomes, procedures, adverse events, comorbidities, smoking status, performance scores, radiotherapies, imaging modality, etc.

Triggering Analysis Once Data is Structured

In order to make use of data from one or more of these streams, the system may be configured to automatically initiate the evaluation of both partial and fully structured patient clinical records across multiple sources and/or streams through a variety of triggering events. Such events may include, e.g.: (1) receiving an on-demand request, e.g., via an Administrator-driven user interface that can initiate the process programmatically, (2) via a background service triggered upon receipt of new software code commits or corresponding application build phases, (3) when new data is either received or ingested across sources and streams, (4) upon achieving a sufficient inter-rater or intra-rater reliability scoring system, which is run automatically on a configurable percentage of patient records as part of a project or batch, (5) upon completion of either a case abstraction and/or QA activity, (6) upon receipt of clinical data and/or records for patients participating in an institution's clinical trial, which may be obtained via a site coordinator, via EMR or source records, or (7) real-time analysis during creation of a patient note or other clinical data. Each of these trigger events is discussed in greater detail, as follows.

Trigger #1 (on-demand): a user with appropriate authorization can manually initiate one or more distinct tests to support the evaluation of one or more patient clinical records. In its default state, this functionality manifests itself as part of a graphical user interface presented after entering in a specific request for one or more tests at a terminal window command line.

Trigger #2 (on receipt of code commits): tests can be initiated en masse via a background service or selectively when only a subset of tests are required to validate specific patient clinical data and/or attributes. In this aspect, validation may take advantage of "continuous integration," or the practice of integrating new code with existing code while embedding automated testing and checks into this process to minimize and/or eliminate gaps and issues in production-level software and applications. As part of this process, new code commits are made, reviewed, approved and merged into various code branches for subsequent application build phases while intermediate software (e.g. Jenkins) maintains responsibility for running one or more test suites programmatically and recording their output (e.g. failed, pending and passed) as well as collecting details, stacktraces and/or screenshots resulting from these tests.

Trigger #3 (new data ingested): an integration engine and/or intermediate data lake receives and processes new structured data which may also initiate corresponding tests to evaluate and score the data as its own distinct stream as well as comparatively to any existing data received for the patient. In one possible implementation, an integration engine may receive a stream of XML and/or JSON content comprising structured data and corresponding ontological code systems and concepts as extracted from a health system's EMR at a single point in time. Upon receipt, this data would be evaluated against one or more test suites for accuracy, coverage and/or insufficiency. It may also be compared and evaluated relative to other patient record data received via other sources and similarly run through one or more test suites. In another possible implementation, the system may receive a FHIR-compliant payload from partners that contains one or more genetic/genomic testing results for one or more patients. In this example, the test suite for genetic testing referenced above may be run programmatically to evaluate the integrity of this data and may also be compared and evaluated relative to other genetic testing content already ingested and/or abstracted as part of one or more patient records.

Trigger #4A (inter-rater reliability): the system will evaluate two instances of a patient's abstracted clinical data and compose a score at both the case and field-levels to determine a level of agreement between the a plurality of abstractors (or "raters") in order to determine whether to automatically begin the evaluation process. In this example, "automatically" may refer to a systematic assignment of a subset of patient cases that will be abstracted by two distinct individuals in a "double-blind" manner where the reviewer may also be unaware of participant identities. Further, a scoring scheme is used to calculate the proficiency and accuracy of each submission by taking into account the modifications and updates made by a conflict resolution user.

The system may assign a first version or instance of a case or data stream to a first rater and a second version or instance of the case or data stream to a second rater, i.e., the plurality of raters may review the same subset of cases or records, after which the system may determine whether there is a sufficiently high degree of overlap and/or agreement between each rater's abstraction. When the requisite threshold is not met, a third-party conflict resolver may review the raw clinical data and each rater's abstraction content in order to generate a de facto or "best" abstraction of the patient record. In one aspect, the conflict resolver may select from among the abstractions provided by the other raters. In another aspect, the conflict resolver additionally or alternatively may provide its own abstraction and select the "best" abstraction from the group that includes its own abstraction and those of the other raters.

Figure 62:
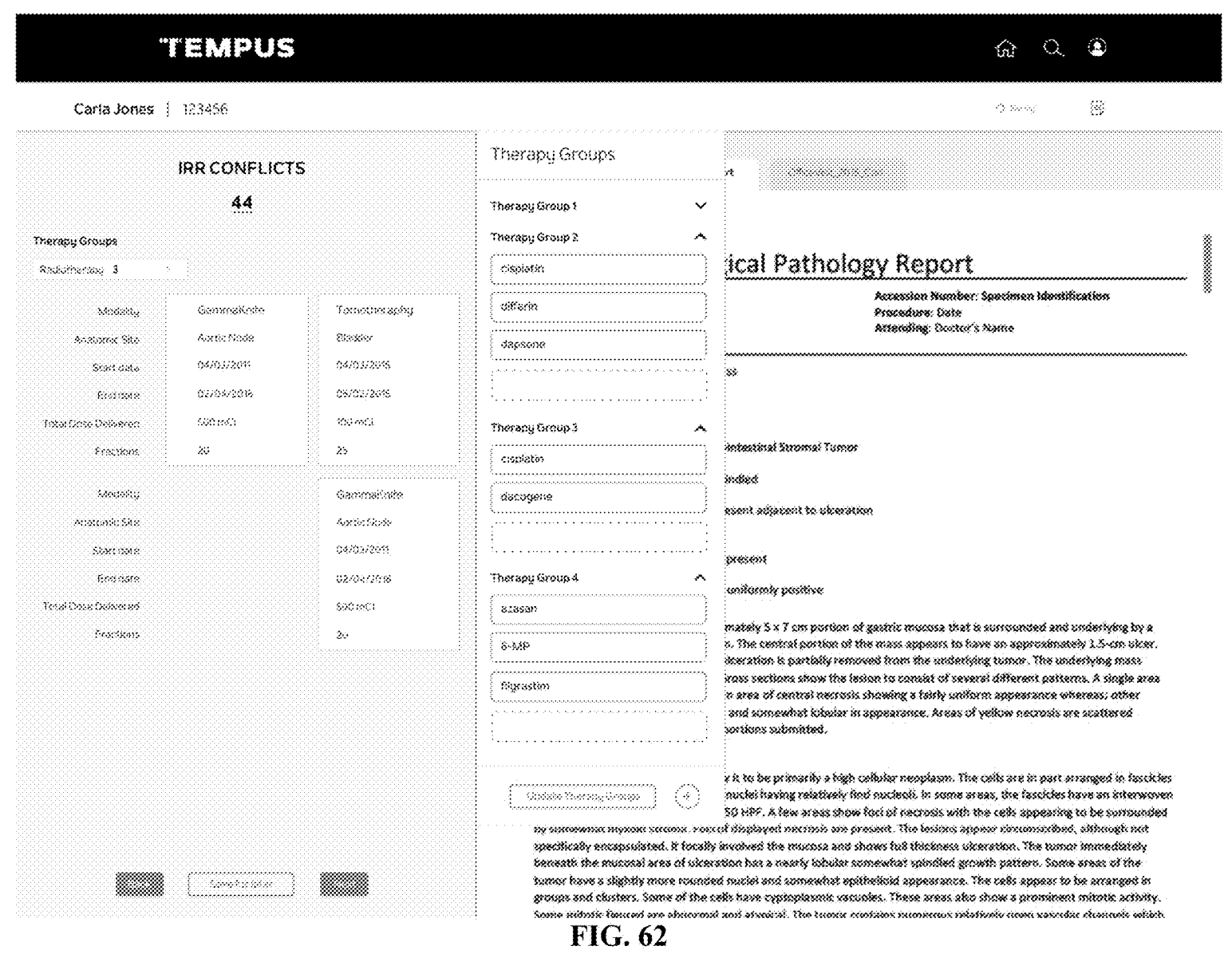

With regard to this trigger, FIG. 62 illustrates one of the steps to be performed by a conflict resolution user when a complex disagreement is identified for a patient record. In this example, a conflict resolver must evaluate the radiotherapies cited by the two abstractors and determine which are in fact appropriate for the "de facto" patient clinical record by moving the most correct items to therapy groups.

Figure 63:
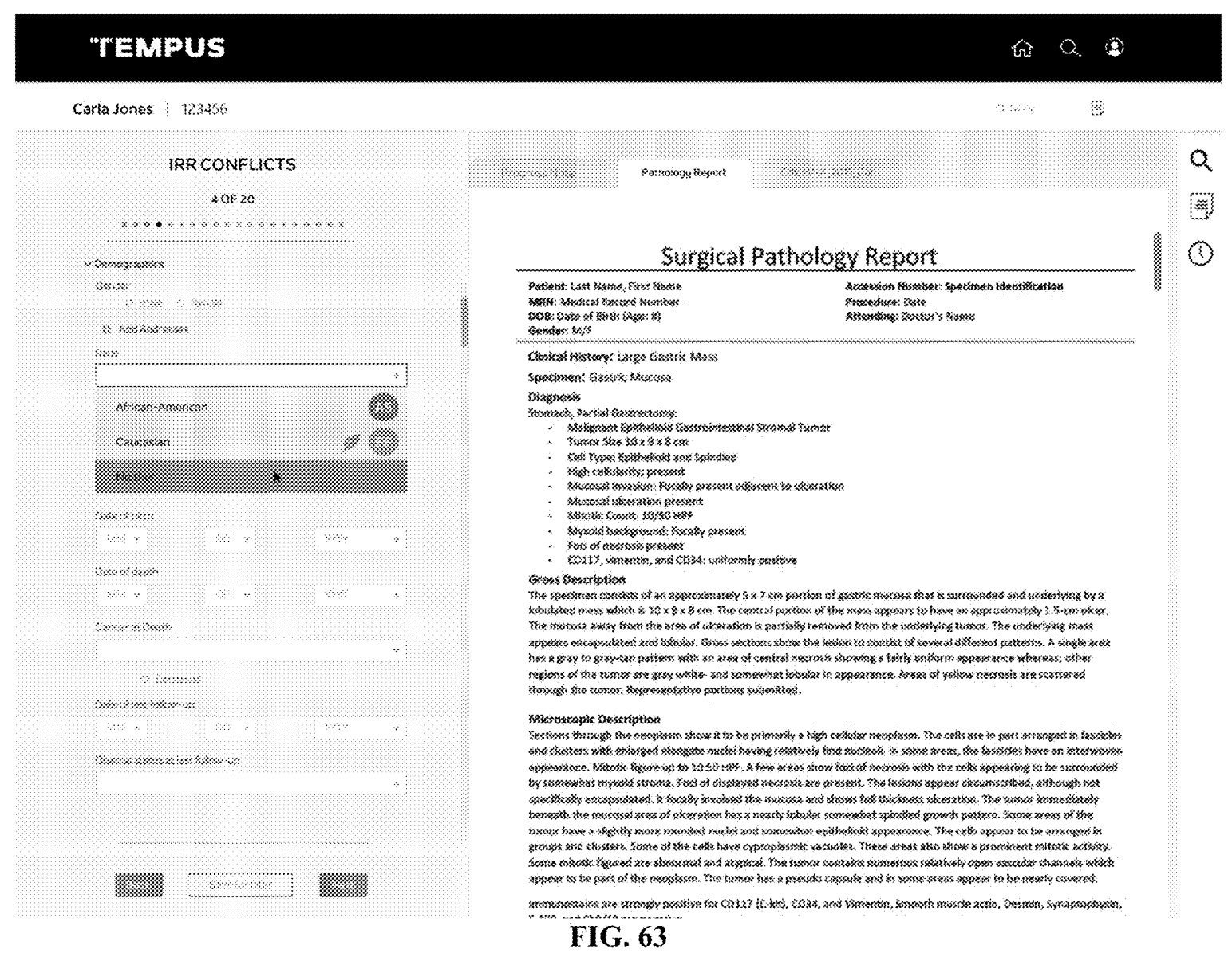

Conversely, FIG. 63 illustrates one of the steps to be performed by a conflict resolution user when a basic disagreement is identified for a patient record. In this example, a conflict resolver must evaluate the demographic data cited by the two abstractors and determine which are in fact appropriate for the "de facto" patient clinical record by selecting the correct "race" clinical data value.

Trigger #4B (intra-rater reliability): like the previously-disclosed trigger, the system also may be used to evaluate a plurality of abstractions from a single rater, in order to determine how consistent the rater is in his or her efforts. The notes or other clinical data reviewed by the rater may relate to the same patient, e.g., different portions of a patient's record, or they may be similar or distinct portions of raw clinical data from multiple patients.

Trigger #5 (case abstraction completion and/or quality assurance completion): clinical data attributes for the patient record may be evaluated systematically for gaps in logic through the use of a clinical data validation service that centralizes a number of rules (see below for details) and works in conjunction with a cohort sign-out process.

Trigger #6 (upon receipt of clinical data and/or records for patients participating in an institution's clinical trial): clinical data attributes for a patient potentially eligible for participation in a clinical trial may be evaluated on-demand or as part of a broader batch of patients from that institution on a rolling basis. With regard to this workflow, the present system and method may support the workflow's ability to identify gaps in clinical attributes that may be required for inclusion/exclusion criteria evaluation and matching.

Trigger #7 (on-demand analysis): structured data may be extracted, either directly or via a mapping procedure, from a clinical note while that note is being created or dictated by a physician or other clinician. The structured data is analyzed, and errors, incomplete information, or conflicting information in the underlying data are reported back to the clinician in real time.

Analysis Following Triggering Event

Regardless of the choice of triggering event, the default set of evaluation criteria (e.g. test suites) may be composed at a category-level (e.g. demographics, diagnosis, genetic testing and labs, treatments and outcomes) along with nested sub-groupings that allow for granular and precise evaluation of clinical patient attributes by type. For example, and with regard to the depiction in FIG. 64 of a list of test suites within a "demographics" root level category, a test may be written to determine whether a record of ovarian cancer was a correctly structured instance:

Primary tumor instance identified as part of a patient record

Tissue of origin identified for a corresponding primary tumor instance e.g. Ovary Date of diagnosis identified for a primary diagnosis e.g. Dec. 15, 2015

Date of recurrence identified for a primary diagnosis e.g. Mar. 5, 2016

Diagnosis (e.g. histology) identified for the corresponding primary diagnosis e.g. Ovarian stromal tumor Standard grade identified for the corresponding primary diagnosis e.g. Grade 2 (moderately differentiated)

AJCC staging identified for the corresponding primary diagnosis e.g. T1B, N0, M0 (Stage 1B)

In this example, a determination that the record was structured "correctly" may mean more than simply determining whether there are data values in each of the specified fields and attributes. Instead, correct structuring also may signify that all of the attributes listed were adequately provided and mapped to accepted and/or preferred medical concepts, i.e., that the requisite data was provided, represented, and properly fulfilled all validation checks managed by the system. Mapping may relate to both a system-defined data model as well as one or more external models, such as the Fast Healthcare Interoperability Resources ("FHIR") specification. In this regard, the system may include one or more test suites that define the criteria for the relevant categories and nested sub-groupings and then may execute relevant validation checks to carry out those test suites.

Medical concepts can span numerous dictionaries, vocabularies and ontologies, and data elements within structured data generally conform to a specific system, concept code and preferred text descriptor. For instance, in the example discussed above, for "Ovary," i.e., the tissue of origin identified for a corresponding primary tumor instance, the system may determine whether that data instance is mapped to the "SNOMED" code of 93934004 with a preferred text descriptor of "Primary malignant neoplasm of ovary (disorder)" in order to comply with a test suite that includes the same relationship.

Figures 64, 65, 66:
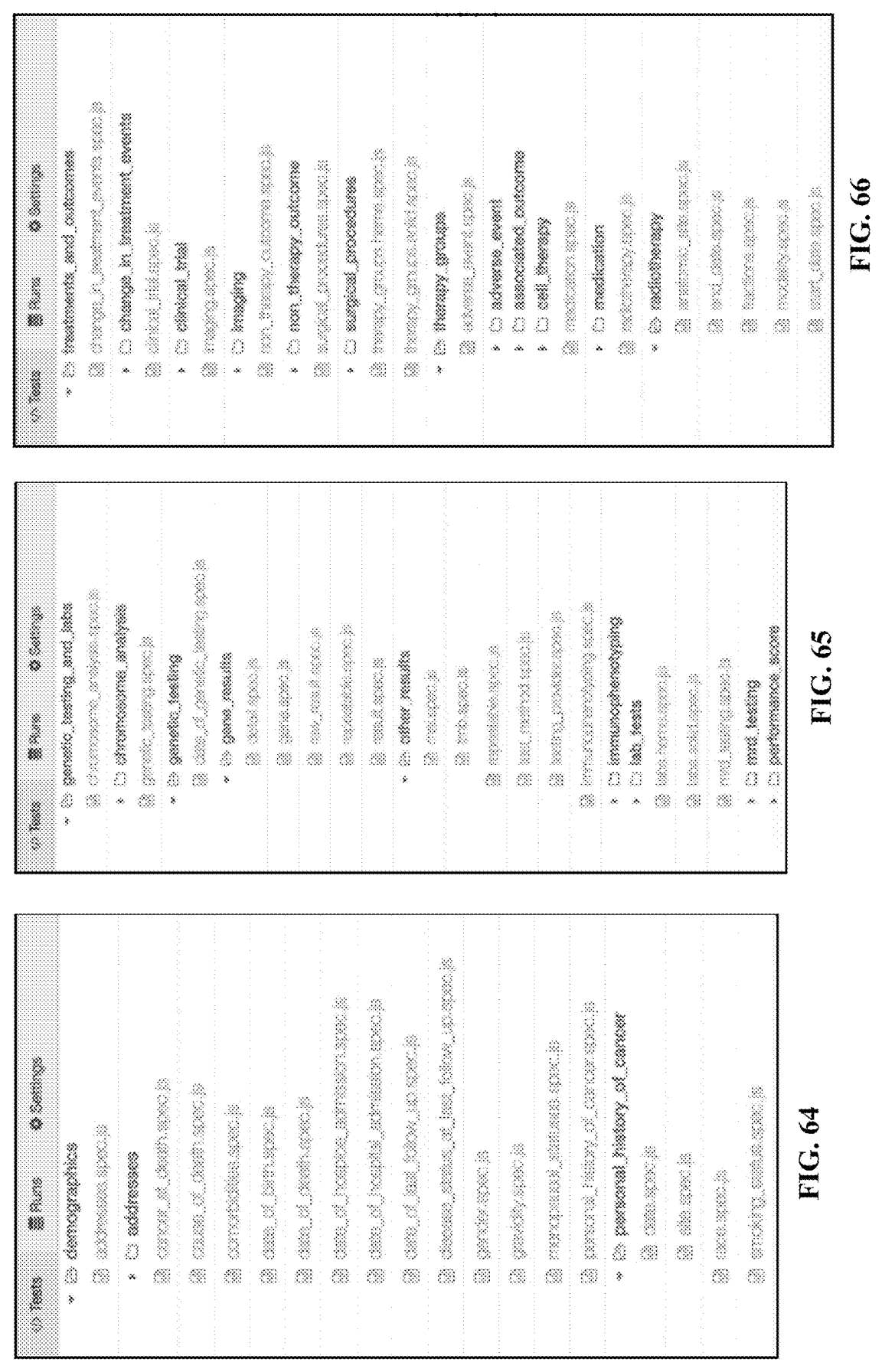

In a second example, and with regard to FIG. 65, the test suite for determining sufficiency of a structured and/or abstracted instance of genetic testing may include evaluating whether values for the following criteria are present and accurately structured:

Initial genetic testing instance identified and/or added to a patient record

Date identified for an instance of genetic testing e.g. Jan. 1, 2017

Testing provider identified for an instance of genetic testing e.g. Tempus

Test method identified for an instance of genetic testing e.g. Mutation analysis Gene result detail identified for an instance of genetic testing e.g. Gene: KRAS e.g. Result: Amplification e.g. Raw Result: 100 e.g. Detail: N/A

Tumor mutational burden identified for an instance of genetic testing e.g. 10

Microsatellite instability identified for an instance of genetic testing e.g. High In a third example, and with regard to FIG. 66, a test suite for determining sufficiency of a structured and/or abstracted instance of genetic testing may include the following criteria:

Initial genetic testing instance identified and/or added to a patient record

Date identified for an instance of genetic testing e.g. Jan. 1, 2017

Testing provider identified for an instance of genetic testing e.g. Tempus

Test method identified for an instance of genetic testing e.g. Mutation analysis Gene result detail identified for an instance of genetic testing e.g. Gene: KRAS e.g. Result: Amplification e.g. Raw Result: 100 e.g. Detail: N/A

Tumor mutational burden identified for an instance of genetic testing e.g. 10

Microsatellite instability identified for an instance of genetic testing e.g. High In one aspect, the evaluation and/or analysis performed as part of the system referenced above may comprise a combination of several of the trigger mechanisms discussed above. For example, the system may include: (1) automated and continuously maintained test suites specific to one or more clinical attributes and/or content types, (2) clinical data validation processes performed at run-time during abstraction as well as quality assurance activities, and (3) inter-rater reliability (IRR). Additionally, the triggers may evolve or be revised over time to generate a more robust, more complete quality assurance system. For example, test suites may grow continuously to support more templates or later-generated abstraction fields for clinical data structuring. Similarly, the clinical data validations (errors, warnings, etc.) may be maintained in a library programmatically via web service endpoints or a user interface that supports the addition of new validations and corresponding definitions of rules, e.g., using a rule builder. The system may generate multiple streams of abstracted clinical data that can be evaluated and re-assigned to a more sophisticated user with deeper clinical background to help resolve any conflicts, thereby producing a de facto "source of truth" for a given patient's clinical record.

In still another example, the system may rely on data from other patients to determine whether the data in a target patient's record appears correct or whether it may warrant an alert signifying a potential error or an otherwise unexpected finding. For example, a patient record may include both clinical and molecular data, where the molecular data may include data reflecting a "new" gene, in that there may not be much, if any, clinical knowledge regarding the medical effects of having the gene. In that case, the system may search its data store for indications of other patients with that gene. The system then may search for similarities in clinical data among those other patients in order to develop a template test suite. Thus, the system may assume that the other patients' clinical data is accurate, such that deviations from that data when a validation check is performed on a subject patient's data may trigger an alert to the provider or reviewer as to either an error in the subject patient's data or, alternatively, to an unexpected result that may warrant further investigation.

In one instance, validations may be fairly straightforward, e.g., when comparing different portions of a patient record, is the system able to extract a patient's gender from more than one location and do those gender-based attributes match up? In those instances, a test suite that instructs the system to query one or more known portions of a record for gender-identifying information, review that information for internal consistency (if more than one portion of the record is considered), and to return that gender as an attribute for the patient may be usable for multiple use cases as a fairly generic test suite. In another example, the test suite may seek to compare the structured patient data against a set of one or more guidelines, e.g., clinical trial inputs or metrics reflecting general patient population results (e.g., survival, progression, etc.), to determine whether the patient's data is in-line with those guidelines or reflects a potential error or outlier.

In another instance, validations may be specific to certain use cases based, e.g., on other data extracted from a patient record. For example, certain types of cancer are gender-specific. Thus, a quality assurance validation or rule that says "if structured data extracted from the patient record includes an attribute for prostate cancer, then a patient gender of 'female' represents an error" is useful for prostate cancer use cases but not for other cancers or diseases.

In still another instance, validations may be multi-variable or require more than a simple cross-check of two fields against one another. For example, with regard to lung or breast cancer, a patient record may document scenarios that reflect valid or invalid staging, and the relevant cancer also may have subtypes that vary based on staging. Thus, a complete validation check of a test suite may require that the system evaluate all of the possibilities at each stage to determine whether the structured data is complete and internally consistent.

Still further, the system may include an automated process for evaluating each test suite to determine whether it represents an accurate test. That process may require running through each of the possibilities that are queried in the test suite and determining that none of the tests conflict with other tests in the suite. Thus, e.g., the system may assume that a first test yields a "true" or valid result. Then, given that result, the system determines whether it is possible for a second test to also yield a "true" or valid result. The system continues in that process until a "false" or invalid result is reached or until all tests have been evaluated. In the latter case, the system may recognize that the test suite does not include any failures and may publish the test suite for actual implementation. In the former case, once an invalid result is determined, the system may flag the test suite for further review and either amendment or definitive approval, despite the invalid result.

One objective of the system is to allow for the creation, management and assignment of specific clinical data fields and their corresponding attributes via a single user interface. A dynamic management and rendering engine for template-specific fields enables the system to achieve this objective by permitting different classes of users to rapidly configure new templates with custom field configurations in minutes without code by employing a user interface that permits those users to select both the fields, as well as the hierarchy among the fields, that are desired for a given clinical data structuring project or use case. Templates may drive a determination of what content from the raw data is available to an abstractor. Finally, the system maintains a version history of every template modification made by authorized users for auditing purposes.

In addition to the single-user-centric analysis described above, in another aspect, validations can be leveraged at a more granular project-specific level (rather than at an individual level or a cohort level), which may allow for the evaluation and scoring of specific template configurations as well as their corresponding data fields. Thus, rather than running validations against a single patient's clinical data elements and content generally, the validation service also may be run with a batch or bulk set of patient clinical data elements that correspond to one or more projects. Data may be sourced from one or more sources, including upstream abstracted patient content (e.g., prior to structuring) or from more finalized versions of the data (e.g., from a downstream data warehouse in a structured format). Like the single-user-centric analysis described above, these bulk or test validation service checks may be configured to run either sequentially or simultaneously. The system may be configured to perform these validation checks on patients associated with projects that have been configured to these templates to ensure that data has been abstracted, captured and/or encoded properly.

Results of the foregoing validations may be output as structured code, e.g., in a JSON file format. The file may include one or more indicators describing which clinical data attributes passed or failed a particular validation. Similarly, results of a test suite processing all clinical data attributes may produce a result output as structured code, e.g., also in a JSON format, that describes which particular test(s) within the suite passed or failed for one or more given patient records passed to it.

Various System-Supported User Roles or Use Cases

The system may usable by a plurality of different users having distinct roles. For example, the following list describes various user roles or use cases, the corresponding actions each user may take, and one or more benefits that may result from use of the system as a result of those actions:

A clinical manager may want to evaluate a single patient, a project, an in-progress or completed cohort or one or more patients abstracted and/or QA'ed by a specific abstractor or lead user for accuracy. Additionally, this user may want to obtain an analysis of a data stream sourced externally (e.g. via EMR or structured data extract) to determine the need for further incremental abstraction of a patient's clinical record.

A single abstracted patient can be evaluated for accuracy through the use of the clinical data validation service either upon request, when the corresponding patient case is being submitted via Workbench or when clinical attributes are modified. Validation rules are run atop all structured clinical data for a single abstracted patient and pass/fail assignments are made as a result. The clinical data validation service also maintains an "effective as of" timestamp that ensures that only appropriate validations are run on a single abstracted patient at that point in time.

A project can be evaluated for accuracy through the use of the clinical data validation service either upon request or when the project is used as a filter within the QA Manager Console user interface. At this point in time, validation rules will have already been run atop all structured clinical data for all completed and submitted patients within the given project and pass/fail assignments are retrieved as a result. The clinical data validation service also maintains an "effective as of" timestamp that ensures that only appropriate validations are run on abstracted patients within a project at that point in time.

A cohort can similarly be evaluated for accuracy through the use of the clinical data validation service either upon request or when the cohort is used as a filter within the QA Manager Console. At this point in time, validation rules will have already been run atop all structured clinical data for all completed and submitted patients with the given cohort and pass/fail assignments are retrieved as a result. The clinical data validation service also maintains an "effective as of" timestamp that ensures that only appropriate validations are run on abstracted patients within a cohort at that point in time.

Externally sourced data streams may first be ingested and mapped to a source-specific schema by a member of an integrations team. Subsequently, the schema may be aligned to a clinical data model by a member of an informatics team that allows for mapping of concepts to a canonical set of systems, codes, and values. After the schema mapping and concept mapping steps, the clinical data validation service can evaluate an externally sourced patient record upon request by using the default set of validations checks. Further, source-specific custom rules and validations may be authored within the QA Manager Console to ensure proper coverage of all desired data integrity checks.

A clinical abstraction lead may want to identify gaps in abstraction for a patient and/or project assigned to their abstraction team, perhaps specific to a cancer type (e.g. colorectal team). In this instance, the clinical abstraction lead may want to obtain the IRR score for a project, manually initiate a test suite for one or more clinical data attributes as well as perform various validation checks. IRR scores at a project-level are aggregated and averaged across all eligible and completed IRR cases within that project. As a reminder, IRR case agreement thresholds and case eligibility percentage are configurable at the project level and will vary. A global set of validation checks are available via the clinical data validation service and can be run atop one or more patient records corresponding to a project.

A clinical data abstractor may want to preview content ingested from third party sources into various data streams and obtain a report consisting of quantitative insights specific to clinical data attributes (e.g. medications, procedures, adverse events, genetic testing, etc.) that will help them to more fully abstract a patient's clinical record from various disparate sources.

An operational lead may want to better understand data coverage and quality gaps specific to one or more patients or in aggregate across specific projects/cohorts. Further, they may want to receive automated notifications and warnings that will alert them to take action directly with health system content partners when data validations fail and/or the automated evaluation and scoring for various clinical data streams is insufficient.

A data scientist may want to integrate with the system to better train machine learning models based on various levels of priority and/or a trust scale for various clinical data ingested and/or structured across clinical data streams. For example, a project or cohort with a high IRR score, near-perfect clinical data validation checks and automated test suites passing may be treated preferentially to other unstructured or semi-structured clinical data with lower scores.

An integration and/or infrastructure engineer may want to monitor various clinical data streams being ingested from external sources to verify connectivity, data sufficiency as well as quality over time.

A quality assurance engineer may want to compare the output of their manually maintained clinical data test suites against externally sourced content programmatically or on an ad-hoc basis.

A product manager may want to better understand the project, cohort and/or field level scoring of either/both abstracted and structured data to determine further improvements to various workflows, user interfaces and design patterns to accelerate and further streamline the data structuring operation.

For each of the triggers discussed above, as well as for other events that may trigger the quality assurance testing disclosed herein, the system maintains a continuously growing set of stream-specific validations, warnings, and errors that help proactively inform and/or alert administrators of patient data quality and integrity issues. By making a request to the clinical data validation service, a supported application and any of its users can quickly identify whether a patient case, either individually or one within a specific cohort, has passed or failed one or more validation checks.

Validations may be managed through a QA Manager Console user interface where they are constructed and/or grouped for use as part of quality assurance activities (at a batch and/or cohort level) and as part of on-demand evaluation criteria for one or more patient records. These validations are also useful when accounting for inclusion and exclusion criteria specific to patient cohorts for research and/or clinical trial consideration purposes.

Figure 68:
FIG. 68 depicts an exemplary user interface for performing quality assurance testing based on generic abstractions from raw documents.
Figure 69:
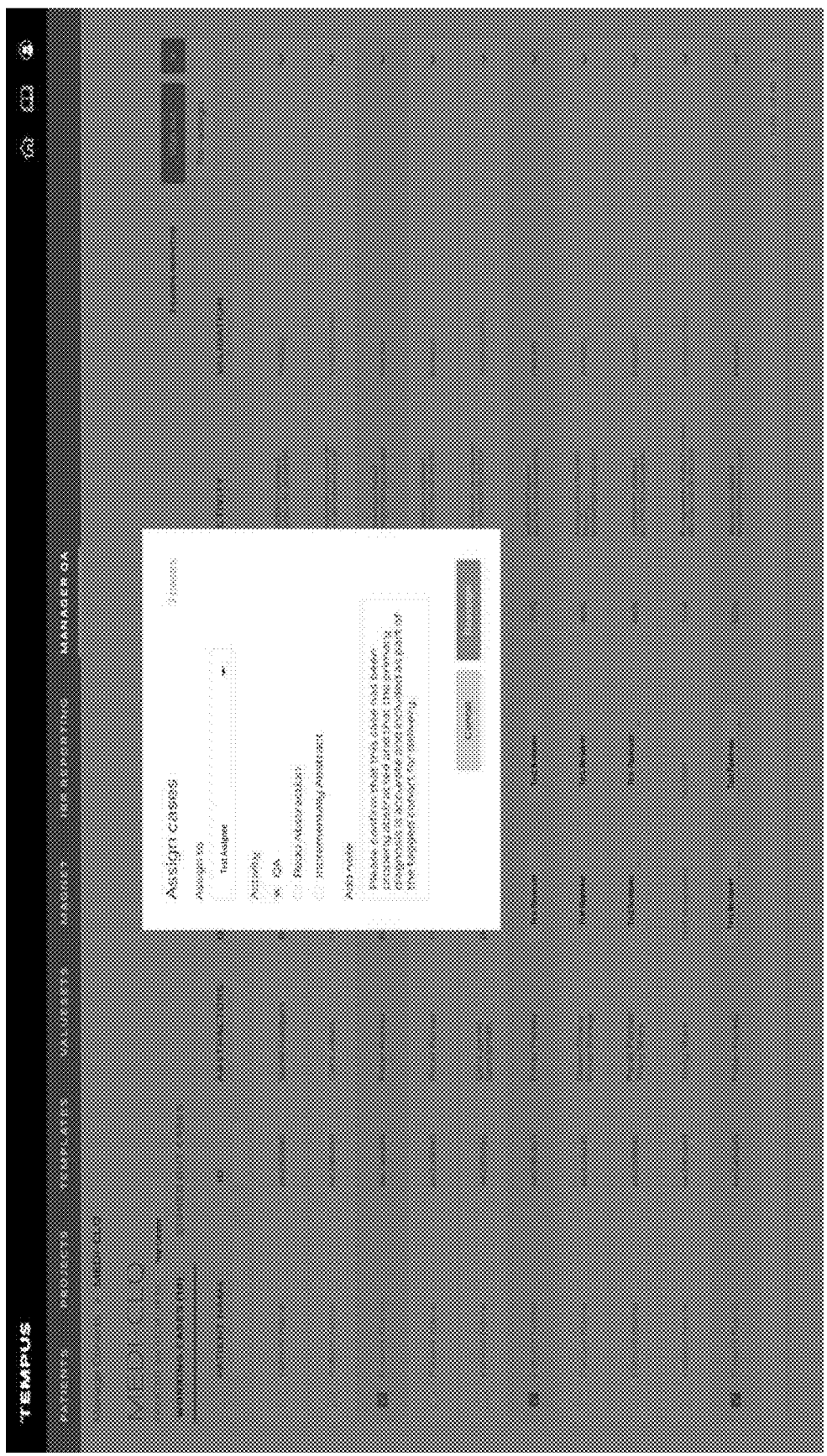
FIG. 69 depicts an exemplary user interface that is used to provide abstraction across multiple streams of raw clinical data and documents.
Figure 70:
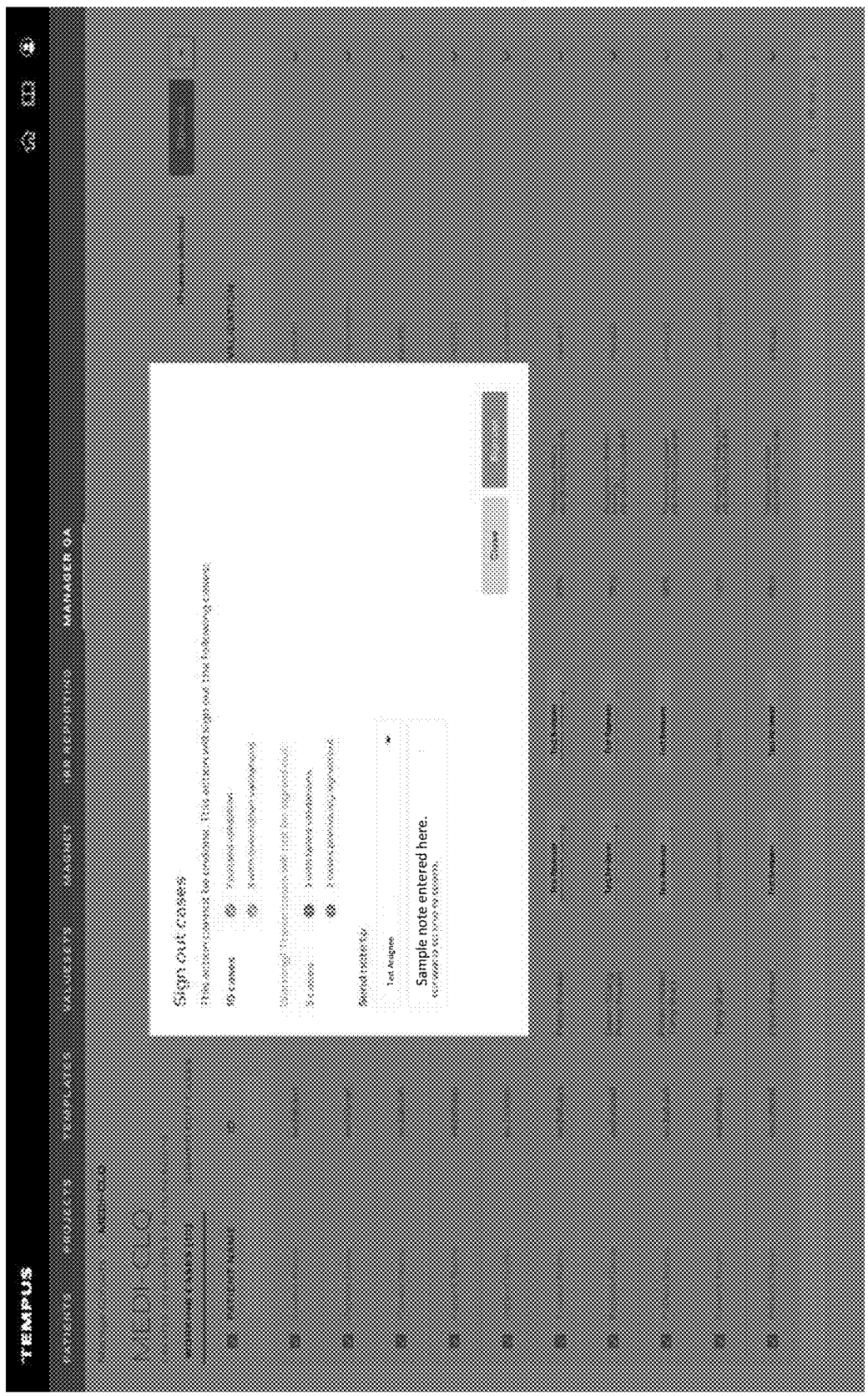
FIG. 70 depicts an exemplary user interface for performing an inter-rater reliability analysis.

FIGS. 67-70 depict one example of the user interface through which a manager-level user can view and maintain these validations, quickly determine which patient cases have passed or failed, obtain the specific detail about any failed validation, and quickly re-assign cases for further manual QA and issue resolution prior to clinical sign-out and approval. In particular, FIG. 68 depicts an exemplary user interface for performing quality assurance testing based on generic abstractions from raw documents. FIG. 69 depicts an exemplary user interface that is used to provide abstraction across multiple streams of raw clinical data and documents. FIG. 70 depicts an exemplary user interface for performing an inter-rater reliability analysis.

Figure 71:
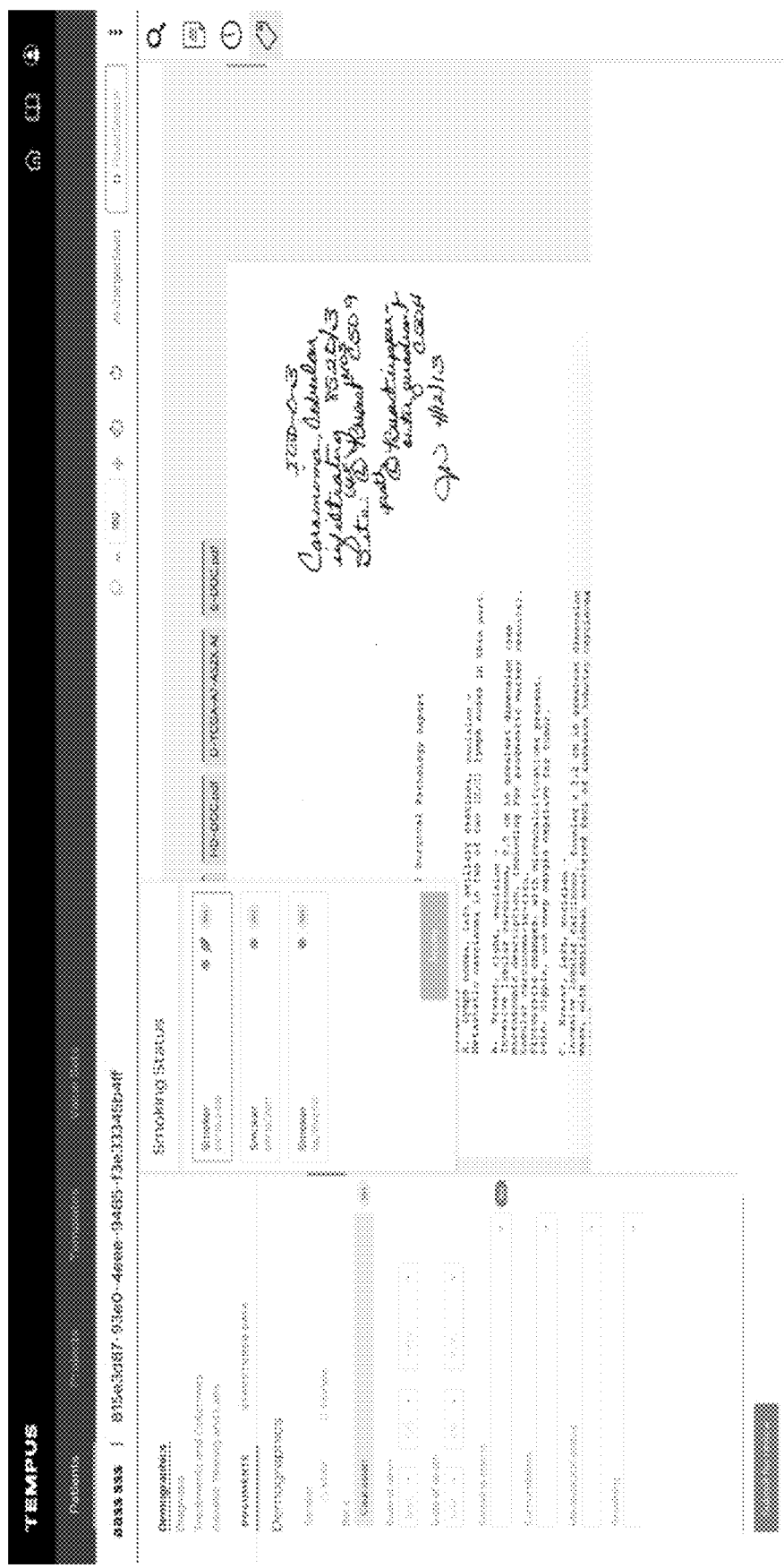
FIG. 71 depicts another exemplary user interface.
Figure 72:
FIG. 72 depicts one example of various metrics or reports generated by the present system.

In another aspect, FIG. 71 shows a second exemplary user interface that a clinical data analyst may utilize to compare, merge and generate a "single source of truth" patient record across multiple data schemas, sources and/or streams.

Turning now to FIGS. 72-75, the system additionally may output and/or deliver various metrics and reports that provide insight into the accuracy and/or completeness of patient clinical records specific to a project as well as across selected projects for comparative and benchmarking purposes. Reporting data may include rankings and scores at both the patient record and clinical data attribute/field grain, indicative of data source/stream quality, completeness and integrity. This information becomes available to clinical data abstractors within a data curation, abstraction, and/or structuring toolset and user interface to aid in their desire to generate a "single source of truth" consolidated patient record atop various sources. It can also be used by clinical data managers to ensure a high quality data product deliverable for partners. As seen in these figures, the system may generate outputs permitting a user to visualize the IRR scoring and conflict resolution processes, as well as to review the subsequent reporting and insights generated afterwards. Additionally, a sample visualization describing data quality across various clinical data attributes and types is included for reference.

Figure 74:
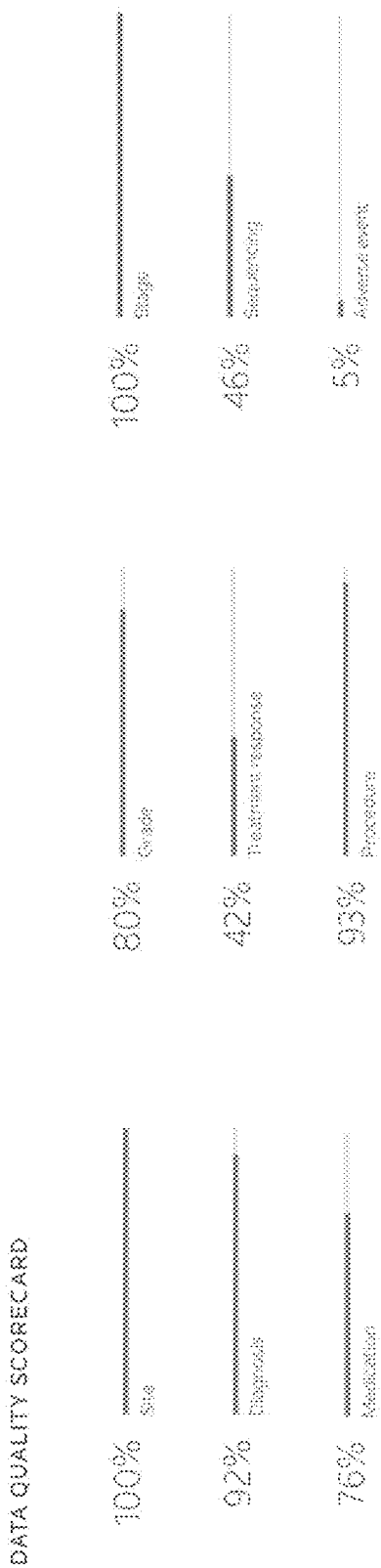
FIG. 74 depicts a third example of various metrics or reports generated by the present system.
Figure 75:
FIG. 75 depicts a fourth example of various metrics or reports generated by the present system.

With regard to the analytical tools described above, validation rules may be composed of hard, blocking errors (e.g., an indication of a new problem emerging after a recorded date of death) and loose warning notifications (e.g., an indication from one portion of the patient's record that the patient has stage 2 lung cancer while a second portion of the record indicates that the cancer is stage 3) that help to improve the integrity of a patient record during the clinical data structuring process as well as afterwards during subsequent QA activities. Because the system may include a "sliding scale" of error severity, the results of the data quality tests may not be an "all-or-nothing" situation. Instead, as seen in FIG. 74, the system may generate quantitative metrics such as a "% success" indicator to measure the accuracy of the data structuring. This indicator also may account for the fact that a test suite may comprise dozens, if not hundreds, of different validation checks and that some may return acceptable results while others may indicate errors, missing information, or incomplete information.

Figure 76:
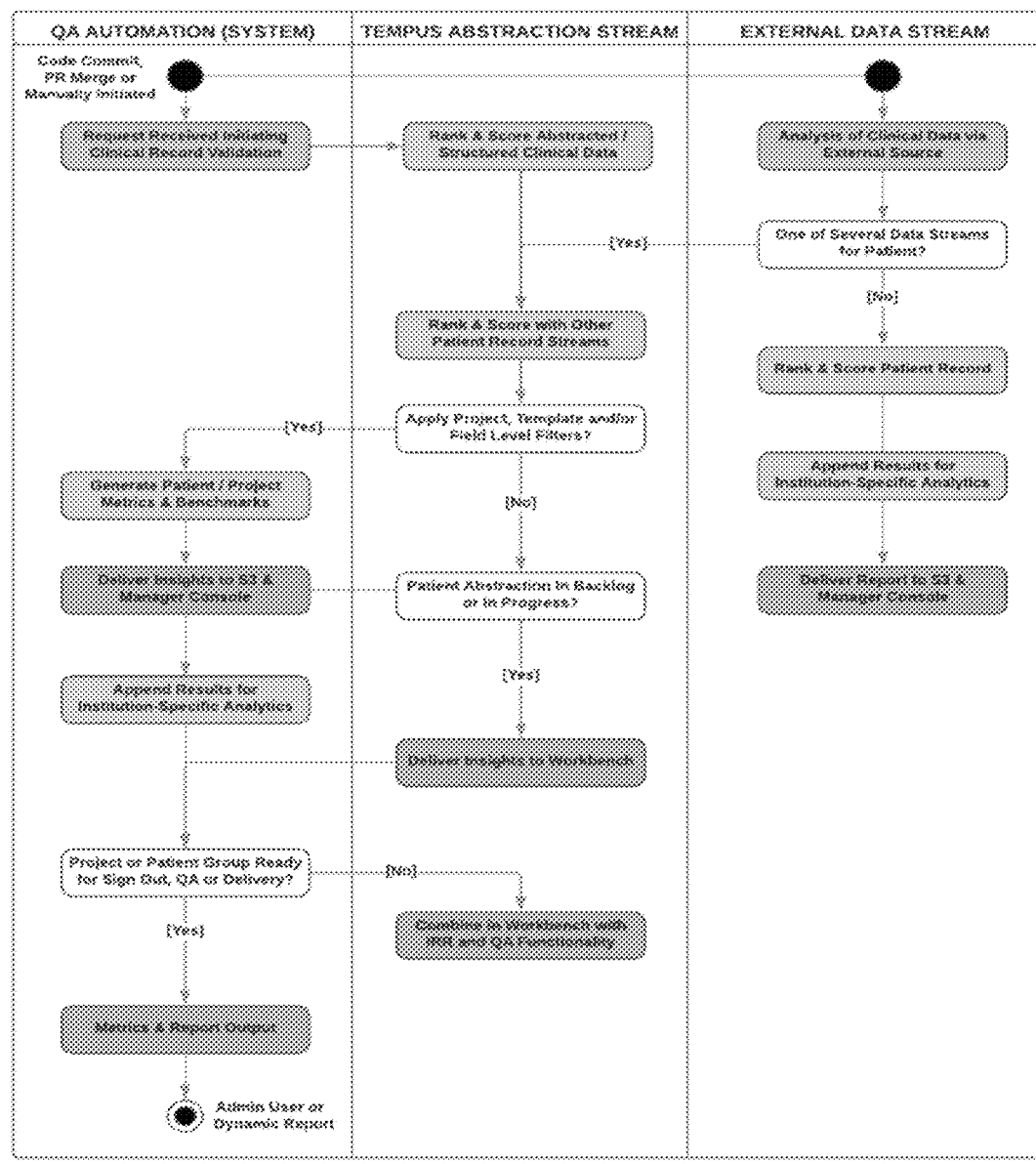
FIG. 76 reflects a generalized process flow diagram for carrying out the method disclosed herein, from raw data importation, through data structuring, and then through automated quality assurance testing.

Finally, FIG. 76 depicts one exemplary process flow of the present disclosure. In that figure, external data is received by the system, where it is ranked, scored, or otherwise structured, either on its own or in consideration with other data streams from the same patient. The structured data then is run through one or more QA Automation processes, such as the processes discussed herein in order to generate metrics and reports that can be output, e.g., to an administrative user or to the institution providing the external data.

The methods and systems described above may be utilized in combination with or as part of a digital and laboratory health care platform that is generally targeted to medical care and research, and in particular, generating a molecular report as part of a targeted medical care precision medicine treatment or research. It should be understood that many uses of the methods and systems described above, in combination with such a platform, are possible. An example of such a platform is described in U.S. patent application Ser. No. 16/657,804, titled "Data Based Cancer Research and Treatment Systems and Methods" (hereinafter "the '804 application"), which is incorporated herein by reference in its entirety for all purposes. In some aspects, a physician or other individual may utilize an abstraction engine comprising elements of artificial intelligence engine, such as the system 100 and server 120 for generating structured data from source documents, in connection with one or more expert treatment system databases shown in FIG. 1 of the '804 application. The abstraction engine and artificial intelligence engine of system 100 may operate on one or more micro-services operating as part of a systems, services, applications, and integration resources database, and the methods described herein may be executed as one or more system orchestration modules/resources, operational applications, or analytical applications. At least some of the methods (e.g., microservices) can be implemented as computer readable instructions that can be executed by one or more computational devices, such as the abstraction engine and artificial intelligence engine of system 100 and server 120. For example, an implementation of one or more embodiments of the methods and systems as described above may include microservices included in a digital and laboratory health care platform that can generate the patient's available features for use in deriving sequencing results, features for differing reporting tests, and as part of the reports themselves.

In some embodiments, a system may include a single microservice for receiving source documents containing patient data, generating a user interface including a first portion for displaying one of the source records at a time and a second portion for entering structured patient data, abstracting of one or more categories of patient data, including cancer diagnosis, staging, tumor size, genetic results, and date of recurrence, the abstraction performed by an assigned abstractor where the data is being pulled off that one source record, validation of abstracted patient data according to one or more validation rules applied to at least one of the categories, validation rules being assigned to the one or more projects, validations being performed on the one or more categories as they are populated; and abstraction review performed by an assigned abstractor or an abstraction manager, the abstraction review spanning one or more of the projects, or may include a plurality of microservices, each microservice having a particular role which together implement one or more of the embodiments above. In one example, a first microservice for generating a user interface including a first portion for displaying one of the source records at a time and a second portion for entering structured patient data; a second microservice for abstraction of one or more categories of patient data, including cancer diagnosis, staging, tumor size, genetic results, and date of recurrence, the abstraction performed by an assigned abstractor where the data is being pulled off that one source record; a third microservice for validation of abstracted patient data according to one or more validation rules applied to at least one of the categories, validation rules being assigned to the one or more projects, validations being performed on the one or more categories as they are populated; and a fourth microservice for abstraction review performed by an assigned abstractor or an abstraction manager, the abstraction review spanning one or more of the projects.

The artificial intelligence engine of system 100 may be utilized as a source for automated data generation of the kind identified in FIG. 59 of the '804 application. For example, the artificial intelligence engine of system 100 may interact with an order intake server to receive an order for abstracting patient information from a plurality of documents. Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above.

The digital and laboratory health care platform further includes one or more insight engines shown in FIG. 272 of the '804 application. Exemplary insight engines may include a tumor of unknown origin engine, a human leukocyte antigen (ILA) loss of homozygosity (LOH) engine, a tumor mutational burden (TPvIB) engine, a PD-L1 status engine, a homologous recombination deficiency (FWD) engine, a cellular pathway activation report engine, an immune infiltration engine, a microsatellite instability engine, a pathogen infection status engine, and so forth as described with respect to FIGS. 189, 199-200, and 266-270 of the '804 application. In an aspect, systems 100 and 120 may generate and subsequently provide structured data as an input for predictions, features including diagnosis of the patient as to an insight engine such as HLA LOH, TMB, PD-L1, HRD, active pathway, or other insight status.

When the digital and laboratory health care platform further includes a molecular report generation engine, the methods and systems described above may be utilized to create a summary report of a patient's genetic profile, patient features abstracted from source documents, and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ via a genetic analyzer. The report may further include therapies and/or clinical trials matched based on a portion or all of the genetic profile or insight engine findings and summaries shown in FIGS. 271 and 302 of the '804 application.

It should be understood that the examples given above are illustrative and do not limit the uses of the systems and methods described herein in combination with a digital and laboratory health care platform.

While the present disclosure may be susceptible to various modifications and alternative forms, specific embodiments have been shown by way of example in the drawings and have been described in detail herein. However, it should be understood that the present disclosure is not intended to be limited to the particular forms disclosed. Rather, the present disclosure is to cover all modifications, equivalents, and alternatives falling within the spirit and scope of the present disclosure as defined by the following appended claims.

This written description uses examples to disclose the present disclosure, including the best mode, and also to enable any person skilled in the art to practice the present disclosure, including making and using any devices or systems and performing any incorporated methods. The patentable scope of the present disclosure is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this present disclosure.

What is claimed is:

1. A computer program product implemented as computer readable instructions on a non-transitory computer readable medium, the product comprising:
   a plurality of microservices for interrogating patient datasets obtained from one or more electronic copies of source documents from one or more clinical records, the interrogating being according to one or more projects relying on the patient datasets, including:
   a first microservice for generating a first user interface displayed on an electronic display device, the first user interface including a first portion displaying a plurality of the source documents including at least two of a pathology report, a progress note, testing data, or an electronic medical record, and, concurrently, a second portion displaying structured patient data fields for entering structured patient data derived from the one or more source documents displayed in the first portion, the first user interface permitting a user to switch between the source documents without changing the second portion,
      the structured patient data fields organized into a plurality of categories, a choice of the plurality of categories and their organization defined by a template selected from among a plurality of templates,
      each structured patient data field of the selected template being associated with a valueset selected from among a plurality of possible user-selectable valuesets, whereby selecting the valueset associates the selected valueset with the respective structured patient data field of the selected template,
      each of the possible valuesets comprising a subset of values and a corresponding subset of codes,
      whereby selecting a value from each structured patient data field in the first user interface populates the respective structured patient data field with the value and stores a corresponding code of the corresponding subset of codes in a database, thereby encoding the selected value as one of the structured patient data based at least in part on the corresponding code,
      whereby modifying a valueset propagates the modification to all templates that utilize the valueset, and
      wherein the plurality of categories includes at least cancer diagnosis, cancer staging, tumor size, genetic results, and date of recurrence;
   a second microservice for validation of abstracted patient data according to one or more validation rules applied to at least one of the categories, validation rules being assigned to the one or more projects, validations being performed on the plurality of categories as they are populated; and
   a third microservice for abstraction review performed by an assigned abstractor or an abstraction manager, the abstraction review spanning one or more of the projects.

2. The computer program product of claim 1, wherein the plurality of templates are determined as a result of a selection of the one or more projects.

3. The computer program product of claim 1, wherein each template further defines one or more subcategories and one or more fields to be abstracted from a source document.

4. The computer program product of claim 1, wherein a category of the plurality of categories includes one or more subcategories.

5. The computer program product of claim 4, wherein a subcategory of the one or more subcategories includes one or more additional subcategories.

6. The computer program product of claim 4, wherein a subcategory of the one or more subcategories includes one or more fields, the one or more fields comprising the structured patient data fields or other data fields.

7. The computer program product of claim 1, wherein a category of the plurality of categories includes one or more fields, the one or more fields comprising the structured patient data fields or other data fields.

8. The computer program product of claim 7, wherein a field of the one or more fields includes one or more sets of data values having a data type, the one or more sets of data values comprising the subset of values of a valueset or other sets of values.

9. The computer program product of claim 8, wherein validation of the field includes comparing an abstraction entry to a list of data values selected from the one or more sets of data values.

10. The computer program product of claim 7, wherein a field of the one or more fields includes one or more data type indicators.

11. The computer program product of claim 10, wherein validation of the field includes comparing an abstraction entry to one of the one or more data type indicators.

12. The computer program product of claim 1, wherein the plurality of categories of patient data further includes at least one of next generation sequencing information, genetic sequencing information, laboratory result information, demographic information, diagnosis information, treatments information, and outcomes information.

13. The computer program product of claim 1, wherein the one or more validation rules include applying validations only after an effective date.

14. The computer program product of claim 1, wherein the one or more validation rules include one or more logical connectors, one or more subcategories of patient information, and one or more requirements for a field of the one or more subcategories of patient information.

15. The computer program product of claim 1, wherein the one or more validation rules includes a first error descriptor indicating a warning and a second error descriptor indicating an error.

16. The computer program product of claim 15, wherein a user is permitted to ignore a warning.

17. The computer program product of claim 15, wherein a number of warnings or errors a user encounters is recorded as a performance metric for the user.

18. The computer program product of claim 15, wherein the user interface prevents submission of a field when a validation rule indicates an error.

19. The computer program product of claim 1, wherein the user interface provides a summary of errors and warnings upon submission for user review and submits abstraction results based upon confirmation of submission.

20. The computer program product of claim 19, wherein submitting abstraction results includes storing data in a structured format.

21. The computer program product of claim 1, wherein the user interface is configured to permit a user to review one or more patients that fail one or more selected validation rule sets.

22. The computer program product of claim 1, wherein the product is integrated into an electronic medical records platform.

23. The computer program product of claim 1, wherein abstraction review includes assigning overlapping abstraction to more than one abstraction user.

24. The computer program product of claim 1, wherein abstraction review provides all records failing a validation rule to a user.

25. The computer program product of claim 1, wherein a user assigns an abstraction task to another user to resolve a record failing a validation rule.

26. The computer program product of claim 1, wherein the second microservice is configured to populate the plurality of categories in response to inputs received from an assigned abstractor or an artificial intelligence engine.

27. The computer program product of claim 1, wherein at least one of the microservices is targeted to a specific disease state.

28. The computer program product of claim 1, wherein the third microservice is configured to identify discrepancies between abstraction results from a plurality of abstractors.

29. The computer program product of claim 28, wherein a discrepancy score is a summation of all of the identified discrepancies, and wherein the discrepancy score is compared to a threshold.

30. A computer program product implemented as computer readable instructions on a non-transitory computer readable medium, the product comprising:
a plurality of microservices for interrogating patient datasets obtained from one or more electronic copies of source documents from one or more clinical records, the interrogating being according to one or more projects relying on the patient datasets, including:
a first microservice for generating a first user interface displayed on an electronic display device, the first user interface including a first portion displaying a plurality of the source documents including at least two of a pathology report, a progress note, testing data, or an electronic medical record, and, concurrently, a second portion displaying structured patient data fields for entering structured patient data derived from the one or more source documents displayed in the first portion, the first user interface permitting a user to switch between the source documents without changing the second portion,
the structured patient data fields organized into a plurality of categories, a choice of the plurality of categories and their organization defined by a template selected from among a plurality of templates,
a first structured patient data field of the selected template being associated with a first valueset selected from among a plurality of possible user-selectable valuesets, a second structured patient data field of the selected template being associated with a second valueset selected from among the plurality of possible user-selectable valuesets, and at least one structured patient data field of a second template of the plurality of templates being associated with the first valueset,
whereby, when building the selected template, selecting the first valueset associates the first valueset with the selected template,
whereby, when building the second template, selecting the first valueset associates the first valueset with the second template,
whereby modifying the at least one valueset propagates the modification to both the selected template and the second template, and
wherein the plurality of categories includes at least cancer diagnosis, cancer staging, tumor size, genetic results, and date of recurrence;

a second microservice for validation of abstracted patient data according to one or more validation rules applied to at least one of the categories, validation rules being assigned to the one or more projects, validations being performed on the plurality of categories as they are populated; and a third microservice for abstraction review performed by an assigned abstractor or an abstraction manager, the abstraction review spanning one or more of the projects.

31. A computer program product implemented as computer readable instructions on a non-transitory computer readable medium, the product comprising:

a plurality of microservices for interrogating patient datasets obtained from one or more electronic copies of source documents from one or more clinical records, the interrogating being according to one or more projects relying on the patient datasets, including:

a first microservice for generating a first user interface displayed on an electronic display device, the first user interface including a first portion displaying a plurality of the source documents including at least two of a pathology report, a progress note, testing data, or an electronic medical record, and, concurrently, a second portion displaying structured patient data fields for entering structured patient data derived from the one or more source documents displayed in the first portion, the first user interface permitting a user to switch between the source documents without changing the second portion, the structured patient data fields organized into a plurality of categories, a choice of the plurality of categories and their organization defined by a template selected from among a plurality of templates, each structured patient data field of the selected template being associated with a valueset selected from among a plurality of possible user-selectable valuesets, whereby selecting the valueset associates the selected valueset with the respective structured patient data field of the selected template, whereby modifying a valueset propagates the modification to all templates that utilize the valueset, and wherein the plurality of categories includes at least cancer diagnosis, cancer staging, tumor size, genetic results, and date of recurrence;

a second microservice for validation of abstracted patient data according to one or more validation rules applied to at least one of the categories, validation rules being assigned to the one or more projects, validations being performed on the plurality of categories as they are populated; and a third microservice for abstraction review performed by an assigned abstractor or an abstraction manager, the abstraction review spanning one or more of the projects.

\* \* \* \* \*